US012790641B2

United States Patent

(12) United States Patent
Berti et al.

(10) Patent No.: US 12,790,641 B2
(45) Date of Patent: *Nov. 10, 2026

(54) ENCODED ASSAYS

(71) Applicant: Pleno, Inc., San Diego, CA (US)

(72) Inventors: Lorenzo Berti, Poway, CA (US); Jeffrey Brodin, Poway, CA (US); Donald Brian Eidson, San Diego, CA (US); Christian Schlegel, Park City, UT (US); Angela Blum, San Diego, CA (US); Rachel Schowalter, San Diego, CA (US); Ludovic Vincent, San Diego, CA (US); Pieter Van Rooyen, San Diego, CA (US); Gavin Stone, San Diego, CA (US)

(73) Assignee: Pleno, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/391,323

(22) Filed: Dec. 20, 2023

(65) Prior Publication Data

US 2024/0247308 A1 Jul. 25, 2024

Related U.S. Application Data

(63) Continuation of application No. PCT/US2022/037785, filed on Jul. 21, 2022, which is
(Continued)

(51) Int. Cl.
*C12Q 1/6844* (2018.01)
*G16B 20/20* (2019.01)
*G16B 30/00* (2019.01)

(52) U.S. Cl.
CPC .......... *C12Q 1/6844* (2013.01); *G16B 20/20* (2019.02); *G16B 30/00* (2019.02)

(58) Field of Classification Search
None
See application file for complete search history.

(56) References Cited

U.S. PATENT DOCUMENTS

| | | | |
|---|---|---|---|
| 9,359,640 | B2 | 6/2016 | Wang et al. |
| 10,240,198 | B2 | 3/2019 | Dahl et al. |

(Continued)

FOREIGN PATENT DOCUMENTS

| | | | |
|---|---|---|---|
| EP | 0867506 | A1 | 9/1998 |
| EP | 1007725 | A1 | 6/2000 |

(Continued)

OTHER PUBLICATIONS

Chen, X., Sun, Y. C., Church, G. M., Lee, J. H., & Zador, A. M. (2018). Efficient in situ barcode sequencing using padlock probe-based BaristaSeq. Nucleic acids research, 46(4), e22-e22. (Year: 2018).*

(Continued)

*Primary Examiner* — Kaitlyn L Minchella
*Assistant Examiner* — Noah A. Auger
(74) *Attorney, Agent, or Firm* — Goodwin Procter LLP

(57) ABSTRACT

A method of conducting an assay for a set of targets, comprising: subjecting each target of a set of targets to a recognition event, in which each target is uniquely recognized by and bound to a recognition element associated with a code from a set of codes, thereby yielding a set of coded targets comprising the target and the recognition element; subjecting each recognition element of the set of coded targets to a transformation event, in which a molecular transformation of each recognition element produces a modified recognition element, thereby yielding a set of modified recognition elements comprising the code; subjecting each code of the set of modified recognition elements to an amplifying event, in which each code is amplified,
(Continued)

thereby yielding a set of amplified codes; subjecting each amplified code of the set of amplified codes to a detection event, thereby decoding the code.

27 Claims, 46 Drawing Sheets

Specification includes a Sequence Listing.

Related U.S. Application Data a continuation of application No. PCT/US2021/060647, filed on Nov. 23, 2021.

(60) Provisional application No. 63/346,307, filed on May 26, 2022, provisional application No. 63/345,866, filed on May 25, 2022, provisional application No. 63/332,245, filed on Apr. 18, 2022, provisional application No. 63/329,781, filed on Apr. 11, 2022.

(56) References Cited

U.S. PATENT DOCUMENTS 10,465,245 B2 11/2019 Mann et al.
10,501,791 B2 * 12/2019 Church ................ C12Q 1/6874
10,513,739 B2 12/2019 Zhang et al.
10,731,214 B2 8/2020 Dahl et al.
10,829,814 B2 11/2020 Fan et al.
10,829,821 B2 11/2020 Zhang et al.
10,837,879 B2 11/2020 Burns et al.
11,028,435 B2 6/2021 Kelley et al.
11,549,135 B2 1/2023 Engreitz
11,555,219 B2 1/2023 Kühnemund et al.
11,597,965 B2 3/2023 Nilsson et al.
11,680,284 B2 6/2023 Gore et al.
12,060,603 B2 8/2024 Bava
12,131,498 B2 10/2024 Babadi et al.
2004/0086892 A1 5/2004 Crothers et al.
2008/0269068 A1 10/2008 Church et al.
2011/0159499 A1 6/2011 Hindson et al.
2013/0084561 A1 4/2013 Coull et al.
2013/0224729 A1 8/2013 Church et al.
2014/0357497 A1 * 12/2014 Zhang .................. C12Q 1/6869 506/37
2015/0004600 A1 1/2015 Wang et al.
2015/0284786 A1 10/2015 Shapero et al.
2015/0369772 A1 12/2015 Van De Stolpe et al.
2016/0010085 A1 1/2016 Kwon et al.
2016/0108460 A1 4/2016 Lucero et al.
2016/0257991 A1 9/2016 Jarvius
2017/0183726 A1 6/2017 Church et al.
2018/0023124 A1 1/2018 Collins et al.
2018/0363039 A1 12/2018 Weng et al.
2019/0078150 A1 3/2019 Chen et al.
2019/0292581 A1 9/2019 Egidio et al.
2019/0309352 A1 10/2019 Buis et al.
2019/0352697 A1 11/2019 Jones
2020/0040376 A1 2/2020 Russel et al.
2020/0131570 A1 4/2020 Berti et al.
2020/0141961 A1 5/2020 Ahlfors
2020/0149037 A1 5/2020 Shum
2020/0224244 A1 7/2020 Nilsson et al.
2020/0232026 A1 7/2020 Mannion et al.
2020/0255821 A1 8/2020 Wang et al.
2020/0277664 A1 9/2020 Frenz
2020/0309784 A1 10/2020 Bertozzi et al.
2020/0362397 A1 11/2020 Zhou et al.
2021/0017587 A1 1/2021 Cai et al.
2021/0087625 A1 3/2021 Fan et al.
2021/0123098 A1 4/2021 Previte et al.
2021/0164039 A1 6/2021 Wang et al.
2021/0189460 A1 6/2021 Hosono et al.
2021/0198727 A1 7/2021 Kühnemund et al.
2021/0238680 A1 8/2021 Bava
2021/0277460 A1 9/2021 Bava
2021/0340618 A1 11/2021 Kühnemund et al.
2021/0355483 A1 11/2021 Chee et al.
2022/0025429 A1 1/2022 Liao et al.
2022/0157400 A1 5/2022 Struble et al.
2022/0186301 A1 6/2022 Nguyen et al.
2022/0228200 A1 7/2022 Bava
2022/0356509 A1 11/2022 Hwang et al.
2022/0358672 A1 11/2022 Babadi et al.
2022/0372654 A1 11/2022 Fu et al.
2022/0390442 A1 12/2022 Luo et al.
2022/0403457 A1 12/2022 Glezer et al.
2023/0020118 A1 1/2023 Davis et al.
2023/0021752 A1 1/2023 Kapur et al.
2023/0048356 A1 2/2023 Zobeck et al.
2023/0057571 A1 2/2023 Costa et al.
2023/0084407 A1 3/2023 Hernández Neuta et al.
2023/0088043 A1 3/2023 Kovacs et al.
2023/0115903 A1 4/2023 Hernández Neuta et al.
2023/0203570 A1 6/2023 Kovacs et al.
2023/0220474 A1 * 7/2023 Schoenbrunner .... C12Q 1/6883 435/6.11
2023/0257801 A1 8/2023 Brodin et al.
2023/0279475 A1 9/2023 Kühnemund et al.
2023/0295739 A1 9/2023 Brodin et al.
2023/0374572 A1 11/2023 Kovacs et al.
2024/0124920 A1 4/2024 Van Rooyen et al.
2024/0254545 A1 8/2024 Wang et al.
2024/0263222 A1 8/2024 Lawson et al.
2024/0309424 A1 9/2024 Blum et al.
2024/0309450 A1 9/2024 Brodin et al.
2024/0417795 A1 12/2024 Gore et al.

FOREIGN PATENT DOCUMENTS

EP 1141417 A1 10/2001
EP 1252334 A2 10/2002
EP 1297179 B1 9/2008
EP 1399588 B1 8/2010
EP 1558764 B1 1/2011
EP 2464753 A1 6/2012
EP 1423532 B1 5/2013
EP 2773452 A1 9/2014
EP 1745155 B1 10/2014
EP 2885638 A2 6/2015
EP 2954315 A2 12/2015
EP 2971121 A1 1/2016
EP 2456888 B1 4/2016
EP 3041957 A1 7/2016
EP 2504448 B1 10/2016
EP 2627781 B1 2/2017
EP 2236622 B1 9/2017
EP 3074535 B1 10/2017
EP 3383994 A1 10/2018
EP 3507364 A1 7/2019
EP 3541950 A1 9/2019
EP 3583214 A1 12/2019
EP 3126523 B1 2/2020
EP 3619326 A1 3/2020
EP 2885638 B1 4/2020
EP 3668998 A1 6/2020
EP 3696275 A1 8/2020
EP 3789490 A1 3/2021
EP 3798318 A1 3/2021
EP 3818177 A1 5/2021
EP 3555317 B1 6/2021
EP 3837365 A1 6/2021
EP 3770273 B1 9/2021
EP 3892735 A1 10/2021
EP 3918090 A1 12/2021
EP 3947721 A1 2/2022
EP 3976817 A1 4/2022
EP 4004234 A1 6/2022
EP 3872187 B1 9/2022
EP 4073270 A1 10/2022
EP 4388126 A1 6/2024
EP 4453247 A1 10/2024
WO WO-9747769 A1 12/1997
WO WO-9811210 A1 3/1998

(56) References Cited

FOREIGN PATENT DOCUMENTS

| | | | | |
|---|---|---|---|---|
| WO | WO-9949079 A1 | | 9/1999 | |
| WO | WO-0036141 A1 | | 6/2000 | |
| WO | WO-0157256 A2 | | 8/2001 | |
| WO | WO-2004044549 A2 | | 5/2004 | |
| WO | WO-2005010199 A2 | | 2/2005 | |
| WO | WO-2005061735 A2 | | 7/2005 | |
| WO | WO-2007061284 A1 | | 5/2007 | |
| WO | WO-2007120208 A2 | | 10/2007 | |
| WO | WO-2011019874 A1 | | 2/2011 | |
| WO | WO-2011066476 A1 | | 6/2011 | |
| WO | WO-2012049316 A1 | | 4/2012 | |
| WO | WO-2013066975 A1 | | 5/2013 | |
| WO | WO-2014011673 A2 | | 1/2014 | |
| WO | WO-2014122548 A2 | | 8/2014 | |
| WO | WO-2014144371 A1 | | 9/2014 | |
| WO | WO-2015035087 A1 | | 3/2015 | |
| WO | WO-2015079042 A1 | | 6/2015 | |
| WO | WO-2016134191 A1 | * | 8/2016 | ........... C12Q 1/6827 |
| WO | WO-2017087560 A1 | | 5/2017 | |
| WO | WO-2017096322 A1 | | 6/2017 | |
| WO | WO-2018045181 A1 | | 3/2018 | |
| WO | WO-2018094031 A1 | | 5/2018 | |
| WO | WO-2018109206 A1 | | 6/2018 | |
| WO | WO-2018144813 A1 | | 8/2018 | |
| WO | WO-2018204423 A1 | | 11/2018 | |
| WO | WO-2019068880 A1 | | 4/2019 | |
| WO | WO-2019195268 A2 | | 10/2019 | |
| WO | WO-2019199696 A1 | | 10/2019 | |
| WO | WO-2020010255 A1 | | 1/2020 | |
| WO | WO-2020069350 A1 | | 4/2020 | |
| WO | WO-2020124050 A1 | | 6/2020 | |
| WO | WO-2020180778 A1 | | 9/2020 | |
| WO | WO-2020193769 A1 | | 10/2020 | |
| WO | WO-2020240025 A1 | * | 12/2020 | ........... C12Q 1/6816 |
| WO | WO-2021007099 A1 | | 1/2021 | |
| WO | WO-2021021982 A1 | | 2/2021 | |
| WO | WO-2021033981 A1 | | 2/2021 | |
| WO | WO-2021118435 A1 | | 6/2021 | |
| WO | WO-2021123282 A1 | | 6/2021 | |
| WO | WO-2021123286 A1 | | 6/2021 | |
| WO | WO-2021146636 A1 | | 7/2021 | |
| WO | WO-2022026891 A1 | | 2/2022 | |
| WO | WO-2022040147 A1 | | 2/2022 | |
| WO | WO-2022109496 A2 | | 5/2022 | |
| WO | WO-2022159474 A1 | | 7/2022 | |
| WO | WO-2022164989 A2 | | 8/2022 | |
| WO | WO-2022197589 A1 | | 9/2022 | |
| WO | WO-2022235764 A1 | | 11/2022 | |
| WO | WO-2022236011 A1 | | 11/2022 | |
| WO | WO-2022251586 A1 | | 12/2022 | |
| WO | WO-2023283442 A1 | * | 1/2023 | ........... C12Q 1/6841 |
| WO | WO-2023015192 A1 | | 2/2023 | |
| WO | WO-2023021518 A1 | | 2/2023 | |
| WO | WO-2023077109 A2 | | 5/2023 | |
| WO | WO-2023096671 A1 | | 6/2023 | |
| WO | WO-2023096672 A1 | | 6/2023 | |
| WO | WO-2023096674 A1 | | 6/2023 | |
| WO | WO-2023096675 A1 | | 6/2023 | |
| WO | WO-2023102245 A1 | | 6/2023 | |
| WO | WO-2023122345 A1 | | 6/2023 | |
| WO | WO-2023141588 A1 | | 7/2023 | |
| WO | WO-2023158993 A2 | | 8/2023 | |
| WO | WO-2025019647 A1 | | 1/2025 | |
| WO | WO-2025090495 A1 | | 5/2025 | |

OTHER PUBLICATIONS

LaFratta, C. N., & Walt, D. R. (2008). Very high density sensing arrays. Chemical reviews, 108(2), 614-637. (Year: 2008).*

Pourjahed, A., Rabiee, M., & Tahriri, M. (2013). An efficient covalent coating on glass slides for preparation of optical oligonucleotide microarrays. Iranian Journal of Basic Medical Sciences, 16(12), 1259. (Year: 2013).*

Clausson, Carl-Magnus, Linda Arngården, Omer Ishaq, Axel Klaesson, Malte Kühnemund, Karin Grannas, Björn Koos et al. "Compaction of rolling circle amplification products increases signal integrity and signal-to-noise ratio." Scientific reports 5, No. 1 (2015): 12317. (Year: 2015).*

Lizardi, P. M., Huang, X., Zhu, Z., Bray-Ward, P., Thomas, D. C., & Ward, D. C. (1998). Mutation detection and single-molecule counting using isothermal rolling-circle amplification. Nature genetics, 19(3), 225-232. (Year: 1998).*

Gataric, M., Park, J. S., & Li, T. (2021). PoSTcode: probabilistic image-based spatial transcriptomics decoder. bioRxiv. (Year: 2021).*

Ke, R., Mignardi, M., Pacureanu, A., Svedlund, J., Botling, J., Wählby, C., & Nilsson, M. (2013). In situ sequencing for RNA analysis in preserved tissue and cells. Nature methods, 10(9), 857-860. (Year: 2013).*

Kühnemund, M., Hernández-Neuta, I., Sharif, M. I., Cornaglia, M., Gijs, M. A., & Nilsson, M. (2017). Sensitive and inexpensive digital DNA analysis by microfluidic enrichment of rolling circle amplified single-molecules. Nucleic Acids Research, 45(8), e59-e59. (Year: 2017).*

Galanti, L., Shasha, D., & Gunsalus, K. C. (2021). Pheniqs 2.0: accurate, high-performance Bayesian decoding and confidence estimation for combinatorial barcode indexing. BMC bioinformatics, 22, 1-16. (Year: 2021).*

Margeridon, S., (2008). Rolling circle amplification, a powerful tool for genetic and functional studies of complete hepatitis B virus genomes from low-level infections and for directly probing covalently closed circular DNA. Antimicrobial agents and chemotherapy, 52(9), 3068-3073. (Year: 2008).*

Hardenbol, P., Banér, J., Jain, M., Nilsson, M., Namsaraev, E. A., Karlin-Neumann, G. A., . . . & Davis, R. W. (2003). Multiplexed genotyping with sequence-tagged molecular inversion probes. Nature biotechnology, 21(6), 673-678. (Year: 2003).*

Chung et al., Deterministic droplet-based co-encapsulation and pairing of microparticles via active sorting and downstream merging. Lab Chip. 17(21):3664-3671 (2017).

Holmes et al., Modular non-repeating codes for DNA storage. arXiv:1606.01799v2, pp. 1-41 2016.

Lareau et al., Droplet-based combinatorial indexing for massive-scale single-cell chromatin accessibility. Nat Biotechnol. 916-924 (2019).

PCT/US2022/037785 International Search Report and Written Opinion dated Dec. 30, 2022.

Unknown, Pleno Deploys its Raptor Instrument Platform Available with TotalSeq™ Antibodies from BioLegend. Pleno Press Releases, 1pg. Jan. 8, 2024. Available at https://plenoinc.com/about/news/.

Chen, Weigang et al., Low-complexity and highly robust barcodes for error-rich single molecular sequencing. 3 Biotech. 11(2):78, pp. 1-11 (2021).

PCT/US2022/037785 Invitation to Pay Additional Fees dated Sep. 29, 2022.

* cited by examiner

| | Total Bases In Sequence (Including Header and Tail) | Total Bases In Code Word (proper) | Total, Full Pyro Cycles (in a Code Word proper) |
|---|---|---|---|
| Locus Code #1 | 28 | 26 | 10 |
| Locus Code #2 | 28 | 26 | 10 |
| Locus Code #3 | 29 | 27 | 10 |
| | | | |
| d_min of CWs set | | | |
| 25 | | | |

(A)
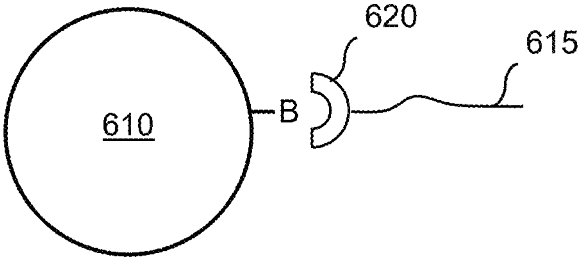
(B)
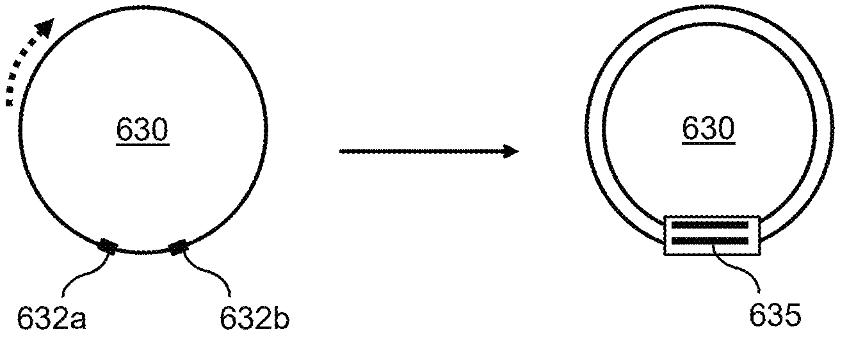
*FIG. 6*

2600

2700

Probe
+
Oligo-immobilization

Palindrome probe
+
Oligo-immobilization

Palindrome probe
+
Polypeptide-immobilization

2900

2910

RCA on PLL-coated MiSeq flowcell

RCA on PLL-coated Microplate

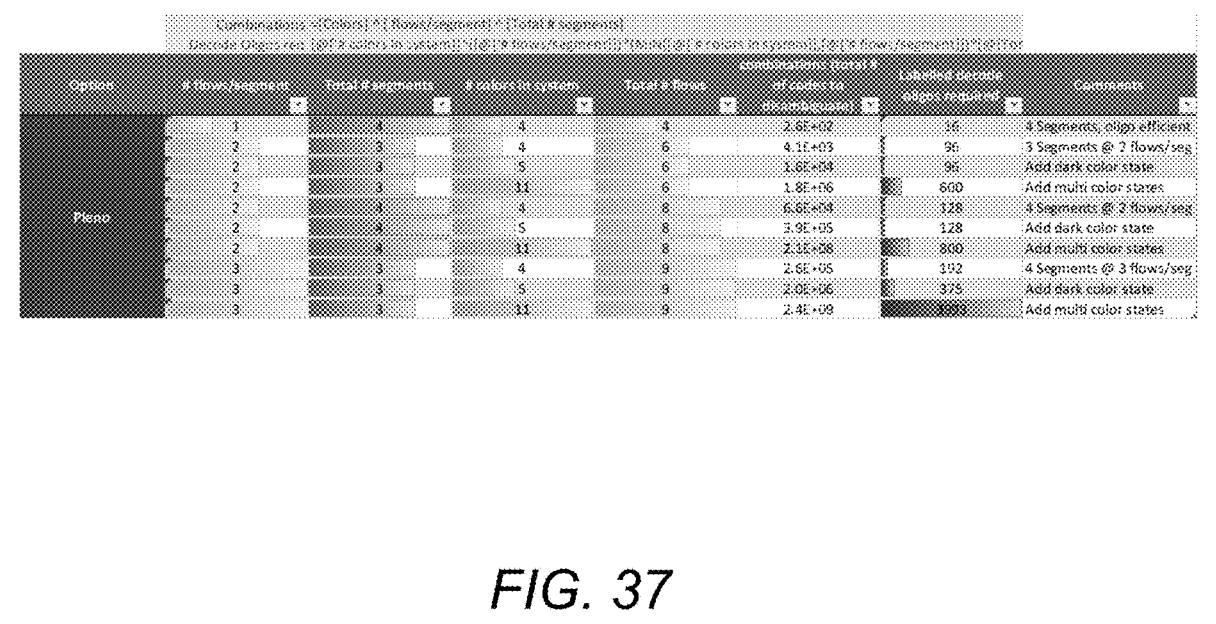

Combinations =[Colors] ^ [ flows/segment] ^ [Total # segments]

Decode Oligos req. [illegible]

| Option | # flows/segment | Total # segments | # colors in system | Total # flows | combinations (total # of codes to disambiguate) | Labeled decode oligos required | Comments |
|---|---|---|---|---|---|---|---|
| Pleno | 1 | 4 | 4 | 4 | 2.6E+02 | 16 | 4 Segments, oligo efficient |
| | 2 | 3 | 4 | 6 | 4.1E+03 | 96 | 3 Segments @ 2 flows/seg |
| | 2 | 3 | 5 | 6 | 1.6E+04 | 96 | Add dark color state |
| | 2 | 3 | 11 | 6 | 1.8E+06 | 600 | Add multi color states |
| | 2 | 4 | 4 | 8 | 6.6E+04 | 128 | 4 Segments @ 2 flows/seg |
| | 2 | 4 | 5 | 8 | 3.9E+05 | 128 | Add dark color state |
| | 2 | 4 | 11 | 8 | 2.1E+08 | 800 | Add multi color states |
| | 3 | 3 | 4 | 9 | 2.6E+05 | 192 | 4 Segments @ 3 flows/seg |
| | 3 | 3 | 5 | 9 | 2.0E+06 | 375 | Add dark color state |
| | 3 | 3 | 11 | 9 | 2.4E+09 | [illegible] | Add multi color states |

FIG. 37

| Targets | 10 | 100 | 1,000 | 10,000 |
|---|---|---|---|---|
| Code Space | 256 | 65,536 | 9,765,625 | 10,000,000,000 |
| Segments | 4 | 4 | 4 | 4 |
| # Flows (time) | 4 | 8 | 10 | 10 |
| Colors | 4 | 4 | 5 | 10 |

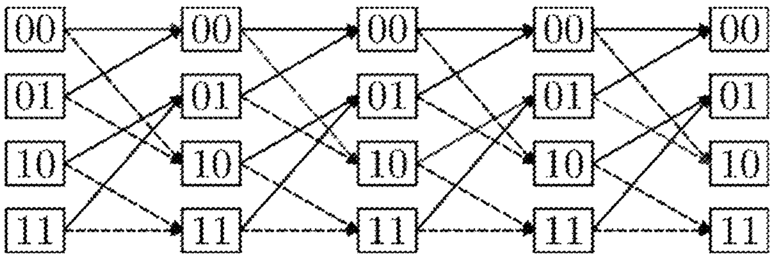

*Trellis code modulation*

```
Code = zeros(nbcw,Lg);                  % all 4-level codewords
[zerowd,zerobinary,punctzerobinary] = CCencoder(Gc,U(1,:),map,puncture);
minH = inf;                             % min Hamming weight = distance
for c=1:nbcw                            % generate all codewords
    u = U(c,:);                         % pick codeword
    [codewd,binarywd,punctbinarywd] = CCencoder(Gc,u,map,puncture);
    if c>1                              % compare to zero codeword
        Hweight = sum(codewd ~= zerowd);
        minH = min(minH,Hweight);
        if minH == Hweight              % find minimum weight codeword
            minHcw = binarywd;          % if there is only one!
            minHpunctcw = punctbinarywd;
        end
    else
        zerowd = codewd;
    end
    Code(c,:) = codewd;
end
```

High efficiency transmission over band-limited channels using quaternary numeral system (4 color system)

Enables error correction in the system to maximize decoding sensitivity and minimize overall error rate From a code space of 65,536 possible codewords → select 128 error correcting hypercodes

*FIG. 39*

| Excluded sequences | | | | |
|---|---|---|---|---|
| Hairpins | Primer dimers | | Uniqueness | |
| Seq 3 | Seq 4 | Seq [illegible] | Seq [illegible] | Seq 23 |
| Seq 7 | Seq [illegible] | Seq 4 | Seq 23 | Seq [illegible] |
| Seq 11 | Seq 25 | Seq [illegible] | Seq 14 | Seq [illegible] |
| Seq 13 | Seq [illegible] | Seq 25 | Seq 10 | Seq [illegible] |
| Seq 15 | Seq 12 | Seq [illegible] | Seq [illegible] | Seq 10 |
| Seq 26 | Seq [illegible] | Seq 12 | Seq [illegible] | Seq 34 |
| Seq 29 | Seq 8 | Seq [illegible] | Seq 34 | Seq [illegible] |
| Seq 36 | Seq [illegible] | Seq 8 | Seq [illegible] | Seq 9 |
| Seq 39 | | | | |
| Seq 48 | | | | |
| Seq 49 | | | | |

Highest Tm = 57°C (on target)
Lowest Tm = 48°C (on target)

Highest Tm = 23°C (off target)
Highest Tm = 23°C (primer dimers)

Lists of 10's-100's segments are generated with different requirements

*FIG. 40B*

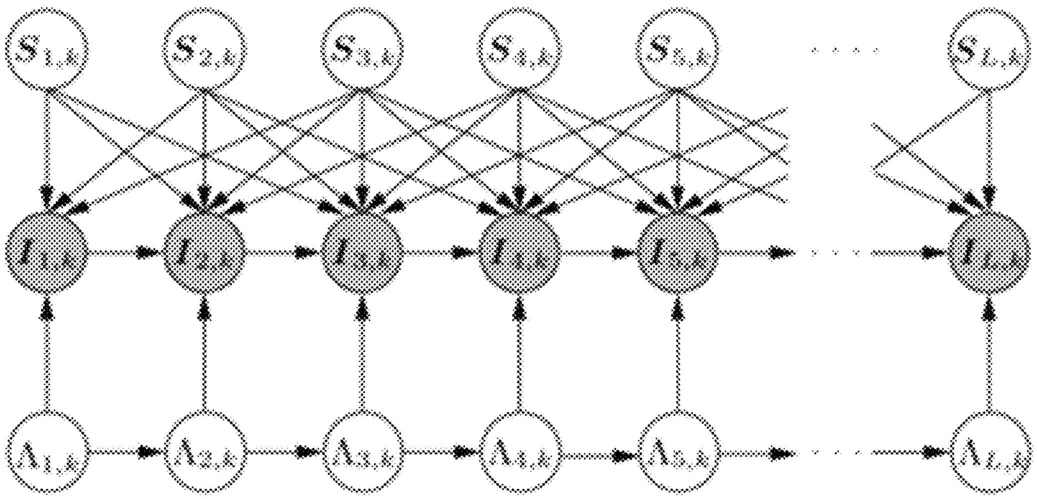

- Modelled after probabilistic next generation sequencing basecalling algorithm – NaïveBayesCall
- Model includes
  - Signal decay
    - lower signal from features over subsequent hybridization events
  - Amplitude noise
    - intensity fluctuations for each feature
  - Color crosstalk
    - bleed over of signal among channels
  - Signal leakage in time
    - rising background, non-specific binding, etc.
  - System noise

*FIG. 43*

SEQUENCE LISTING

```
Sequence total quantity: 8
SEQ ID NO: 1          moltype = DNA  length = 28
FEATURE               Location/Qualifiers
source                1..28
                      mol_type = other DNA
                      organism = synthetic construct
SEQUENCE: 1
actagcagct actgactaga gagtgcag                                  28

SEQ ID NO: 2          moltype = DNA  length = 28
FEATURE               Location/Qualifiers
source                1..28
                      mol_type = other DNA
                      organism = synthetic construct
SEQUENCE: 2
agtctgcaga tagtagctgc tgcagctg                                  28

SEQ ID NO: 3          moltype = DNA  length = 29
FEATURE               Location/Qualifiers
source                1..29
                      mol_type = other DNA
                      organism = synthetic construct
SEQUENCE: 3
agcagtatgc tagtgcgcta ctactatag                                 29

SEQ ID NO: 4          moltype = DNA  length = 15
FEATURE               Location/Qualifiers
```

-continued

```
source                  1..15
                        mol_type = other DNA
                        organism = synthetic construct
SEQUENCE: 4
tcgtctgtaa ccatt                                                  15

SEQ ID NO: 5            moltype = DNA  length = 13
FEATURE                 Location/Qualifiers
source                  1..13
                        mol_type = other DNA
                        organism = synthetic construct
SEQUENCE: 5
tcgtctgtaa cca                                                    13

SEQ ID NO: 6            moltype = DNA  length = 15
FEATURE                 Location/Qualifiers
source                  1..15
                        mol_type = other DNA
                        organism = synthetic construct
SEQUENCE: 6
atgacgtact tacgc                                                  15

SEQ ID NO: 7            moltype = DNA  length = 15
FEATURE                 Location/Qualifiers
source                  1..15
                        mol_type = other DNA
                        organism = synthetic construct
SEQUENCE: 7
ttgacactta gtacc                                                  15

SEQ ID NO: 8            moltype = DNA  length = 15
FEATURE                 Location/Qualifiers
source                  1..15
                        mol_type = other DNA
                        organism = synthetic construct
SEQUENCE: 8
ggattcgatt agtag                                                  15
```

ENCODED ASSAYS

RELATED APPLICATIONS

This application is a continuation application of International Application No. PCT/US2022/037785, filed Jul. 21, 2022, which claims the benefit of U.S. Provisional Application No. 63/346,307, filed on May 26, 2022, U.S. Provisional Application No. 63/345,866, filed on May 25, 2022, U.S. Provisional Application No. 63/332,245, filed on Apr. 18, 2022, U.S. Provisional Application No. 63/329,781, filed on Apr. 11, 2022, and International Patent Application No. PCT/US2021/060647, filed on Nov. 23, 2021, each of which is herein incorporated by reference in its entirety.

SEQUENCE LISTING

The instant application contains a Sequence Listing which has been submitted electronically in XML file format and is hereby incorporated by reference in its entirety. Said XML copy, created on Apr. 11, 2024, is named 64100-718_301_SL.xml and is 8,015 bytes in size.

FIELD OF THE INVENTION

The invention relates to encoded assays, in which a target analyte is detected based on association of the target with a code, and detection of the code as a surrogate for detection of the target analyte.

BACKGROUND OF THE INVENTION

Many assays such as single base detection assays require high-level of sensitivity and specificity and are associated with low signal level. Low signal requires amplification (e.g., PCR, immunostaining cascades, and the like) resulting in complex and lengthy protocols, high-level of background and other biases limiting the performance of the assay. There is a need in the art for assays that are easier to read and detect at higher sensitivity than the analyte itself.

BRIEF DESCRIPTION OF DRAWINGS

The features and advantages of the present invention will be more clearly understood from the following description taken in conjunction with the accompanying drawings, which are not necessarily drawn to scale, and wherein:

FIG. 3 discloses SEQ ID NOS 1-3, respectively, in order of appearance.

FIG. 6A is a schematic diagram illustrating an example of adding an index sequence to a probe using a ligand protein coupling strategy.

FIG. 6B is a schematic diagram illustrating an example of adding an index sequence to a probe by restriction endonuclease cleavage followed by index ligation.

FIG. 37 is a screenshot of an example of the permutations (e.g., colors, flows/segment, total segments, and total flows) that may be used to achieve a relatively large combination space (codespace) from which to select a subset of codes.

FIG. 39 is a schematic diagram of an example of a trellis code and a process of using the trellis code to select a set of codes with desired properties for an assay from a large code space.

FIG. 40B shows examples of excluded sequences and temperature parameters for the strategy for designing oligo segments on a probe of FIG. 40A.

FIG. 41 discloses SEQ ID NOS 4-8 respectively, in order of appearance.

FIG. 43 is a summary of a channel model for a base calling algorithm that may be used in a soft decoding process.

SUMMARY OF THE INVENTION

Figure 1:
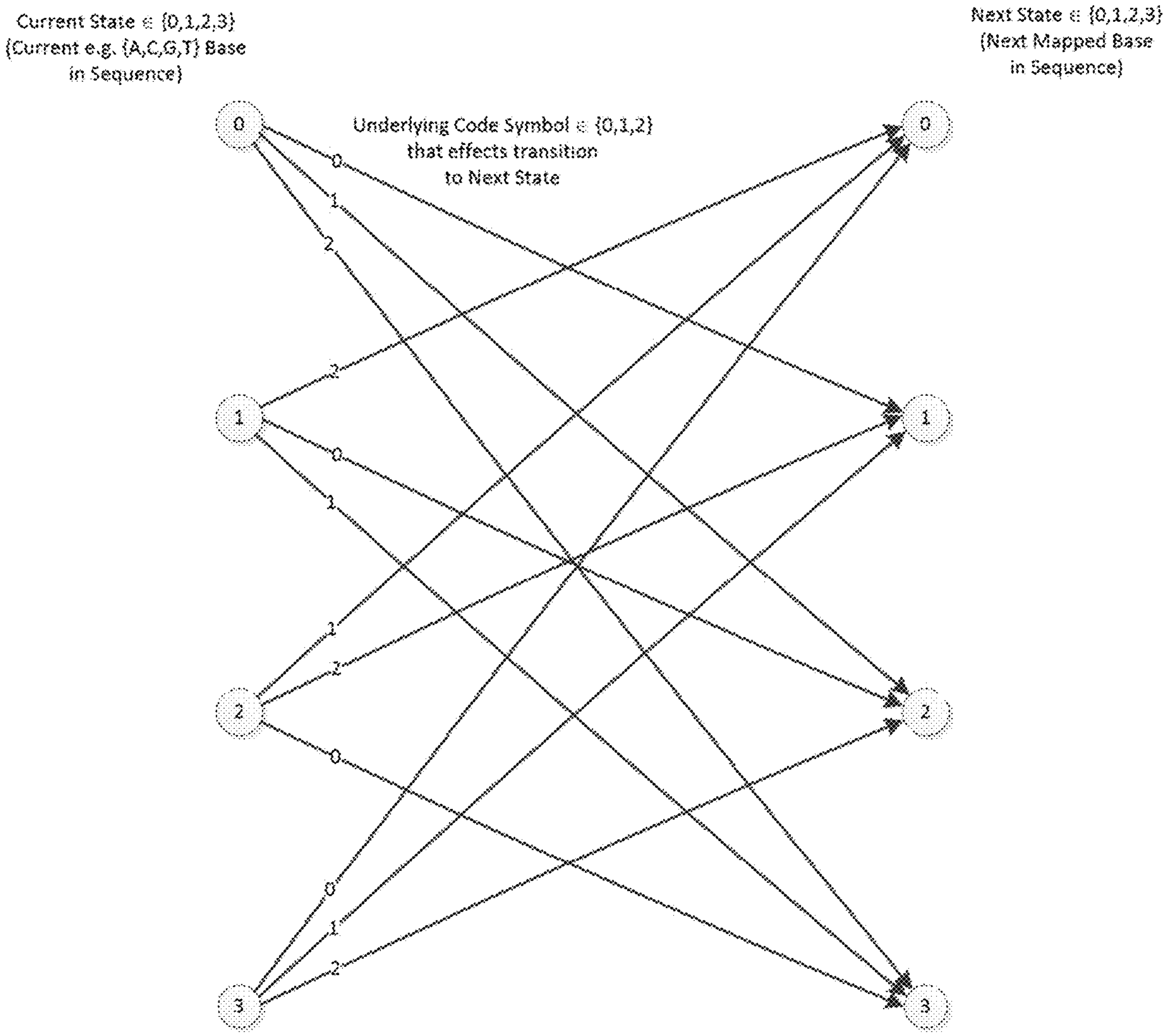
FIG. 1 is a diagram illustrating an encoding method that uses a 4-state encoding trellis with 3 transitions per state.

In various embodiments of the invention, a method is provided of conducting an assay for a set of targets, the method comprising: (a) subjecting a set of targets to a recognition event, in which each target is uniquely recognized by and bound to at least one recognition element from a set of coded recognition elements, each recognition element comprising a target-specific binding site and a code from a set of codes, each code comprises at least one segment encoding one or more symbols that correspond to a sequence of one or more nucleotides, to yield a set of coded targets comprising the target and recognition element; (b) subjecting the recognition elements of the set of coded targets to a molecular transformation event to yield a set of modified recognition elements comprising the codes, such that the codes of the modified recognition elements can be amplified in an amplification event; and (c) performing the amplification event for each code of the modified recognition elements and detecting the targets associated with the set of modified recognition elements by decoding the codes that are amplified.

In other embodiments, a method is provided for conducting an assay for a set of targets. The method includes (a) subjecting a set of targets to a recognition event, in which each target is uniquely recognized by and bound to a recognition element comprising a code from a set of codes; (b) subjecting the recognition elements to a molecular transformation event to produce a set of modified recognition elements in the presence of the target and a set of unmodified recognition elements in the absence of the target, in which the codes of the modified recognition elements can be amplified and the codes of the unmodified recognition elements cannot be amplified in an amplification event; and (c) performing the amplification event on the transformed recognition elements and detecting the targets associated with the set of modified recognition elements by decoding the codes that are amplified. Each code may include at least one segment encoding one or more symbols that correspond to a sequence of one or more nucleotides.

In the methods of the invention, the codes may be soft decodable codes.

In some instances, the set of coded recognition elements may include at least 10, 100, 1,000, or 10,000 coded recognition elements and each of the coded recognition elements includes a soft decodable code.

Decoding the codes that are amplified in the methods of the invention may include: (a) recording signal produced in response to interrogation of each segment of the codes; and (b) upon completion of the interrogation, determining a probably of the presence of each of the codes by applying a soft-decision probabilistic decoding algorithm to the recorded signal, wherein the presence of the code is indicative of the presence of the target.

In various embodiments of the invention, the codes in the set of coded recognition elements are the same length. In other instances, at least a subset of the set of coded recognition elements has codes of the same length.

In some embodiments of the methods of the invention, the set of coded recognition elements consists of tens, hundreds, thousands, or up to tens of thousands of the coded recognition elements, decoding the codes that are amplified includes decoding the codes by a soft decoding method, and the codes are trellis codes and at least a subset of the trellis codes has the same length.

In some instances, a method is provided for conducting an assay for a set of target analytes that includes: (a) performing a recognition and amplification event on a set of coded target analytes potentially present in a sample to generate a set of rolling circle amplification products (RCPs) from the target analytes or representative of the target analytes present in the sample, wherein each of the coded RCPs comprises multiple copies of a nucleic acid code from a set of codes, wherein each code comprises at least one segment encoding one or more symbols that correspond to a sequence of one or more nucleotides; (b) recording signal produced in response to interrogation of each segment of the codes; and (c) upon completion of the interrogation, determining a probably of the presence of each of the codes by applying a soft-decision probabilistic decoding algorithm to the recorded signal, wherein the presence of the code is indicative of the presence of the target analyte.

The set of coded RCPs may include at least 10, 100, 1,000, or 10,000 coded RCPs and each of the coded RCPs may include a soft decodable code.

In the methods of the invention, decoding the codes that are amplified or interrogation of the segments can include one or a combination of nanopore sequencing, next-generation sequencing, massively parallel sequencing, Sanger sequencing, sequencing by synthesis (SBS), pyrosequencing, sequencing by hybridization, decoding by hybridization, single molecule real-time sequencing, SOLiD, and sequencing by ligation.

Each segment of the codes of the invention may include one symbol corresponding to one nucleotide. Each of the codes may include up to 50 segments for a length of each code comprising up to 50 nucleotides. Interrogation of the up to 50 segments having one symbol corresponding to one nucleotide sequencing may be performed by sequencing by synthesis (SBS).

In other embodiments, each segment may include one symbol corresponding to more than one nucleotide.

In various instances, each code may include two or more segments. Each code may include three or more segments. Each code may include four or more segments. In some cases, each code includes five to sixteen segments.

In one embodiment, interrogation of the segments including one symbol corresponding to more than one nucleotide is performed by decoding by hybridization. In some instances, at least one of the segments is interrogated more than one time by hybridization with one or more hybridization probes each having at least one label to produce the signal. At least four different labels may be utilized in the decoding by hybridization. In one example, each code includes at least four segments and at least sixteen symbols. In the case that at least one of the segments is interrogated more than one time by hybridization with one or more hybridization probes each having at least one label to produce the signal, a unique number of possibilities at each of the segments includes up to a number of the different labels to the power of a number of the hybridizations per segment. The label may be an optical label. The label may be a fluorescent label. At least one probe may include two or more of the labels to create a pseudo label and generate a larger number of the symbols.

In the methods of the invention, the set of targets may include tens of target analytes, hundreds of target analytes, thousands of target analytes, or tens of thousands of target analytes.

The set of targets may be nucleic acid targets, polypeptide targets, or both nucleic acid and polypeptide targets.

In the various embodiments of the invention, at least one of the following I, II or III may be true: (I)(A) the set of targets is immobilized on a surface; or (I)(B) the recognition element in the recognition event is immobilized on a surface; (II) the amplification event is performed on a surface; or (III) the amplification event and the recognition event are performed on the same surface.

In some instances, the set of rolling circle amplification products generated in the amplification event are attached non-covalently to a charged surface. The surface may be a cation-coated surface. The surface may be a polylysine coated surface.

In various embodiments, encoded probes, sets of encoded probes, and compositions including the sets of encoded probes are provided.

In one instance, a set of coded oligonucleotide probes is provided, each probe including a target-specific binding site and a code from a set of codes. In this instance, each code is a soft decodable code that includes at least one segment encoding one or more symbols that correspond to a sequence of one or more nucleotides.

The set of coded oligonucleotide probes may include padlock probes.

The set of coded oligonucleotide probes may include at least 10, 100, 1,000, or 10,000 probes.

DETAILED DESCRIPTION OF THE INVENTION

Terminology

"A," "an" and "the" include their plural forms unless the context clearly dictates otherwise.

"About" means approximately, roughly, around, or in the region of. When "about" is used with a numerical range, it modifies that range by extending the boundaries above and below the numerical values indicated. "About" can modify a numerical value above and below the stated value by a variance of, e.g., 10 percent up or down (higher or lower).

"And" is used interchangeably with "or" unless expressly stated otherwise.

"Include," "including," and the like are to be construed in an inclusive sense as opposed to an exclusive or exhaustive sense; that is to say, in the sense of "including, but not limited to."

"Invention," "the invention" and the like are intended to refer to various embodiments or aspects of subject matter disclosed herein and are not intended to limit the invention to the specific embodiments or aspects of the invention referred to.

The terms "coded" and "encoded" are intended to have the same meaning and are herein used interchangeably.

"Linked" with respect to two nucleic acids means not only a fusion of a first moiety to a second moiety at the C-terminus or the N-terminus, but also includes insertion of the first moiety to the second moiety into a common nucleic acid. Thus, for example, the nucleic acid A may be linked directly to nucleic acid B such that A is adjacent to B (-A-B-), but nucleic acid A may be linked indirectly to nucleic acid B, by intervening nucleotide or nucleotide sequence C between A and B (e.g., -A-C-B- or -B-C-A-). The term "linked" is intended to encompass these various possibilities.

"Optimum," "optimal," "optimize" and the like are not intended to limit the invention to the absolute optimum state of the aspect or characteristic being optimized but will include improved but less than optimum states.

The terms "rolling circle amplification products (RCPs)" and "nanoballs" are intended to have the same meaning and are herein used interchangeably.

"Sample" means a source of target or analyte. Examples of samples include biological samples, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Samples may be from any organism (e.g., prokaryotes, eukaryotes, plants, animals, humans) or other sample (e.g., environmental or forensic samples).

"Set" includes sets of one or more elements or objects. A "subset" of a set includes any number elements or objects from the set, from one up to all of the elements of the set.

"Subject" includes any plant or animal, including without limitation, humans.

"Target" means a nucleic acid analyte (e.g., mRNA, cfDNA etc.) or a proxy for the target analyte of interest (e.g., an antibody conjugated with oligonucleotide). Thus, in some instances, the term "target" and the term "target analyte" are used interchangeably. "Target" with respect to a nucleic acid includes wild-type and mutated nucleic acid sequences, including for example, point mutations (e.g., substitutions, insertions and deletions), chromosomal mutations (e.g., inversions, deletions, duplications), and copy number variations (e.g., gene amplifications). "Target" with respect to a nucleic acid may also include the presence or absence of one or more methyl groups on the nucleic acid target. "Target" with respect to a polypeptide includes wild-type and mutated polypeptides of any length, including proteins and peptides."

"Decoding" with respect to a code includes determining the presence of a known code or a probability of the presence of a known code with or without determining the sequence of the code. Decoding may be hard decision decoding. Decoding may be soft decision decoding.

"Identify," "determine" and the like with respect to codes, targets or analytes of the invention are intended to include any or all of: (A) an indication of the presence or absence of the relevant code, target or analyte, (B) an indication of the probability of the presence or absence of the relevant code, target or analyte, and/or (C) quantification of the relevant code, target or analyte.

"Hard decision decoding" or "hard decision" refers to a method or model that includes making a call for each nucleotide in a nucleic acid segment (commonly referred to as a "base call") in order to identify nucleotides in the nucleic acid segment. Models of the invention incorporate hard decision decoding models. The particular nucleic acid being decoded may be or include a code of the invention.

"Soft decision decoding" or "soft decision" refers to a method or a model that uses data collected during a sequencing or decoding process to calculate a probability that a particular nucleic acid or nucleic acid segment is present. The probability may optionally be calculated without making a base call for each nucleotide in a nucleic acid segment. In another example, a probability is calculated without making a hard call that a string of nucleic acids in a segment are present. Instead of making a hard call for each nucleotide or nucleotide segment, a probabilistic decoding algorithm is applied to the recorded signal upon completion of signal collection. A probability of the presence of each of the codes may be determined without discarding signal in contrast to hard decision decoding method in which hard calls are made during the signal collection process. In soft decision decoding, the data may, for example, include or be calculated from, intensity readings in spectral bands for signals produced by the sequencing/decoding chemistry. In one embodiment, soft decision decoding uses data collected during a sequencing/decoding process to calculate a probability that a particular nucleic acid segment from a known set of sequences is present. Models of the invention may be used for soft decision decoding. The particular nucleic acid or nucleic acid segment being decoded may be or include a code of the invention.

"Phasing" or "signal phasing" means misalignment of SBS cycles during an SBS process caused by the non-incorporation of a nucleotide during a cycle or by the incorporation of two or more nucleotides during an SBS cycle.

"Droop" or "signal droop" means signal decay that occurs during an SBS process, which may be caused by some complementary strands being synthesized as part of the SBS process being blocked, preventing further nucleotide incorporation.

"Sample" means a set of nucleic acids for testing. A sample preparation process may be used to produce a sequencing-ready sample from a raw sample or partially processed sample. Note that one or more samples may be combined for sample preparation and/or sequencing and may be distinguished post-sequencing using sample-specific DNA barcodes linked to sample fragments.

"Crosstalk" refers to the situation in which a signal from one nucleotide addition reaction may be picked up by multiple channels (referred to as "color crosstalk") or the situation in which a signal from a nanoball or sequencing cluster interferes with an adjacent or nearby cluster or nanoball (referred to as "cluster crosstalk" or "nanoball crosstalk").

"Color channel" means a set of optical elements for sensing and recording an electromagnetic signal from a sequencing reaction. Examples of optical elements include lenses, filters, mirrors, and cameras.

"Spectral band" or "spectral region" means a continuous wavelength range in the electromagnetic spectrum.

Headings are included herein for reference and to aid in locating the various sections. These headings are not intended to limit the scope of the concepts described with respect to the headings.

The description and examples should not be construed as limiting the scope of the invention to the embodiments and examples described herein, but as encompassing all modifications and alternatives falling within the true scope and spirit of the invention.

Encoded Assays

The disclosure provides encoded assays for detection of target analytes in a sample. At a high level, in an encoded assay, a target analyte ("target") is detected based on association of the target with a code and detection of the code is a surrogate for detection of the analyte.

In various embodiments, an encoded assay may include a recognition event in which a target is uniquely recognized by a recognition element. The recognition event may be effected by submitting targets of a set of targets to a recognition event, in which each target is uniquely recognized by and bound to a recognition element associated with a code, thereby yielding a set of coded targets comprising the target and the recognition element.

In various embodiments, an encoded assay may include a transformation event, in which a high-fidelity molecular transformation of the recognition element associated with a code produces a modified recognition element. The transformation event may be effected by submitting each recognition element of the set of coded targets to a transformation event, in which a molecular transformation of each recognition element produces a modified recognition element, thereby yielding a set of modified recognition elements comprising the code.

In various embodiments, an encoded assay may include a detection event, which detects the code as a surrogate for detection of the analyte, e.g., by decoding, the code, such as by recognizing or decoding code (and optionally other elements). The detection event may include an amplification step in which each code of the set of modified recognition elements is amplified, thereby yielding a set of amplified codes. Amplified codes of the set of amplified codes may have their sequences determined or decoded using a variety of techniques, including for example, but not limited to, microarray detection, or nucleic acid sequencing. In some cases, the detection step may be integrated with the amplification step, e.g., as in amplification with intercalating dyes.

In one embodiment, the method may include:

(i) submitting each target of a set of targets to a recognition event, in which each target is uniquely recognized by and bound to a recognition element associated with a code, thereby yielding a set of coded targets comprising the target and the recognition element;

(ii) submitting each recognition element of the set of coded targets to a transformation event, in which a molecular transformation of each recognition element produces a modified recognition element, thereby yielding a set of modified recognition elements comprising the code;

(iii) submitting each code of the set of modified recognition elements to an amplifying event, in which each code is amplified, thereby yielding a set of amplified codes;

(iv) submitting each amplified code of the set of amplified codes to a detection event, thereby decoding the code.

In one embodiment, the method may include:

(i) a recognition event in which the target is uniquely recognized by a recognition element, which associates a code (and optionally other elements) with the target via the recognition element;

(ii) a transformation event, in which a high-fidelity molecular transformation of the recognition element produces a modified recognition element that produces a readable code;

(iii) a detection event, which detects the code as a surrogate for detection of the analyte, e.g., by recognizing or decoding code (and optionally other elements).

As described in more detail herein, the recognition event, transformation event, and the detection event may occur sequentially, or combinations of the steps may occur simultaneously, e.g., as a single combined step. For example, the transformation event and the coding event may be simultaneous, such that the sequential process involves (i) recognition event, followed by (ii) transformation event/coding event, followed by (iii) detection event.

To further illustrate the encoded assays:

(i) In the recognition event, the target may be detected by a targeted molecular binding event, such as binding of the target by a complementary sequence or a polypeptide binder.

(ii) In the transformation event, a ligation or a gap-fill ligation may produce the modified recognition element, i.e., a version of the recognition element that is ligated or gap-fill ligated.

(iii) In the coding event, a code reagent may be associated with the modified recognition element based on recognition of the modified recognition element. For example, the novel coded padlock probes of the invention may be configured with a sequence that recognizes the modified recognition element and may circularize only if the modified recognition element is present.

(iv) In the detection event, the reading of the code may involve any means of decoding the code (and optionally other elements).

The codes may be error corrected and thus easy to distinguish from each other, so they can be detected a low abundance and in the presence of high level of background and in the presence of many other codes.

Since many assays can be converted into codes, the invention provides for multiomic assays where a sample is analyzed in multiple parallel workflows that are analyte-dependent and then converge codes that can be then detected simultaneously in a single platform. Parallel assay workflows may be merged into a single workflow, where multiple targets and target-types (e.g., nucleic acids and polypeptides) may be detected simultaneously in a single workflow and also read simultaneously within the same readout platform.

Following recognition and transformation, the codes may be detected and matched to targets for identification and/or quantification of targets present in the sample.

Code Design and Decode

The encoded assays of the invention make use of codewords or codes. The codes may be detected as surrogates in the place of direct analysis of target analytes. As an example, a target analyte may be a particular nucleic acid fragment (e.g., a nucleic acid fragment with a specific mutation); in the assays of the invention, a codeword may be associated with the nucleic acid fragment and the codeword may be read to identify the presence of the nucleic acid fragment in the sample.

For example, a code may be a predetermined sequence ranging from about 3 to about 100 nucleotides or about 3 to about 75 nucleotides. Codes may have sequences selected to avoid inadvertent interaction with other assay components, such as targets, probes, or primers. Code sequences may be selected to ensure that codes differ from each other to permit unique identifiability during the decoding process.

The invention includes a dataset or database of codes generated using the methods of the invention. The dataset or database may associate the codes with other assay elements, such as primers or probes linked to the probes. The invention also includes a method of making a probe set comprising synthesizing probes having the sequences set forth in the dataset or database.

Homopolymer-Free Encoding

In one embodiment, the codes are homopolymer-free codes. For standard genomic applications that use a full 4-ary nucleotide alphabet of {ACGT}, the method uses a 4-state encoding trellis with 3 transitions per state.

As illustrated in FIG. 1, the current state is the last mapped nucleotide, and the next state is the next (to-be) mapped nucleotide. By forbidding a transition from the current state (say, the 'A' state) in the present trellis section (of 4 states), to the analogous same state (of 'A') in the next trellis section (of 4 states), a repeated mapping to the same nucleotide base—in any generated sequence—is avoided. An 'A' state can only transition to a 'C', 'G', or 'T' state in the next trellis section. Since this involves 3 transitions per state, the mapping trellis is mated to an underlying 3-ary (i.e., ternary-) alphabet error correction code that drives transitions through trellis sections. The underlying (ternary) error correction code is the mechanism that guarantees all generated codewords differ in multiple sequence positions. A similar method may apply to 3-ary alphabets (where only 3 of the four nucleotide bases, say {CGT} are used), and 5-ary or higher alphabets, where the underlying correction code uses an alphabet of order one less than the mapping alphabet.

In one embodiment, codes for the set of codes are selected using a 4-ary alphabet, avoid homopolymers, and every code in the set is different from every other code in the set. The codes may be generated using the trellis method.

In one embodiment, codes for the set of codes are selected using a 3-ary alphabet, avoid homopolymers, and every code in the set is different from every other code in the set. The codes may be generated using the trellis method.

(i) In another embodiment, a homopolymer-free code composed from a 4-ary nucleotide alphabet of {ACGT} may be generated as follows:
(ii) From GF(4) (i.e., the quaternary algebraic alphabet), select an error correction code that will deliver many more codewords than necessary (because some of the generated codewords will later be eliminated);
(iii) Generate all of the codewords for the code;
(iv) Assess the number of repeated symbol locations in each codeword;
(v) Re-order the list of codewords, sorting by the number of base-repeat instances in each codeword.
(vi) From the re-ordered sort, keep only the top K codewords, where K is the desired library size of codewords (this will eliminate the codes with the highest number of polymer-repeats; each repeat will require subsequent fixing that weakens the overall code.)
(vii) For each codeword in the list of survivors, 'smart fix' the repeat positions in each codeword with the following procedure:
  a. Start from the beginning base position in a codeword, and find the first repeat instance of a base;
  b. Go to the second base in the first repeat instance, its base assignment will require change;
  c. If the second base is not at the end of a codeword, look ahead one base position in the codeword, and assess the assignment there;
  d. For the second base (in the repeat), choose a new base assignment that is also different from the base assigned one sample ahead; n that, in addition to removing a length-2 run, this step will also fix a length-3 run;
  e. Process the revised codeword at each remaining repeat location, fixing the second base in each repeat using the process outlined in steps c-d.

This method will eliminate all repeats. The same method can be applied to generate homopolymer codes for 3-ary alphabets (eg., {C, G, T}), and larger 5-ary+ alphabets (such as oligopolymers).

Codes may be optimized for pyrosequencing and similar cyclic serial dispensation schemes. In one embodiment, the invention provides a locus code-encoding approach for pyrosequencing or similar serial (rather than pooled) primer dispensation methods. The method generates homopolymer-free codes.

When the locus code is encapsulated between header and tail bases, all generated codewords finish decoding at the same time. The technique avoids unexpected spurious incorporations that change how long in time that a codeword needs to finish its decoding. This is important because then a sequencer only need sample for a prescribed number of samples to obtain complete data for decoding the samples, regardless of the underlying codeword. This also keeps all codewords candidates aligned, so that the theoretical design distances between codewords are maintained.

The previously mentioned synchrony ensures that soft decision block decoding techniques can be applied during the decoding of its blocks of samples. This soft decision decoding guarantees that SNR requirements are improved by at least 2 dB—and sometimes by many factors—more when the signal strength significantly fades during the reception of codeword samples.

In pyrosequencing, nucleotides are dispensed sequentially (and non-overlappingly) in a cycle, such as G, C, T, A, G, C, T, A, G, C, . . . etc. This encoding is quite original because it doesn't directly encode bases; instead, it encodes base positions within G, C, T, A cycles. Each cycle element can be either populated, or unpopulated—and multiple elements within a cycle can be populated. For this to be implemented, the underlying code must be derived from a binary alphabet, with 1s and 0s. To emphasize, with these codes, more than one base can be incorporated within a single G, C, T, A dispensation cycle. This also implies that sequencing, though serial in nature, can be fast. And with the underlying {0,1} alphabet that underpins and drives the encoding of the populated/unpopulated cycle positions, all codewords are guaranteed to be of the same length—and to finish decoding in the same amount of time.

To provide coding gain, the sequence of 0s and 1s that comprise each codeword are derived from constructions of optimal binary error correction codes. Such codes possess many redundant parity bits, and these parity bits are designed such that each codeword varies from each other in multiple positions. This quality results in strong error correction capabilities.

Figure 2:
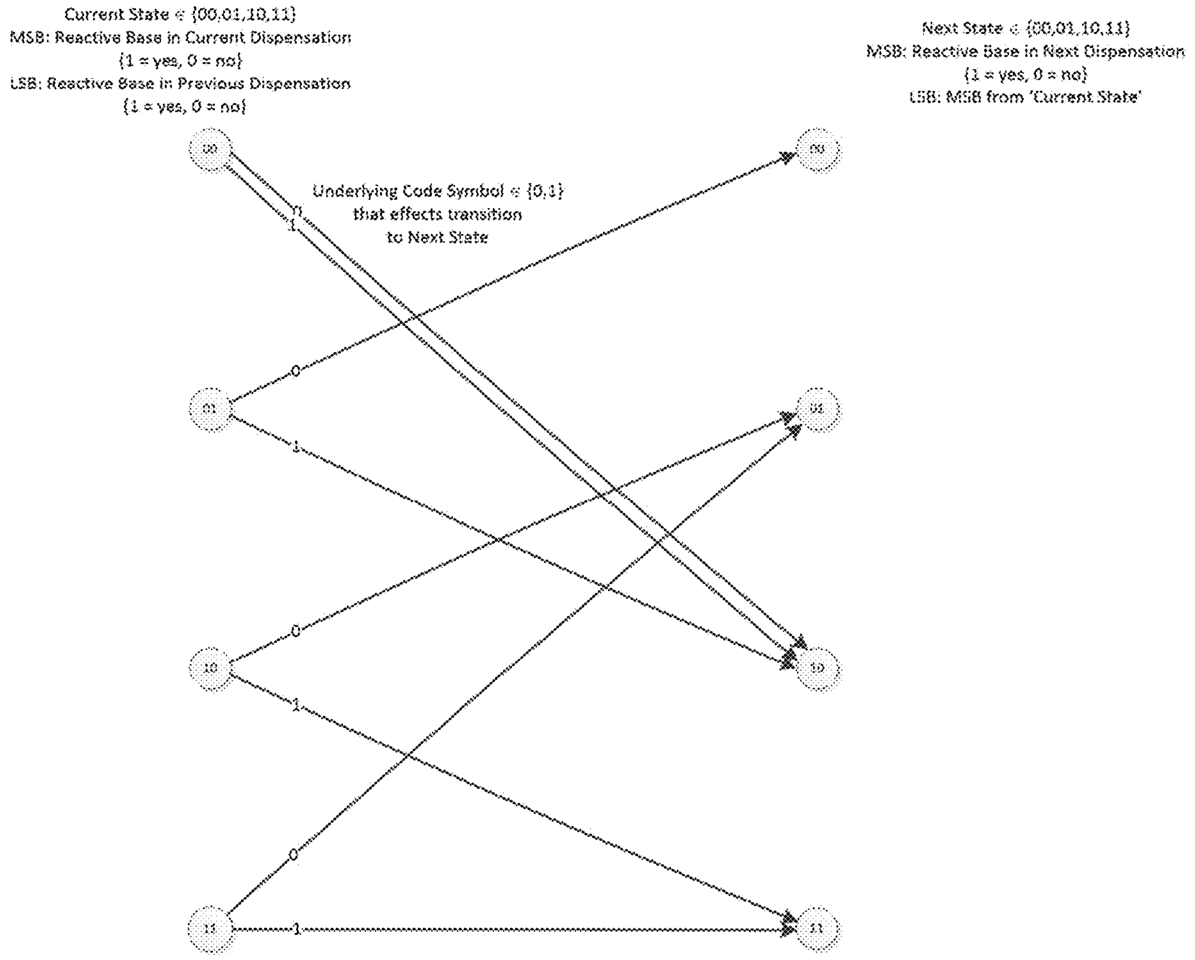
FIG. 2 is a diagram illustrating an encoding trellis for a 4-bases-per-cycle pyrosequencing.

FIG. 2 illustrates an encoding trellis for a 4-bases-per-cycle pyrosequencing. The techniques may be used for encoding 3-cycle, 3-base-alphabet, and 5+-cycle, 5-and-higher-alphabet oligo-polymer hybrid schemes.

Note the use of 4 states in the trellis. Each state represents previous mappings of that last two positions:

(i) both unpopulated, (00);

(ii) both populated, (11);

(iii) newest-populated and older-unpopulated, (10);

(iv) newest-unpopulated and the older populated, (01).

Transitions to next states indicate an update which either does not populate or does populate the next position in a sequence.

Four (4) states are used to correctly implement a pyrosequencing scheme that is homopolymer-free; one position is populated every 3 positions. Note that if 3 consecutive positions were allowed to be unfilled, then the $4^{th}$ position would need to be filled (because an unzipped hybrid will have an opening to at least one of the four nucleotides). That $4^{th}$ position being filled would result in generation of a homopolymer (repeat) of bases in a sequence—since the last filled base was the same base in the cycle before.

This aforementioned restriction explains the double transition from the 00 state to the 10 state in the trellis diagram. A current state of 00 transitioning to a next state of 00 would imply 3 positions in a row were unfilled.

Optimal error correction codes are constructed to maximize distance between their sets of codewords. They are not constrained to disallow runs of three consecutive zeros. That would reduce the degrees of freedom they use to maximize distance. By contrast, the mappings to pyrosequenced positions comply with homopolymer-free and pyrosequencing constraints.

All other transitions in the picture design trellis are natural results of populating a position with a '0' or a '1' and updating the next state to reflect that transition. Since 7 of the 8 transitions in the trellis perfectly express the underlying error correction code's structure, such a code can be quite effective and powerful.

Weakening transitions occur when the underlying code has 3 consecutive zeros. One way to reduce those appearances is to use the sorting methodology described above. This method modestly reduces the library of codes. This method also ensures that the pyro-mapped codewords that best reflect the underlying binary code's structure are faithfully reproduced, while those least reflective are not.

Another method to improve the weakening due to transitions involves breaking up strings of zeros by interleaving the code. Within a code, the (systematic) information section of bits—which precede the redundant section of parity bits—are the bits where the most consecutive zeros are usually seen. One way to eliminate those strings of zeros is to interleave the entire code design, so that the parity and information bits are intermingled. All codewords may be intermingled by the same interleaving pattern. The interleaving technique does not help for the all-zeros codeword, which is generated by almost all linear codes. The all-zeros codeword can be excluded from the codeword set.

Figure 3:
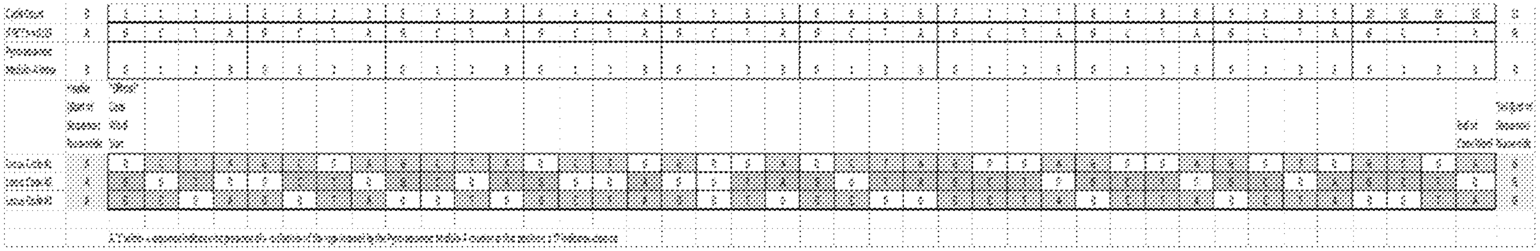
FIG. 3 is a diagram illustrating a pyro-code example, followed by a snapshot from a spreadsheet with relevant parameters.

FIG. 3 shows a pyro-code example, followed by a snapshot from a spreadsheet with relevant parameters. The code is a 10-cycle, 40 position code that maps {GCTA} in cycles. It possesses a huge minimum distance between codewords and is an example code accommodating three codewords. Note that the number of bases assigned to each codeword is not the same, although, clearly, from the illustration, all codewords are of the same time duration, and would finish decoding at the same time. Also observe the usage of populated 'header' and 'tail' positions. These are used to encapsulate the codeword and ensure that it is homopolymer free throughout. These terminating positions may be butted-up against the ends of the codewords for effective encapsulation.

For the purposes of the specification and claims, the codes of the invention that are based on an encoding trellis as illustrated in FIG. 1, FIG. 2, and FIG. 3 can be referred to herein as "trellis codes".

Amplifying and Reading Codes

In an encoded assay, a target is detected based on association of the target with a code, and detection of the code is used as a surrogate for detection of the analyte. A variety of techniques may be used to amplify and read the codes.

In one embodiment, codes of the invention are amplified using rolling circle amplification (RCA) to produce DNA nanoballs that include many duplicates of the code. An RCA reaction may include one or more rounds of amplification to produce the nanoball product. A nanoball may be from about 10,000 to about 1,000,000 or more nucleotides in length. A nanoball may include from about 100 to about 10,000 or more copies of the amplified code.

In one embodiment, the codes of the invention are amplified using a linear PCR amplification reaction to generate double stranded DNA amplicon products.

In one embodiment, codes of the invention are amplified using bridge amplification to produce clusters of oligos on a surface.

In one embodiment, codes of the invention are amplified on bead surfaces to produce bead-attached oligos.

In one embodiment, the amplified codes are read in a sequencing reaction.

In one embodiment, codes of the invention are detected using a patterned array, such as a microarray comprising oligos which are complimentary to the codes.

In one embodiment, codes of the invention are detected in situ, i.e., in a cell or tissue.

In one embodiment, in situ detection comprises reading the code in a sequencing reaction.

In one embodiment, codes of the invention are detected using an electronic/electrical sensing mechanism.

A variety of techniques and models may be used to identify a nucleic acid code of the invention. In one embodiment, the invention provides models that make use of hard decision decoding methods or models. In another embodiment, the invention provides models that make use of soft decision decoding methods or models.

When using soft decision decoding techniques, it is not necessary for the model to identify each base specifically. For example, signals generated during each nucleotide addition cycle of a sequencing process may be detected and recorded to produce a data set that may be used as input into a model of the invention to calculate a probability that a specific code is present without requiring a hard decoding model. Although it is not necessary in a soft decision decoding model to make a hard decision about the identity of each nucleotide, a model developed according to the methods of the invention may nevertheless include a model for assigning a probability or identity to each nucleotide in the sequence of a code.

Data gathered during a sequencing process may, for example, include intensity readings for signals produced by the sequencing chemistry in various spectral bands. For example, in some cases the data is collected across a set of spectral bands that corresponds to part or all of the spectral bands expected to be produced by a series of nucleotide extension steps during a sequencing process.

In some embodiments, it is not necessary to filter light from each nucleotide extension step in order to distinguish between the nucleotides. Instead, a set of intensity readings may be detected, stored and used as input into a model of the invention for determining a probability that a particular code is present. In other embodiments, one or more filters may be used to refine signals from a sequencing process.

A model may be developed or trained using sequencing data from known codes, such as signal intensity data across a predetermined spectrum, during a sequencing process. The model may be used to calculate a set of probabilities across a set of one or more codes, indicating, for example, for each code, a probability that it is present in a sample.

In some cases, the model is developed or trained using data corresponding to color intensity signals across multiple color channels. In some cases, the model is developed or trained using data corresponding to color intensity signals across four color channels, each generally corresponding to the signal produced by addition of one of the four nucleotides A, T, C or G during a sequencing process. As discussed elsewhere in this specification, the channels may experience color crosstalk.

A model may be built using data obtained using multiple light sensing channels. Each channel may be specific for a specific frequency bandwidth. In some cases, the model may be built using four channels, wherein the bandwidth of each channel may be selected for signals produced by addition of one of the four nucleotides A, T, C or G. In other cases, more or less than four channels may be used to collect data used to produce the model.

Figure 4:
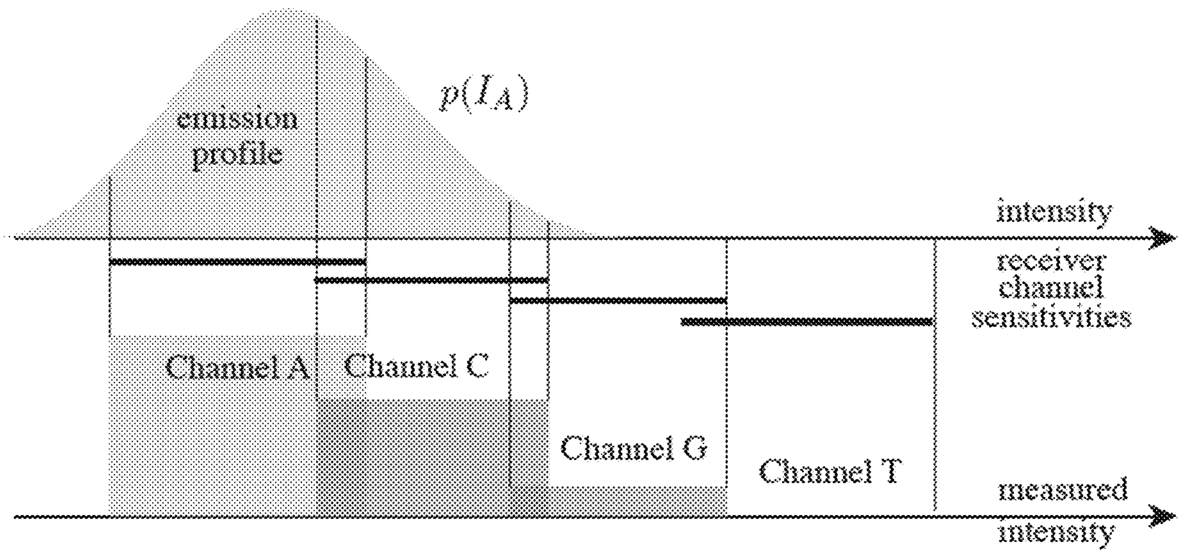
FIG. 4 shows a hypothetical emission spectrum, which is detected at varying intensities by Channel A, Channel C and Channel G, and not detected by Channel T.

In certain embodiments of the invention, each channel detects a bandwidth region of a fluorescence signal produced by addition of one of the four nucleotides. Nevertheless, the bandwidth of the signal produced by addition of one of the four nucleotides may be spread across a spectral band that overlaps with other channels. This effect is illustrated in FIG. 4. FIG. 4 shows a hypothetical emission spectrum, which is detected at varying intensities by Channel A, Channel C and Channel G, and not detected by Channel T.

As will be discussed in the examples below, a color crosstalk model may be empirically developed and used as input into the model of the invention for producing a probability that a code is present. Relative coefficient strength may be experimentally determined across color channels for signal produced by addition of each nucleotide (A, T, C, G) from empirically produced test data.

Other factors that may be included in a statistical model according to the invention for calculating a probability that a code is present include signal phasing, signal droop, color cross-talk values, fluctuations in in color cross-talk values, noise, amplitude noise, gaussian amplitude models, and base calling algorithms.

The model of the invention may also account for various sources of noise and error, such as variability in the concentration of the active molecules in the assay, variability in color channel response due primarily to limited ability to estimate the color channel responses individually for each cluster, and background and random error noise sources. A concentration noise model may be used to model the variable density of active molecules for a given cluster. A transduction noise model may be included to model variability in the color crosstalk matrix.

Accurately modeling the biochemical opto-mechanical processes in DNA sequencing is a complex process. Furthermore, to derive the inputs for a soft decision probabilistic signal estimator requires estimating the parameters driving the model, as well as having strong confidence that the model is accurate. Under these two assumptions, metrics can be computed that work directly with the received signals. In the commercially available base call algorithms, channel distortion effects are compensated for before the decision process; however, in soft decision decoding of the invention it is not necessary to compensate for distortions before decoding. Embodiments which do not compensate for distortions before decoding will have the advantage of avoiding information loss compensations, such as inversions.

The probability that a particular code is present may be indicative of the probability that a particular target associated with the probe is present. Data indicating the probability that a particular target is present may be used, for example, to calculate probabilities relevant to diagnosis or screening of various medical conditions, or selection of drugs for treatment of various medical conditions.

The disclosure provides encoded probes that can be decoding using soft decision decoding methods or models. The codes may be generated using the trellis method and the codes may be referred to as "trellis codes". The probes of the invention may be padlock probes that include a soft decodable code, such as a trellis code. The probes of the invention may be a dual probe that includes a soft decodable code, such as a trellis code.

The disclosure provides assays that make use of encoded probes that may be decoded using soft decision decoding ("soft decoding"). In various embodiments, the assays make use of mixtures of probes, each with a soft decodable code. A mixture may include 100s, 1000s, 10000s, 100000s or more of encoded probes.

In some instances of the methods of the invention, decoding code is performed without making a specific base call for each nucleotide in the code.

In some embodiments, a hybridization-based detection method may be used to decode the code. In one embodiment, the amplified codes are identified using oligonucleotide probes in a hybridization-based reaction. The amplified codes may be identified using decoding by hybridization. In one example, the hybridization-based detection method uses fluorescently labeled oligonucleotide probes. The code data may then be used as a digital count of the target-specific detection events.

Assays

The encoded assays make use of recognition elements and encoded probe sequences ("encoded probes") for detecting a panel of target analytes ("targets").

An assay using encoded probes (i.e., an encoded assay) may include: (i) a recognition event, in which a target is uniquely recognized and bound by a recognition element associated with a code (i.e., an encoded probe); (ii) a transformation event, in which a molecular transformation of the recognition element produces a modified recognition element comprising the code that may be used to provide a measure of the presence or absence of the target; and (iii) a detection event, that uses the code as a surrogate for detection of the target, e.g., by recognizing or decoding code (and optionally other elements).

An encoded assay may be a solution-based assay.

An encoded assay may be a surface-bound assay, e.g., on a flow cell or on beads.

An encoded assay may be a hybrid assay that includes a surface-bound component and a solution-based component.

An encoded assay maybe performed in a plate-based format (e.g., a multi-well plate). The multi-well plate may include, for example, an array of nanowells.

An encoded assay may be performed on a microfluidics device.

The encoded probe may include other functional sequences such as sequencing primers, one or more amplification primer sequences, unique identifier sequences (UMIs) and sample indexes. The sequencing primers may, in some cases, be adjacent to the code sequence. The amplification primer sequences may, in some cases, be universal primer sequences that are common to all probes in a set of encoded probes.

An encoded probe may be a padlock probe that includes a recognition element associated with a code. The code may be a soft decodable code, such as a trellis code.

Thus, for example, the disclosure provides a padlock probe in which the terminal sequences comprise a probe and a soft decodable code is provided between the terminal sequences. Similarly, the disclosure provides a padlock probe in which the terminal sequences comprise a probe and a trellis code is provided between the terminal sequences. The disclosure provides a set of 10 or more padlock probes in each of which (A) the terminal sequences comprise a probe and (B) a soft decodable code is provided between the terminal sequences. The disclosure provides a set of 100 or more padlock probes in each of which (A) the terminal sequences comprise a probe and (B) a soft decodable code is provided between the terminal sequences. The disclosure provides a set of 1000 or more padlock probes in each of which (A) the terminal sequences comprise a probe and (B) a soft decodable code is provided between the terminal sequences. The disclosure provides a set of 10,000 or more padlock probes in each of which (A) the terminal sequences comprise a probe and (B) a soft decodable code is provided between the terminal sequences. In certain embodiments, the foregoing sets are provided in the absence of any padlock probes that do not include the soft decodable codes. In certain embodiments, the foregoing sets are provided with codes that are homopolymer-free and soft decodable.

The disclosure provides a set of 10 or more padlock probes in each of which (A) the terminal sequences comprise a probe and (B) a trellis code is provided between the terminal sequences. The disclosure provides a set of 100 or more padlock probes in each of which (A) the terminal sequences comprise a probe and (B) a trellis code is provided between the terminal sequences. The disclosure provides a set of 1000 or more padlock probes in each of which (A) the terminal sequences comprise a probe and (B) a trellis code is provided between the terminal sequences. The disclosure provides a set of 10,000 or more padlock probes in each of which (A) the terminal sequences comprise a probe and (B) a trellis code is provided between the terminal sequences. In certain embodiments, the foregoing sets are provided in the absence of any padlock probes that do not include the trellis codes. In certain embodiments, the foregoing sets are provided with codes that are homopolymer-free trellis codes.

An encoded probe may be a molecular inversion probe that includes a recognition element associated with a code. The code may be a soft decodable code, such as a trellis code.

The disclosure provides a set of 10 or more molecular inversion probes in each of which (A) the terminal sequences comprise a probe and (B) a soft decodable code is provided between the terminal sequences. The disclosure provides a set of 100 or more molecular inversion probes in each of which (A) the terminal sequences comprise a probe and (B) a soft decodable code is provided between the terminal sequences. The disclosure provides a set of 1000 or more molecular inversion probes in each of which (A) the terminal sequences comprise a probe and (B) a soft decodable code is provided between the terminal sequences. The disclosure provides a set of 10,000 or more molecular inversion probes in each of which (A) the terminal sequences comprise a probe and (B) a soft decodable code is provided between the terminal sequences. In certain embodiments, the foregoing sets are provided in the absence of any molecular inversion probes that do not include the soft decodable codes. In certain embodiments, the foregoing sets are provided with codes that are homopolymer-free and soft decodable.

The disclosure provides a set of 10 or more molecular inversion probes in each of which (A) the terminal sequences comprise a probe and (B) a trellis code is provided between the terminal sequences. The disclosure provides a set of 100 or more molecular inversion probes in each of which (A) the terminal sequences comprise a probe and (B) a trellis code is provided between the terminal sequences. The disclosure provides a set of 1000 or more molecular inversion probes in each of which (A) the terminal sequences comprise a probe and (B) a trellis code is provided between the terminal sequences. The disclosure provides a set of 10,000 or more molecular inversion probes in each of which (A) the terminal sequences comprise a probe and (B) a trellis code is provided between the terminal sequences. In certain embodiments, the foregoing sets are provided in the absence of any molecular inversion probes that do not include the trellis codes. In certain embodiments, the foregoing sets are provided with codes that are homopolymer-free trellis codes.

The transformation event may include a ligation or gap-fill ligation reaction to produce the modified recognition element comprising the code.

The detection event may include an amplification step in which the code sequence (among other elements) is amplified. Amplification may be by any method of amplification, including for example, on-surface PCR, isothermal amplification, rolling circle amplification, and/or ultrarapid amplification. Surface based amplification may be performed using PCR with surface-anchored primers (e.g., Illumina bridge amplification technology) or recombinase polymerase amplification (RPA) (e.g., ExAmp technology).

In one embodiment, the amplification step comprises a rolling circle amplification (RCA) reaction to generate a nanoball product. In one embodiment, the amplification step comprises a rolling circle amplification (RCA) on an anionic surface to generate a nanoball product. In one embodiment, the amplification step comprises a rolling circle amplification (RCA) on a polylysine surface to generate a nanoball product. In one embodiment, the amplification step comprises a rolling circle amplification (RCA) on an anionic surface without covalently attaching the template to the surface to generate a nanoball product. In one embodiment, the amplification step comprises a rolling circle amplification (RCA) on a polylysine surface without covalently attaching the template to the surface to generate a nanoball product.

In one embodiment, an encoded probe may include a sequence which may prevent RCA of the probe, thereby allowing for production of linear double-stranded PCR products. The non-extendable sequence may, for example, be located between a pair of amplification primer sequences.

In one embodiment, an encoded probe may include a restriction enzyme site that may be cleaved to yield a linear DNA molecule.

Other Amplification Strategies

In some embodiments, the amplified code may be sequenced to identify the sequence of the code associated with the target. Any sequencing technology may be used to sequence. Examples of sequencing technologies that may be used include sequencing by synthesis (e.g., pyrosequencing; sequencing by reversible terminator chemistry (Illumina)), avidity sequencing (Element Biosciences), sequencing by hybridization, sequencing by ligation, and nanopore sequencing.

In some embodiments, a sequencing library may be generated from a set of modified recognition elements comprising the codes. The library may be sequenced to determine the code associated with a target of interest. The code data may then be used as a digital count of the target-specific detection events. In some embodiments the code is a soft-decodabe code.

In one embodiment, a sequencing library comprising the code (among other elements) may be generated from a circularized padlock probe.

In one embodiment, a sequence library comprising the code (among other elements) may be generated from a nanoball product.

In one embodiment, a nanoball or a portion of the nanoball that includes the code (and optionally other elements) may be directly sequenced to determine the code associated with the target of interest. The code data may then be used as a digital count of the target-specific detection events.

In some embodiments, a hybridization-based detection method may be used to decode the code. In one embodiment, the amplified codes are decoded using oligonucleotide probes in a hybridization-based reaction such as, for example, decoding by hybridization. In one example, the hybridization-based detection method uses fluorescently labeled oligonucleotide probes. The code data may then be used as a digital count of the target-specific detection events. Decoding using a hybridization approach may be soft decoding.

Coded Padlock Probes

The disclosure provides assays that make use of novel padlock probes comprising codes that may be used as a surrogate for detection of a target, e.g., by recognizing or decoding code (and optionally other elements). The code in a padlock probe may be a soft decodable code (e.g., a trellis code). A coded padlock probe may include target-specific regions that may be used for target recognition and enrichment. A coded padlock probe may include a 5' terminal phosphate that may be used to facilitate ligation (i.e., circularization) after target recognition. A coded padlock probe may include a 3' nucleotide that is the complement to a nucleotide at a target site of interest (e.g., a 3' SNP-specific nucleotide). A coded padlock probe may include an RCA priming site that includes a primer sequence suitable for priming an RCA reaction.

For example, the coded padlock probe may include regions at the 3' and 5' ends that are complementary to regions of a target. The probe regions may hybridize to the target, and the probe may be circularized, e.g., by a ligation or gap-fill ligation reaction. As described elsewhere in this disclosure, the target may be a nucleic acid analyte (e.g., mRNA, cfDNA etc.) or a proxy for the analyte of interest (e.g., an antibody conjugated with oligonucleotide).

Figure 5:
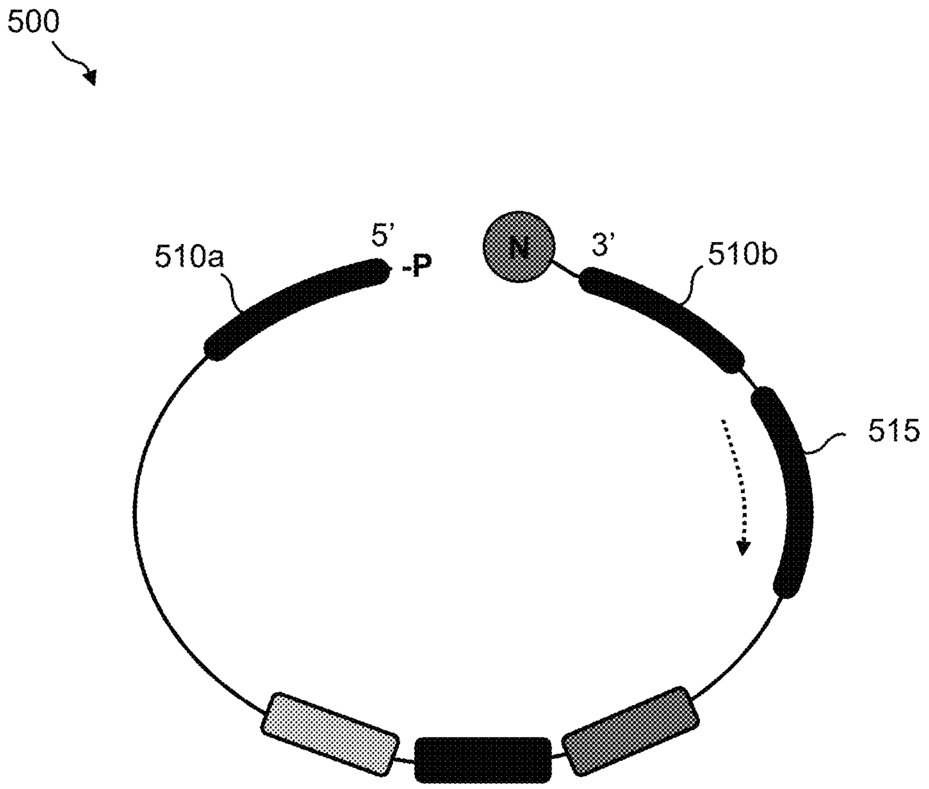
FIG. 5 is a schematic diagram of an example of a coded padlock probe.

FIG. 5 is a schematic diagram of an example of a coded padlock probe 500. Coded padlock probe 500 may include a 5' target specific region 510*a* and a 3' target specific region 510*b* that are complementary to regions of a target (not shown). The target may be a nucleic acid analyte (e.g., mRNA, cfDNA, etc.) or a proxy for the analyte of interest (e.g., an antibody conjugated with an oligonucleotide). Target specific region 510*a* may include a 5' terminal phosphate (P) that may be used to facilitate ligation (i.e., circularization) after target recognition. Target specific region 510*b* may include one or more terminal 3' nucleotides "N" complementary to a nucleotide at a target site of interest. In this example, the 3' target site specific nucleotide "N" may be a SNP specific nucleotide.

Target specific regions 510*a* and 510*b* may hybridize to the target, and the probe may be circularized. For example, when the complementary nucleotide is present in the target, the 3' SNP specific nucleotide hybridizes to the target, enabling circularization, e.g., by ligation or gap-fill ligation. Other types of features or mutations may be detected by varying the terminal nucleotide (N) or nucleotides of target specific region 510*a* and/or target specific regions 510*b* to hybridize when the target feature is present and not hybridize when the target feature is not present.

Coded padlock probe 500 may include an RCA priming site 515 that includes a primer sequence suitable for priming an RCA reaction. In this example, RCA priming site 515 is downstream from target specific region 515*b*. However, other locations are possible, as long as the positioning the primer site doesn't interfere with the other functions of the probe, e.g., the probe hybridization function and the encoding function.

A coded padlock probe may optionally include other functional sequences. For example, the probe may include index sequences which are unique oligo identifiers present in the probe sequence or inserted as part of the assay. Index sequences, such as sample barcodes, allow differentiation among different samples, experiments, etc. during the detection event (i.e., reading (decoding) the code).

The coded padlock probe may include unique molecular identifiers. UMIs may be inserted anywhere within the probe to address downstream readout and data analysis purposes. For example, UMIs may be introduced to distinguish unique recognition events with single-molecule resolution during the readout. UMI's may facilitate error correction and/or individual molecule counting.

A coded padlock probe may include other primers in addition to the priming region required for RCA amplification. Other priming regions may, for example, be present to facilitate the readout of an index, a UMI or other oligonucleotide sequences present in the probe. Priming regions may allow parallel or serial reading schemes. They may also be used to increase the amount of multiplexing or allow sequential readout. For instance, if a plurality of probes or amplified objects are present, only those containing a specific primer will be amplified or read. Primers may also be used to facilitate the capture and immobilization of a probe or amplified object onto a surface (e.g., via DNA-DNA hybridization).

A coded padlock probe may include one or more sequences recognizable by enzymes, such as endonucleases. Various sequences may be selected and used to facilitate additional transformations, such as digestion, nick or gap formation, phosphorylation etc. In one embodiment, the probe includes one or more restriction sites.

A coded padlock probe may include one or more non-natural NTP components. Examples include phosphorothioate groups, locked DNA (LNA), peptide DNA (PNA) and others, which may be included to improve certain features of the probe, such as melting temperature for target recognition, or primer recognition, or resistance to degradation. Additionally, abasic NTPs ("wobble bases") may be included in the probe sequence to add degeneracy to targeting or priming regions and extend the ability to recognize a broader number of complementary sequences.

A coded padlock probe may include one or more chemical moieties. Such chemical moieties may be included in the probe structure or added at any stage of the workflow to enable additional transformations or properties. Examples include cleavable groups to open or linearize the probe, reactive groups to add additional components such as dyes, and groups to facilitate immobilization on surfaces.

A coded padlock probe may include CRISPR recognition sequences, oligo sequences designed to be recognized by CRISPR enzymes and replaced with other arbitrary sequences. The probe may optionally include one or more oligo sequences designed to be recognized by transposases and replaced with other arbitrary sequences.

A coded padlock probe may optionally include one or more adapter primers for compatibility with sequencing by synthesis (SBS) and other non-SBS platforms. The adapter primers may be included in the probe sequence or added at any stage as part of the workflow. Such adapter primers may be used directly to immobilize, cluster, extend, and amplify as precursor activities to a decoding run by SBS or another non-SBS method.

In one embodiment, a padlock probe assay workflow may include:

(i) hybridizing the probe to a target;

(ii) optionally, extending the hybridized probe to fill any single-stranded gap remaining between the two probe arms;

(iii) circularizing the probe when the target analyte is present;

(iv) cleaning-up (e.g., by exonuclease or other mean) non-circularized probes remaining after ligation;

(v) amplifying the circularized probe by RCA or other methods;

(vi) capturing of the amplified product on a surface;

(vii) degrading the amplified product to generate a sequencing compatible library;

(viii) preparing the library for sequencing, using sequencing sample preparation workflows suitable for a desired sequencing platform; and reading out or decoding the code.

Index Sequences

Index sequences, such as sample barcodes, allow differentiation among different samples, experiments, etc. during the detection event (i.e., reading (decoding) the code). Indexes may be added to a padlock probe using a variety of strategies.

Indexes may be added during the synthesis of a padlock probe. In this case, for every probe manufactured, the number of probes is N×P, where N is the number of indices and P is the plexity of the probe pool.

Indexes may be added after probe synthesis as part of manufacturing or at a site of use as a step prior to performing an encoded assay. In this case, only one synthesis is required for each probe and additional functional elements. Additional functional elements may be added to a probe to enable insertion of an index. Examples of functional elements that may be added include (i) non-natural nucleotides (e.g., biotin, amine, etc.) and (ii) polynucleotides that enable biochemical transformation of the probe to contain an index sequence such as adapters for ligations or extension ligations, restriction endonuclease recognition sites, and transposome binding sites.

Indexes may be added during an encoded assay. For example, a ligation reaction to insert an index can occur at the same time as ligation of the padlock probe at the target site of interest to generate a circularized padlock probe (i.e., the transformation event). In some cases, the ligation reaction may be a gap-fill extension/ligation reaction.

Indexes may be added after ligation of the padlock probe and RCA by including modified nucleotides during the RCA reaction. The modified nucleotides may then be coupled to an index sequence. In cases where there is a covalent or non-covalent interaction, either moiety can be linked to the index sequence or incorporated during RCA.

Examples of coupling strategies include: (i) ligand protein pairs such as biotin-streptavidin, antigen-antibody, CLIP tag and SNAP tag pair (i.e., O6-benzylguanine derivatives coupling to O6-alkylguanine-DNA-alkyltransferase, wherein either the protein or the substrate may be bound to the probe), carbohydrate-protein pairs (e.g., lectins), and digoxigenin-DIG-binding protein; (ii) peptide-protein pairs (e.g., SpyTag-SpyCatcher); and (iii) hybridizing indexes to a common sequence on the RCA product.

Indexes may be added to RCA products by restriction endonuclease cleavage followed by index ligation.

Indexes may be added to RCA products using a transposase enzyme that fragments and indexes the RCA products.

FIG. 6A is a schematic diagram illustrating an example of adding an index sequence to a probe using a ligand protein coupling strategy. In this example, the ligand protein pair is biotin-streptavidin. Biotinylated nucleotides "B" may be incorporated into a probe 610 and an index sequence 615 may be attached to a streptavidin protein 620. Index sequence 615 may then be coupled to probe 610 via formation of a streptavidin-biotin linkage.

FIG. 6B is a schematic diagram illustrating an example of adding an index sequence to a probe by restriction endonuclease cleavage followed by index ligation. A probe 630 may include a pair of restriction sites 632*a* and 632*b*. A polymerase extension reaction (indicated by dashed arrow) may be performed to convert probe 630 to a double-stranded molecule prior to cleavage. An index sequence 635 may be added to probe 630 by restriction endonuclease cleavage followed by index ligation.

Surface Attachment

The encoded assays of the invention may be performed on a surface. For example, a target may be immobilized on a surface for conducting assays of the invention. The probes of the invention may be immobilized on a surface for conducting assays of the invention. DNA nanoballs of the invention may be immobilized on a surface for conducting assays of the invention. Various intermediate assemblies of molecules of the assays of the invention may be immobilized on a surface for conducting assays of the invention.

Various steps of the invention may be performed on a surface, such as target capture, recognition events, transformation events, amplification, and/or detection events, i.e., determination of the absence or presence of the code (e.g., by sequencing or hybridization-based detection).

Thus, for example, the disclosure provides a surface having a probe as described herein immobilized on the surface. The disclosure provides a surface having a nanoball as described herein immobilized on the surface. The disclosure provides a surface having a target immobilized on the surface. The disclosure provides a surface having a target immobilized on the surface with a probe as described herein hybridized to the target. The disclosure provides a surface having a probe immobilized on the surface with a target as described herein hybridized to the probe. The disclosure provides a surface having a target nucleic acid immobilized on the surface, and a protein or peptide bound to the target nucleic acid. The disclosure provides a surface having a target nucleic acid immobilized on the surface, and an antibody, aptamer, binder, or antibody fragment bound to the target nucleic acid. The disclosure provides a surface having a ligand that has affinity for any of the foregoing immobilized on the surface. For example, the ligand may have affinity for a probe as described herein, a nanoball as described herein, or a target as described herein. The ligand may, for example, be a protein, peptide, antibody, aptamer, binder, or antibody fragment.

A variety of surfaces may be used for the surface attachments described herein. In various embodiments, the surface includes an oxide, a nitride, a metal, an organic or an inorganic polymer (e.g., hydrogel, resin, plastic or other).

The surface may take a variety of forms, e.g., it may be flat or curved. It may be beads or particles. In some cases, the surface is the surface of a flow cell. Beads or other particles may in some embodiments range in size from less than 100 nm up to several centimeters.

Various surface modifications may be used to permit attachment of various components of the assays of the invention to a surface. For example, various anchoring ligands may be used (e.g., streptavidin, biotin, aptamers, antibodies, etc.). Chemical handles, such as click chemistry handles, may be used. Examples include azides, alkynes, unsaturated bonds, amines, carboxylic acids, NHS, DBCO, BCN, tetrazine, epoxy and the like. Single- or double-stranded oligonucleotides may be used. Size ranges of the oligonucleotides may, in some cases, be from about 10 to about 200 nucleotides. Proteins or peptides may be used for surface attachment. Charge-based molecules or polymers may be used, e.g., polyethylenimine.

Various techniques may be used to prepare a surface for binding to a target or to a component of an assay of the invention. In one example, a flow cell with primers may be used. A splint DNA segment that comprises a segment complementary to the primer and a segment that is complementary to the target, or the component of the assay may be hybridized to the primer. A variety of splints may be used on a surface, with various subsets of the splints having different segments complementary to different components of the invention or different targets. Specific splints may be arranged on different regions of a surface. For example, splints may be arranged in a manner that permits the identification of distinct regions of a surface targeted to specific analytes or components of the assays.

In various embodiments, amplification of a nucleic acid may occur on the surface. The nucleic acid may be a target or any nucleic acid component of an assay of the invention. For example, a target analyte may be amplified on a surface, or a probe of the invention may be amplified on a surface, and/or a fragment of any of the foregoing may be amplified on a surface. The amplification may be performed on a bead or particle, or on a flat surface, such as on the surface of a flow cell.

It should also be noted that DNA may be amplified in solution, e.g., in an aqueous suspension or emulsion, such as in microdroplets. Solution-based amplification may be performed, for example, in an open environment, such as the well of the microtiter plate, in a nanowell, or in an enclosed space, droplet in an emulsion, or on a flow cell or other microfluidic device.

Amplification may be by any method of amplification, including for example, PCR, isothermal amplification and/or ultrarapid amplification.

Attachment for immobilization of components of the assays or of targets may be covalent or non-covalent (e.g., Coulombic in nature), temporary or permanent, and/or rendered labile when subject to a particular stimulus.

Examples of mechanisms of lability include:

- Enzymatic—protease, restriction endonuclease, CRISPR-Cas9
- Chemical—reduction, hydrolysis, nucleophilic attack, displacement, reducing of a disulfide bond
- Temperature—melting of duplexed hybridized DNA, thermodynamically unfavorable conditions (Positive deltaG)
- pH—hydrazone, carbonate, etc.
- Light—O-nitrobenzyl or derivatives where absorption of light of a particular wavelength(s) can cause bond rearrangements or cleavage. Light sensitive groups include nitro-benzene derivatives
- Ligand mediated—competitive competition for binding site (see examples below)
  - Peptide-tagged oligos with protein interactions—e.g., Spy-catcher. The moiety may be the ligand or the protein.
  - Peptide-tagged oligo with heavy metal interactions—e.g., Hexa-histidine—to Cu. The moiety may be the ligand or the protein.
  - CLIP tag and SNAP tag pair—i.e., O6-benzylguanine derivatives coupling to O6-alkylguanine-DNA-alkyltransferase. Either the protein or the substrate may be bound to the oligo.
  - Carbohydrate-protein pairs, e.g., lectins
  - The moiety may be a ligand (e.g., biotin, digoxigenin) coupled to a fluorescently-tagged protein (e.g., avidin, streptavidin, DIG-binding protein)
- Cleavage can be performed by cleaving a moiety dangling on a nucleotide, or a nucleotide or a nucleobase within the oligo sequence or the di-nucleotide linkage, e.g., uracil and USER cocktail (uracil-N-deglycosylase (UNG)) followed by Endonuclease VIII or FPG (Formamidopyrimidine DNA Glycosylase with Bifunctional DNA glycosylase with DNA N-glycosylase and AP lyase activities)
- Cleavage can be performed by an enzyme Surface-Based Workflows A variety of surface-based workflows are possible within the scope of the assays disclosed. In some embodiments, a surface-based workflow may use a padlock probe that includes a recognition element associated with a code. The code may be a soft decodable code, such as a trellis code. In some embodiments, a surface-based workflow may use a dual probe that includes a recognition element associated with a code (e.g., a trellis code).

In some embodiments, a surface-based workflow may include immobilizing a target on a surface and hybridizing a probe to the target. In one embodiment, a surface-based workflow may include:

(i) immobilizing the target on a surface;
(ii) hybridizing a probe to the immobilized target;
(iii) circularizing the probe to produce a circular modified probe; and
(iv) releasing the circular modified probe from the target.

In some embodiments, the target may be a nucleic acid, e.g., DNA. In this case, immobilization of the nucleic acid target (e.g., DNA) may be at an end of the target or via a side chain or internal segment of the target.

Figure 7:
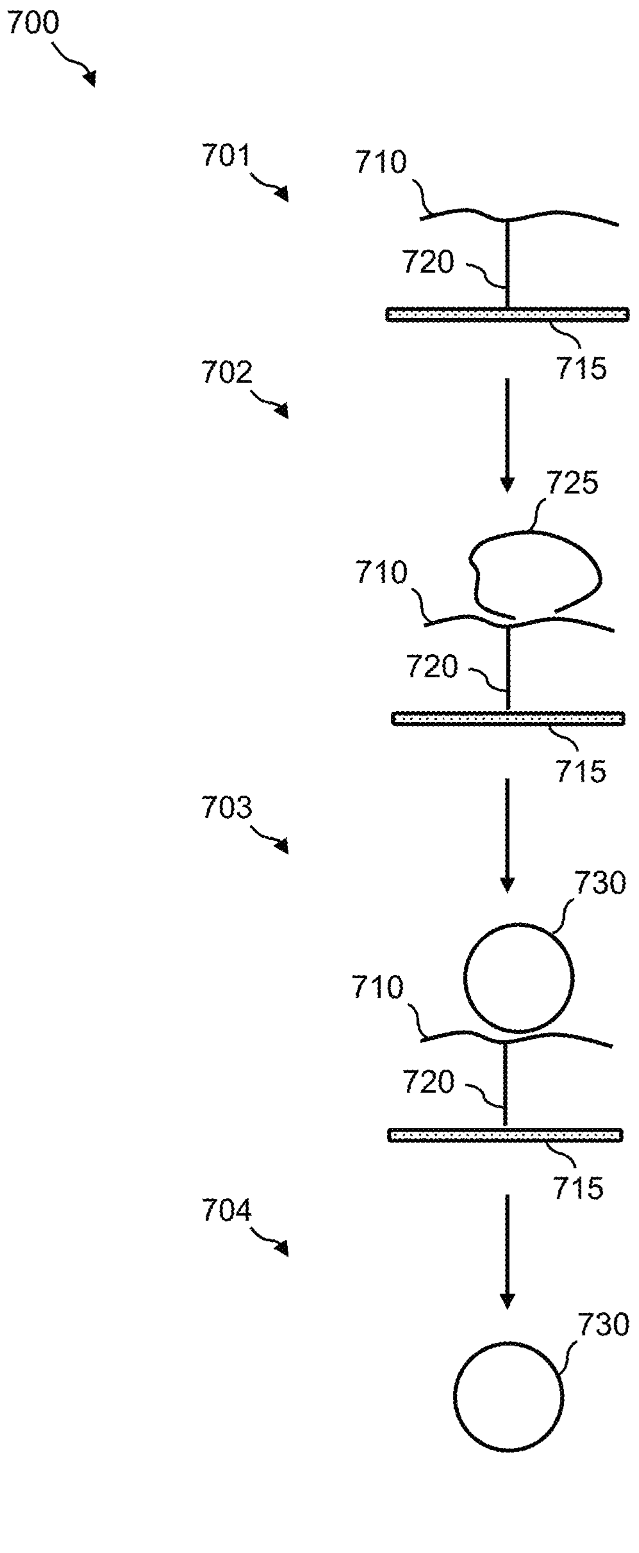
FIG. 7 is a schematic diagram of an example of a surface-based workflow, wherein the target is immobilized on the surface and used to template the ligation of a probe to produce a circular modified probe.

FIG. 7 is a schematic diagram of an example of a surface-based workflow 700, wherein the target is immobilized on the surface and used to template the ligation of a probe to produce a circular modified probe. Workflow 700 may include, but is not limited to, the following steps.

In a step 701, a target is immobilized on a surface. For example, a target 710 is immobilized on a surface 715 by an anchor element 720. In one example, target 710 is DNA and anchor element 720 is an oligonucleotide.

In a step 702, a linear probe is hybridized to the immobilized target. For example, a solution that includes a probe 725 is added and a hybridization reaction is performed to bind probe 725 to target 710. In one example, probe 725 is a coded padlock probe.

In a step 703, the probe is circularized. For example, a ligation reaction is performed to circularize probe 725 to produce a circular modified probe 730. In some cases, a gap-fill extension/ligation reaction is used to circularize probe 725 to produce the circular modified probe.

In a step 704, the circular modified probe is released from the immobilized target for downstream processing. For example, circular modified probe 730 may be dehybridized from target 710 and amplified in an RCA reaction to produce a nanoball product.

In some cases, the RCA reaction may be performed in a solution that remains in contact with the surface on which the target is immobilized (e.g., in the same container, well, reservoir, liquid volume or droplet). In some cases, the solution comprising the released modified probe may be transferred to a separate container prior to performing the RCA reaction. In some cases, the solution comprising the released modified probe may be transferred to a different surface prior to performing the RCA reaction.

In some embodiments, the immobilized target (e.g., DNA) may be used to prime the RCA reaction. In one embodiment, a surface-based workflow may include:

(i) immobilizing the target on a surface;
(ii) hybridizing a probe to the target;
(iii) circularizing the probe to produce a circular modified probe; and
(iv) using the target to prime an RCA reaction to generate a nanoball product.

Figure 8:
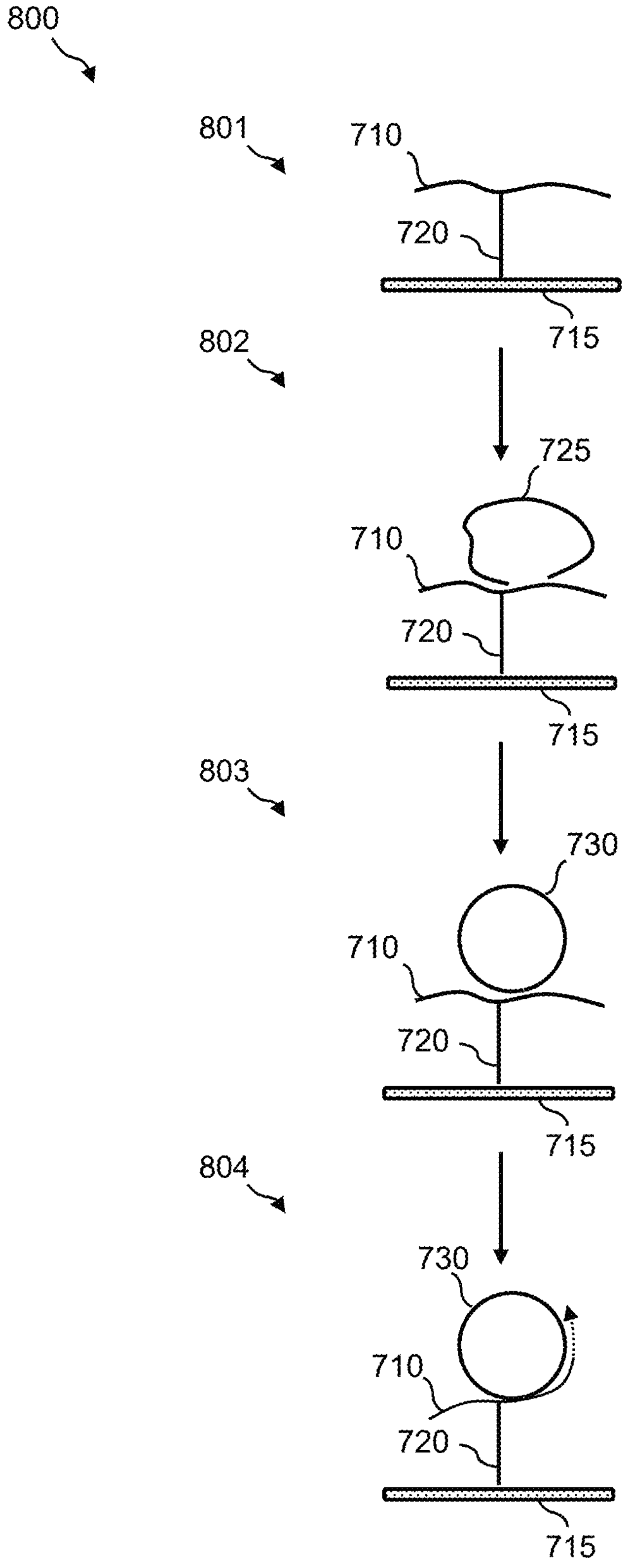
FIG. 8 is a schematic diagram of an example of a surface-based workflow, wherein the target immobilized on the surface is used as a primer to initiate the amplification of the probe to generate a nanoball product.

FIG. 8 is a schematic diagram of an example of a surface-based workflow 800, wherein the target immobilized on the surface is used as a primer to initiate the amplification of the probe to generate a nanoball product. Workflow 800 may include, but is not limited to, the following steps.

In a step 801, a target analyte is immobilized on a surface. For example, a target 710 is immobilized on a surface 715 by an anchor element 720. In one example, target 710 is DNA and anchor element 720 is an oligonucleotide.

In a step 802, a linear probe is hybridized to the immobilized target. For example, a solution that includes a probe 725 (e.g., a coded padlock probe) is added and a hybridization reaction is performed to bind probe 725 to target 710.

In a step 803, the probe is circularized. For example, a ligation reaction is performed to circularize probe 725 to produce a circular modified probe 730. In some cases, a gap-fill extension/ligation reaction is used to circularize probe 725 to produce the circular modified probe.

In a step 804, the immobilized target 710 is used to as a primer to initiate an RCA reaction to generate a nanoball product.

In some embodiments, a surface-based workflow may include immobilizing a probe (or a part thereof) on a surface and using the immobilized probe to capture a target. In one embodiment, a surface-based workflow may include:

(i) immobilizing the probe (or a part thereof) on a surface;
(ii) hybridizing a target to the probe;
(iii) circularizing the probe to produce a circular modified probe; and
(iv) using the target to prime an RCA reaction to generate a nanoball product.

Figure 9:
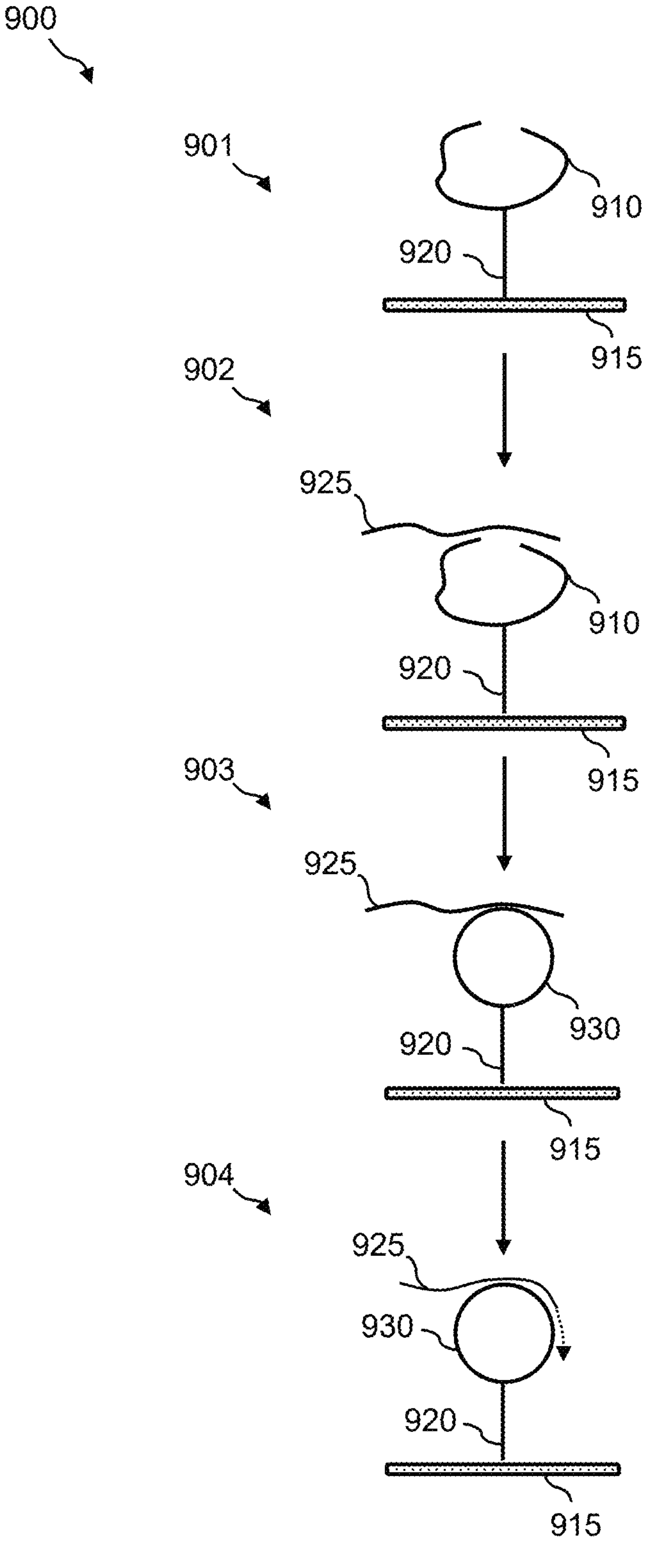
FIG. 9 is a schematic diagram of an example of a surface-based workflow, wherein the probe is immobilized on the surface and the immobilized probe is used capture a target.

FIG. 9 is a schematic diagram of an example of a surface-based workflow 900, wherein the probe is immobilized on the surface and the immobilized probe is used capture a target. Workflow 900 may include, but is not limited to, the following steps.

In a step 901, a linear probe is immobilized on a surface. For example, a probe 910 is immobilized on a surface 915 by an anchor element 920. In one example, probe 910 is a padlock probe and anchor element 920 is an oligonucleotide.

In a step 902, a target is hybridized to the immobilized probe. For example, a solution that may include a target 925 is added and a hybridization reaction is performed to bind target 925 to probe 910.

In a step 903, the probe is circularized. For example, a ligation reaction is performed to circularize probe 910 to produce a circular modified probe 930. In some cases, a gap-fill extension/ligation reaction is used to circularize probe 910 to produce the circular modified probe.

In a step 904, the circular modified probe is amplified in an RCA reaction to generate a nanoball product. Circular modified probe 930 may be amplified without being released from the surface. For example, circular modified probe 930 may be amplified in an RCA reaction using target 925 as a primer to initiate the amplification reaction.

In some embodiments, the circular modified probe may be released from the surface prior to amplification. In some cases, the RCA reaction may be performed in a solution that remains in contact with the surface on which the probe was anchored (e.g., in the same container, well, reservoir, liquid volume or droplet). In some cases, the solution comprising the released modified probe may be transferred to a separate container prior to performing the RCA reaction.

In some embodiments, the solution comprising the released modified probe may be transferred to a different surface prior to performing the RCA reaction. In one embodiment, oligonucleotides bound to the new surface may be used as capture moieties to immobilize the circular modified probe on the surface and to initiate the amplification reaction. In one embodiment, the target may be immobilized on the new surface and used to initiate the amplification reaction.

A surface-based workflow may use a dual probe as a recognition element. In one embodiment, a surface-based workflow using a dual probe may include:

(i) hybridizing a target to a first probe;
(ii) hybridizing the target to a second probe; and
(iii) performing a ligation or a gap-fill ligation reaction to link the first probe and the second probe.

In some embodiments, the first probe and the second probe may both be immobilized on the surface.

In some embodiments, the first probe is immobilized on the surface and the second probe is in solution. The surface may, for example, be the surface of a flow cell.

Figure 10A:
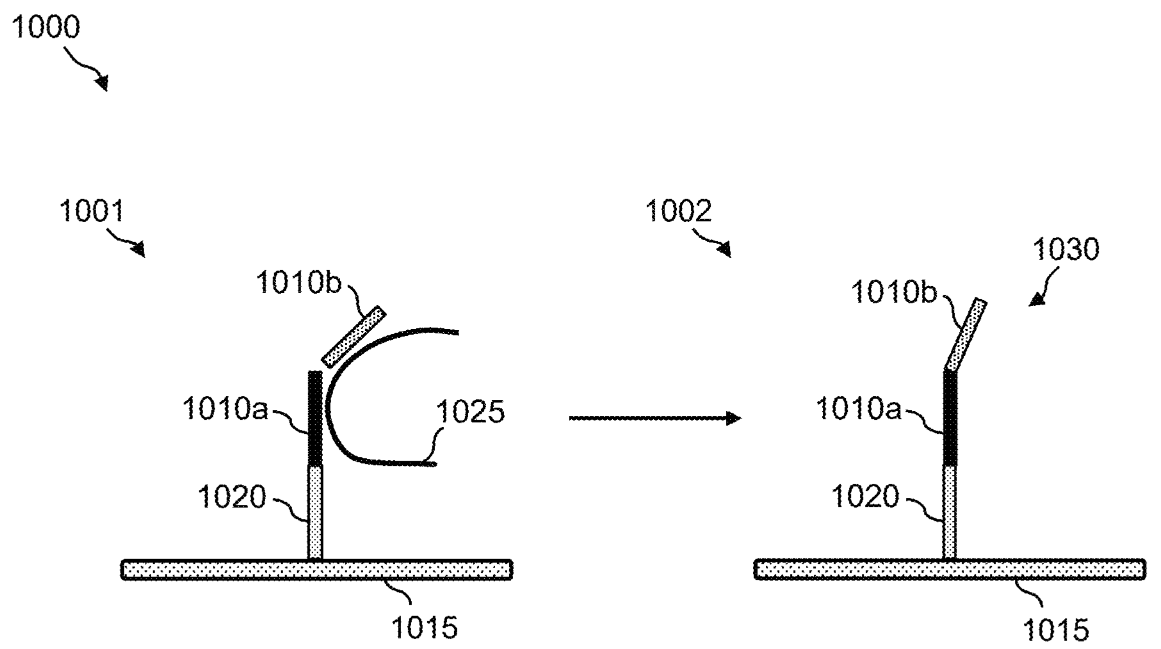
FIG. 10A is a schematic diagram of an example of a dual probe workflow, wherein a first probe is immobilized on the surface and the second probe is in solution.

FIG. 10A is a schematic diagram of an example of a dual probe workflow 1000, wherein a first probe is immobilized on the surface and the second probe is in solution. Workflow 1000 may include, but is not limited to, the following steps.

In a step 1001, a target is hybridized to a first probe immobilized on a surface. For example, a first probe 1010*a* is immobilized on a surface 1015 via an anchor element 1020. In one example, anchor element 1020 is a surface bound primer. The surface bound primer may, for example, be a primer on a sequencing flow cell. A process for anchoring a probe (or a segment thereof) on a surface bound primer is described below with reference to FIG. 11.

First probe 1010*a* may be used as a capture element for recognizing and binding a target. For example, a solution that may include a DNA target 1025 is added and a hybridization reaction is performed to bind target 1025 to first probe 1010*a*.

In a step 1002, the target is hybridized to a second probe. For example, a second probe 1010*b* that includes a sequence for recognizing and binding target 1025 is added and a hybridization reaction is performed to hybridize second probe 1010*b* to target 1025.

In a step 1003, the dual probe is ligated to link the first probe and the second probe to produce a modified probe immobilized on the surface. For example, a ligation reaction is performed to link first probe 1010*a* and second probe 1010*b* to produce a modified probe 1030.

In some cases, a gap-fill extension/ligation reaction is used to link first probe 1010*a* and second probe 1010*b* to produce the modified probe.

Figure 10B:
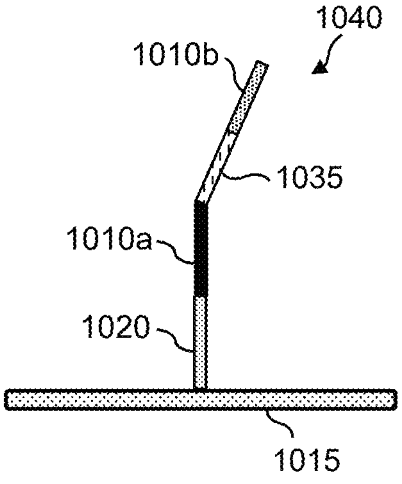
FIG. 10B is a schematic diagram illustrating an example of a surface bound probe that includes a second surface adapter.

In some cases, second probe 1010*b* may further include a surface oligonucleotide adapter for binding to another surface bound primer. FIG. 10B is a schematic diagram illustrating an example of a surface bound probe that includes a second surface adapter. In this example, probe 1010*b* may further include a surface adapter 1035 that is introduced during ligation of probe 1010*a* and 1010*b* to produce a modified probe 1040.

The disclosure provides a process for preparing a surface for binding to a target or to a component of an assay of the invention. Surface modifications may serve a dual purpose. For example, a surface modification may (i) capture the target of interest and (ii) initiate the amplification of a probe or a portion thereof on the surface. In another example, a surface modification may (i) capture a component of the assay (e.g., a circular modified probe), and (ii) initiate an RCA reaction to generate a nanoball product.

A surface bound primer may be enzymatically modified to include a capture sequence. A capture sequence may be a target-specific probe or a sequence that is specific for a component of an assay. A surface bound primer may be enzymatically modified to include a probe or a portion thereof (e.g., a probe arm or a primer binding site). For example, a splint oligonucleotide that includes a segment that is complementary to a surface bound primer and a segment that is complementary to a probe (or a portion thereof) may be hybridized to the primer and used to template the synthesis of a surface bound probe. In one example, the surface bound probe is one arm of a dual probe.

Figure 11:
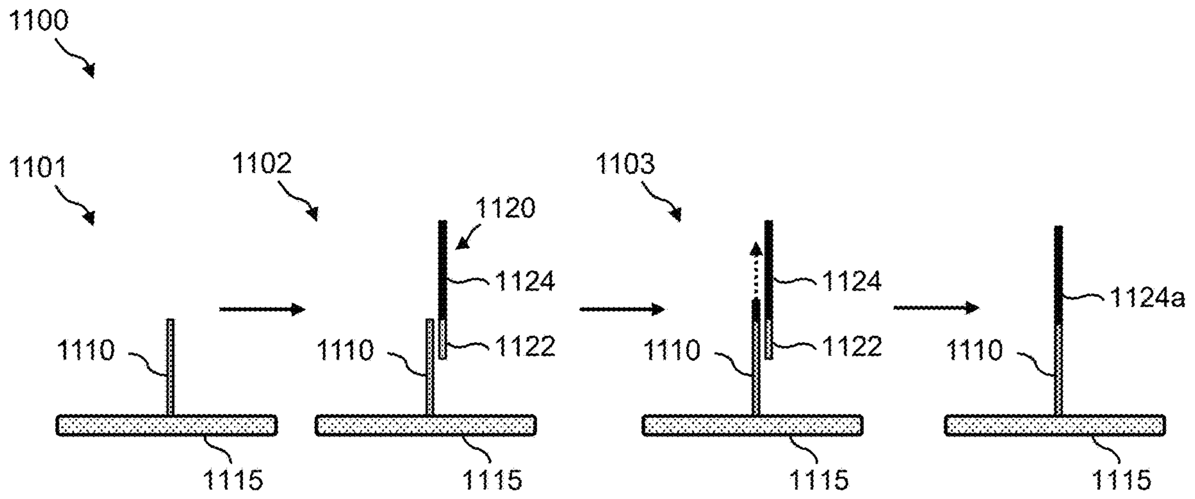
FIG. 11 is a schematic diagram illustrating an example of a process for synthesizing a surface bound probe using a splint oligonucleotide.

FIG. 11 is a schematic diagram illustrating an example of a process 1100 for synthesizing a surface bound probe using a splint oligonucleotide. Process 1100 may include, but is not limited to, the following steps.

In a step 1101, a surface is provided with a surface bound primer. For example, a primer 1110 is bound to a surface 1115. Surface 1115 may, for example, be the surface of a flow cell.

In a step 1102, a splint oligonucleotide is hybridized to the surface bound primer. For example, a splint 1120 that includes a segment 1122 that is complementary to primer 1110 and a capture segment 1124 is hybridized to primer 1110. In one example, capture segment 1124 is one arm of a dual capture probe.

In a step 1103, a primer extension reaction is performed to synthesize the surface bound probe. For example, in the primer extension reaction, splint 1120 is used to template the synthesis of a capture segment 1124 extending from primer 1110 to produce a surface bound probe arm 1124*a*.

Amplification Strategies

Amplification may be by any method of amplification, including for example, on-surface PCR, isothermal amplification, rolling circle amplification, and/or ultrarapid amplification.

Surface based amplification may be performed using PCR with surface-anchored primers (e.g., Illumina bridge amplification technology) or recombinase polymerase amplification (RPA) (e.g., ExAmp technology).

Clonally amplified material may be a nanoball or a DNA cluster (e.g., Illumina surface-based amplification).

An amplification strategy may include adding a second surface adapter to a probe. The second surface adapter may be complementary to a second primer on a flow cell surface (e.g., a bridge amplification primer). The second surface adapter may, for example, be added to a probe during the ligation or gap-fill ligation event or added separately by PCR or through its own ligation to a probe. For example, an amplification strategy may include using the splint ligation approach described with reference to FIG. 11 to add a second surface adapter to a surface bound probe to facilitate bridge amplification. Bridge amplification may be used to create clusters for sequencing.

Figure 12A:
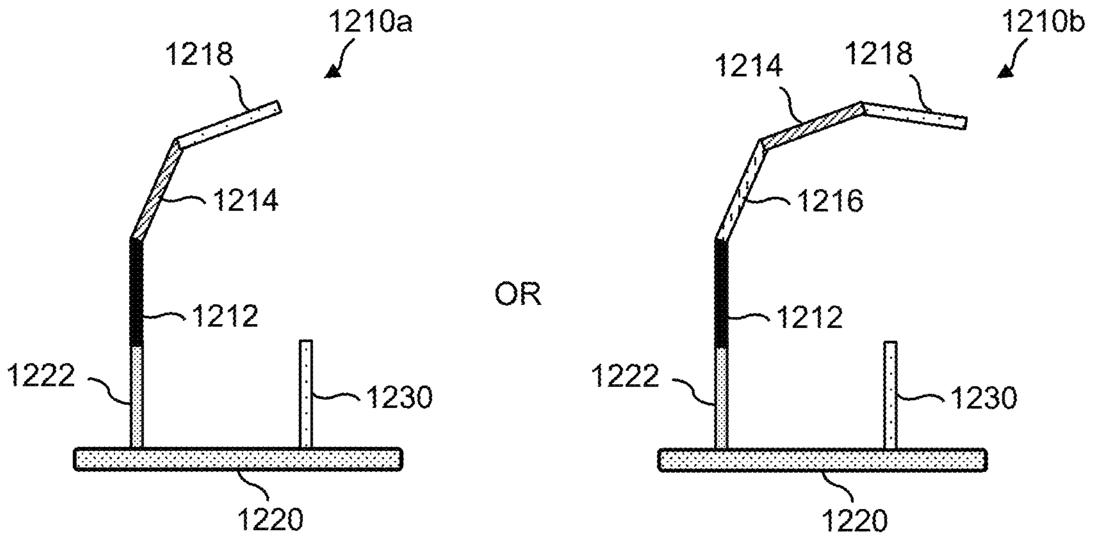
FIG. 12A and FIG. 12B are schematic diagrams illustrating an example of surface bound probe structures comprising a second surface adapter and showing a process of performing bridge amplification, respectively.
Figure 12B:
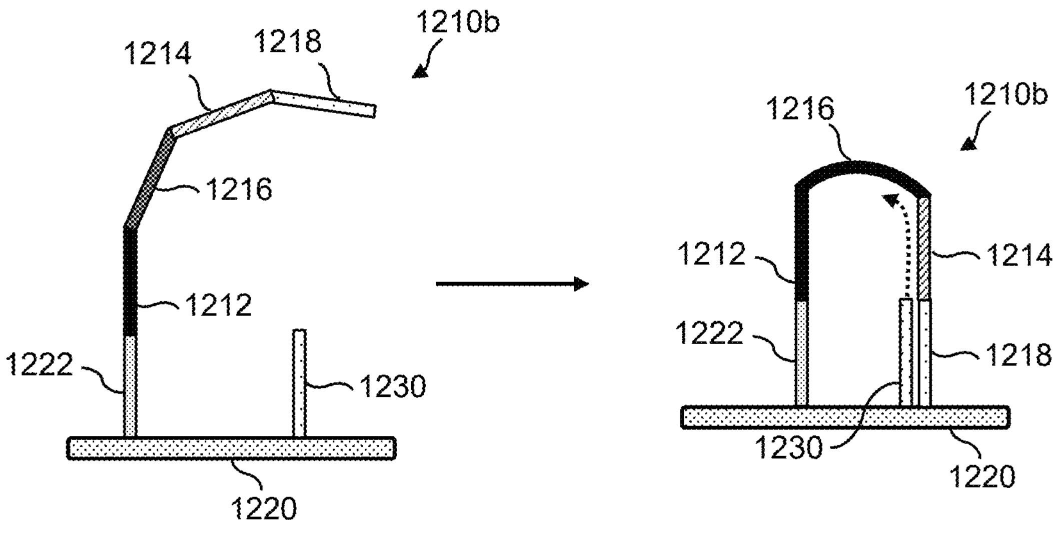

FIG. 12A and FIG. 12B are schematic diagrams illustrating an example of surface bound probe structures comprising a second surface adapter and showing a process of performing bridge amplification, respectively. In this example, the probe structure is a modified dual probe as described above with reference to FIG. 10, wherein the probe further includes a second surface adapter for bridge amplification. For example, a probe structure 1210 (i.e., probe structures 1210*a* and 1210*b*) may be anchored to a surface 1220 by a primer 1222. Primer 1222 may be a primer used in a bridge amplification reaction. Probe structure 1210*a* may include a first probe element 1212, a second probe element 1214, and a surface adapter 1218.

Surface adapter 1218 may be complementary to a second primer 1230 on surface 1220. Second primer 1230 may be a primer used in a bridge amplification reaction. Probe structure 1210*b* may include first probe element 1212 and second probe element 1214 that are separated by an adapter 1216, and surface adapter 1218. A bridge amplification reaction (see FIG. 12B) may be performed to create clusters (not shown) for sequencing.

An amplification strategy may include adding a restriction enzyme site in a probe. For example, the probe may include a restriction enzyme site that when hybridized with a complementary oligonucleotide provides a double-stranded site for a restriction endonuclease to cleave the probe, rendering a linear strand. The linear strand may be amplified for downstream processing, e.g., for sequencing. For example, the linear strand may be captured on a flow cell and amplified by bridge amplification (e.g., Illumina bridge amplification technology) or recombinase polymerase amplification (RPA) (e.g., ExAmp technology).

The probe may include surface primers or surface adapter sequences that are complementary to surface bound primers of a flow cell. The adapter sequences may be linked to or adjacent to the restriction site, so that when the site is cut by a restriction enzyme the linear strand is ready for sequencing. As noted, other forms of cleavage are possible, such as CRISPR mediated cleavage or any other double-stranded break inducing protein.

Figure 13:
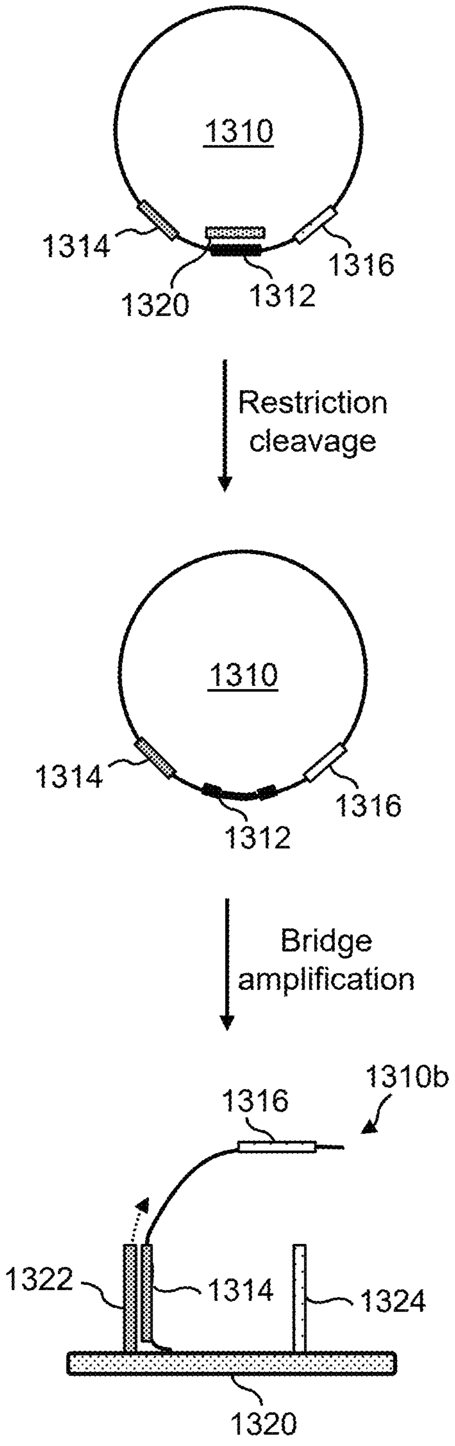
FIG. 13 is a schematic diagram illustrating an example of a probe that includes a restriction enzyme site that may be used to linearize the probe for capture on a flow cell for bridge amplification prior to sequencing.

FIG. 13 is a schematic diagram illustrating an example of a probe that includes a restriction enzyme site that may be used to linearize the probe for capture on a flow cell for bridge amplification prior to sequencing. For example, a probe 1310 may include a restriction site 1312. Restriction site 1312 may be linked to a first surface adapter 1314 and a second surface adapter 1316. An oligonucleotide 1320 that is complementary to restriction site 1312 may be hybridized to probe 1310 to provide a double-stranded site for restriction endonuclease cleavage. Cleavage at restriction site 1312 generates a linear probe 1310*b*. Linear probe 1310*b* may be loaded on a surface 1320 (e.g., a flow cell surface) that includes a first primer 1322 and a second primer 1324 immobilized thereon. Hybridization of adapter 1314 to primer 1322 may be used to initiate a bridge amplification reaction to generate clusters for sequencing.

Similarly, a nanoball may include surface primers or sequencing adapters linked to or adjacent to a restriction site, so that when the site is cut by a restriction enzyme the linear strands are released ready for sequencing. As noted, other forms of cleavage are possible, such as CRISPR mediated cleavage.

In another embodiment, a nanoball with adapter sequences complementary to surface bound primers may be seeded directly onto the surface without cleaving. Amplification may proceed through bridge amplification (e.g., Illumina bridge amplification technology) or recombinase polymerase amplification (RPA) (e.g., ExAmp technology) initiated directly.

Figure 14A:
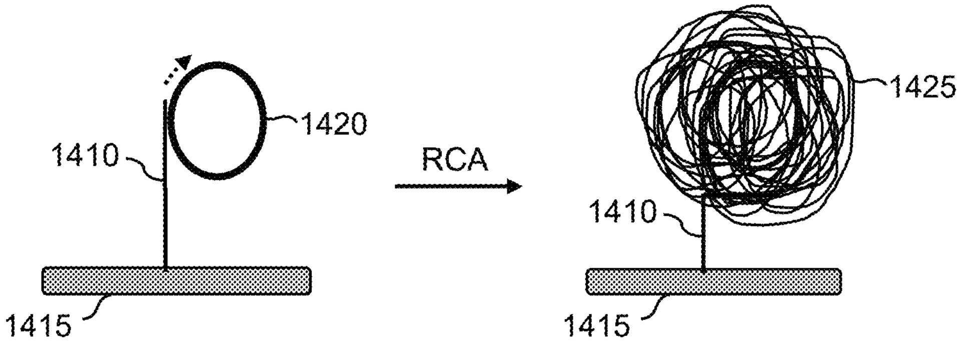
FIG. 14A is a schematic diagram illustrating an example of a process of using a surface-bound oligonucleotide to initiate an RCA reaction.

Rolling circle amplification (RCA) may be used to produce nanoballs as part of the assays of the invention. An RCA reaction may be performed as a surface-bound reaction. For example, RCA may be initiated by an oligonucleotide bound to a surface (e.g., beads, flow cells, microwell, or nanowells). Any method may be used to bind the oligonucleotide to the surface. In one example, the oligonucleotide may be covalently bound to the surface. FIG. 14A is a schematic diagram illustrating an example of a process of using a surface-bound oligonucleotide to initiate an RCA reaction (indicated by the arrow). An oligonucleotide 1410 may be covalently attached to a surface 1415. Oligonucleotide 1410 may include an RCA primer sequence that is complementary to an RCA primer site on a probe 1420. Oligonucleotide 1410 may be used to capture probe 1420 by hybridization of the complementary sequences and initiate the RCA reaction. Because oligonucleotide 1410 is covalently bound to the surface, the surface-bound RCA reaction generates a nanoball 1425 that is covalently attached to the surface.

Figure 14B:
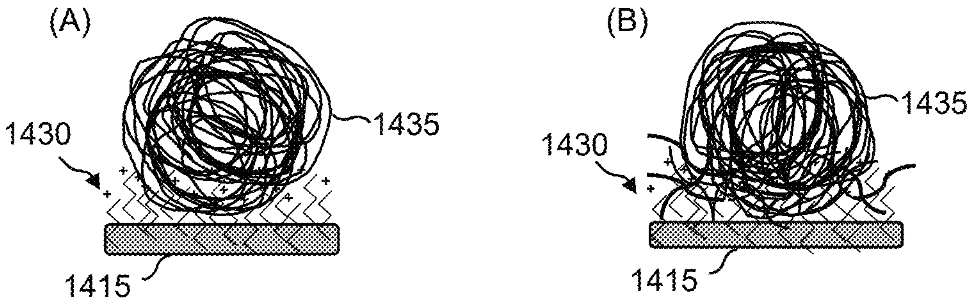
FIG. 14B is a schematic diagram illustrating an example of capturing a nanoball on a cation-coated surface.

In another example, a cation-coated surface (e.g., beads, flow cells, microwells, or nanowells) may be used to capture nanoballs. In one example, the cation-coated surface may be a polylysine-coated surface. FIG. 14B is a schematic diagram illustrating an example of capturing a nanoball on a cation-coated surface. A surface 1415 may be coated with a polylysine coating 1430. An RCA reaction may be performed in the presence of the polylysine coated surface, resulting in simultaneous immobilization and amplification of a nanoball 1435. RCA primers may be supplied in solution (panel A) or bound to the polylysine-coated surface prior to performing the RCA reaction (panel B).

Figure 14C:
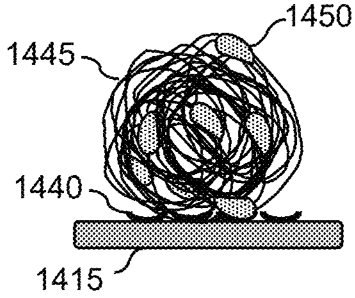
FIG. 14C is a schematic diagram illustrating an example of capturing a nanoball on a streptavidin-coated surface.

In another example, a streptavidin-coated surface (e.g., beads, flow cells, microwells, or nanowells) may be used to capture nanoballs. In this approach, biotin-linked deoxynucleotides may be incorporated into the nanoballs during RCA. The nanoballs will then be bound to the surface by a biotin-streptavidin linkage. FIG. 14C is a schematic diagram illustrating an example of capturing a nanoball on a streptavidin-coated surface. A surface 1415 may be coated with a streptavidin coating 1440. An RCA reaction may be performed in the presence of the streptavidin coated surface using biotin-linked deoxynucleotides to produce a nanoball 1445 that includes biotin moieties 1450 resulting in simultaneous immobilization and amplification of nanoball 1445.

Figure 14D:
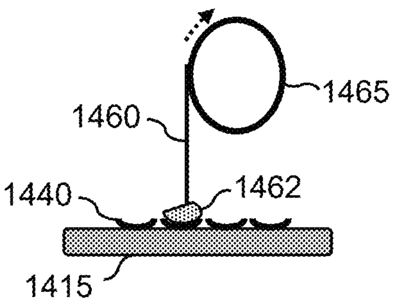
FIG. 14D is a schematic diagram showing an example of using a biotin-streptavidin linkage to perform a surface-bound RCA reaction.

In another embodiment, biotin linked RCA primers may be bound to a surface by a streptavidin-biotin linkage and used to initiate an RCA reaction as described above with reference to FIG. 14A. An example of using a biotin-streptavidin linkage to perform a surface-bound RCA reaction is shown in FIG. 14D. A surface 1415 may be coated with a streptavidin coating 1440. An oligonucleotide 1460 that includes a biotin moiety 1462 may be attached to surface 1415 through a biotin-streptavidin linkage. Oligonucleotide 1416 may include an RCA primer sequence that is complementary to an RCA primer site on a probe 1465. Oligonucleotide 1460 may be used to capture probe 1465 by hybridization of the complementary sequences and initiate the RCA reaction (indicated by the arrow) to produce a nanoball. Amplification in the presence of the streptavidin coated surface further anchors nanoball to the surface.

Following the formation of a nanoball, a determination may be made with respect to the identity of the code. Prior to making the determination, various secondary processing steps are possible within the scope of the assays described herein. The probe may include various elements that facilitate secondary processing steps. Examples include restriction endonuclease sites and CRISPR sites.

The nanoball may be converted to double-stranded DNA (dsDNA) prior to fragmentation. The dsDNA nanoball may be fragmented. In one embodiment, the probe includes restriction sites which are replicated in the nanoball, and the nanoball is fragmented using a restriction enzyme having specificity for the restriction sites.

CRISPR may be used to fragment the nanoball at specific sites.

Random fragmentation of nanoballs may be performed, using known fragmentation techniques.

Tagmentation may be performed on the nanoball, and the tagmentation may be used to add sequencing adapters.

Sequencing Preparation

This disclosure provides a variety of techniques for amplifying and preparing circularized probes for sequencing. In certain embodiments, amplification and preparation for sequencing may be performed sequentially (e.g., PCR+primer ligation). In certain embodiments, amplification and preparation for sequencing may be performed in a single reaction (e.g., adapter addition via PCR). Addition of sequencing adapters may be performed with or without RCA amplification of circularized probes.

In one embodiment, sequencing adapters are added via PCR. In this case, amplification and preparation for sequencing may be a single step. Depending on the probe design, the code, UMI, and index may be read in a single step or in two separate reads with a dehybridization step.

In one embodiment, RCA products (nanoballs) may be fragmented with restriction endonucleases (RE) to yield a multitude of code-containing single stranded nucleic acids. The single-stranded nucleic acids (i.e., the RE reaction products) may then be prepared for sequencing by ligation to adapter sequences.

In one embodiment, sequencing adapters may be added by transposomes that simultaneously fragment double-stranded DNA and add adapters.

As discussed elsewhere in the application, the assays of the invention include a transformation step. Typically, the transformation involves circularization of a probe when a target is present (e.g., by ligation or gap-fill ligation).

Figure 15A:
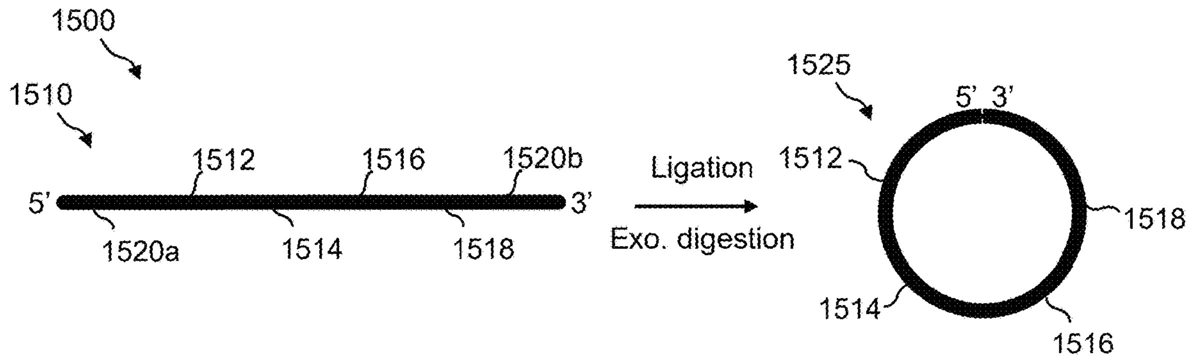
FIG. 15A is a schematic diagram of a transformation process for circularizing a linear probe to form a circular modified probe.

FIG. 15A is a schematic diagram of a transformation process 1500 for circularizing a linear probe to form a circular modified probe. In this example, a probe 1510 includes a UMI sequence 1512, a code 1514, an SBS primer 1516, and an index primer 1518 all situated between a 5' target recognition element 1520*a* and a 3' target recognition element 1520*b*. In the presence of a target (not shown), probe 1510 is circularized in a ligation reaction to yield a circular modified probe 1525. The ligation reaction may be followed by an exonuclease digestion step to remove unligated probes 1510 and target.

Figure 15B:
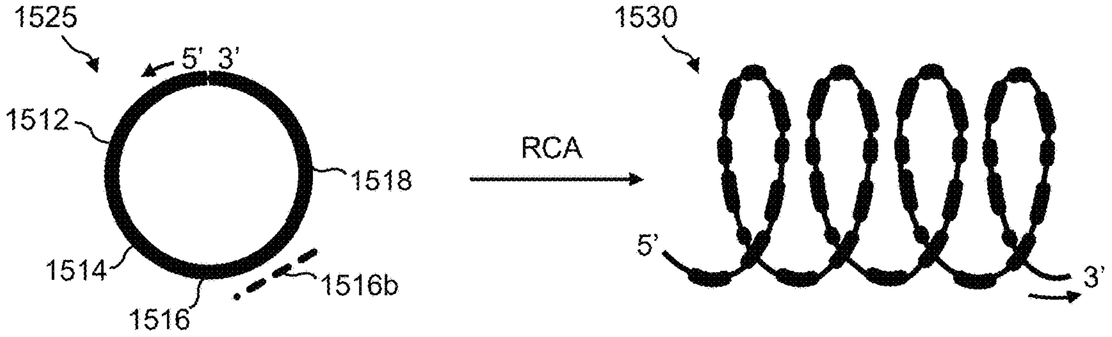
FIG. 15B is a schematic diagram showing RCA amplification of the circular modified probe to yield a nanoball product.

The circular modified probe shown in FIG. 15A may, in some cases, be amplified in a rolling circle amplification to form a nanoball product. FIG. 15B is a schematic diagram showing RCA amplification of the circular modified probe to yield a nanoball product. For example, in an RCA reaction an SBS primer 1516*b* that is the reverse complement to SBS primer 1516 may be hybridized to circular modified probe 1525 and used to initiate the RCA reaction to generate a nanoball 1530. Nanoball 1530 is a polymeric molecule (concatemer) that includes multiple repeated copies of circular modified probe 1525, wherein each copy includes SBS primer 1516, code 1514, UMI sequence 1512, target recognition elements 1520, and index primer 1518. In this example, the complement (i.e., copy) of modified probe 1525 is indicated by the dashed line.

In some embodiments, the RCA products (nanoballs) may be sequenced directly. In some embodiments, sequencing adapters may be added by PCR amplification, followed by clustering and sequencing.

Figure 15C:
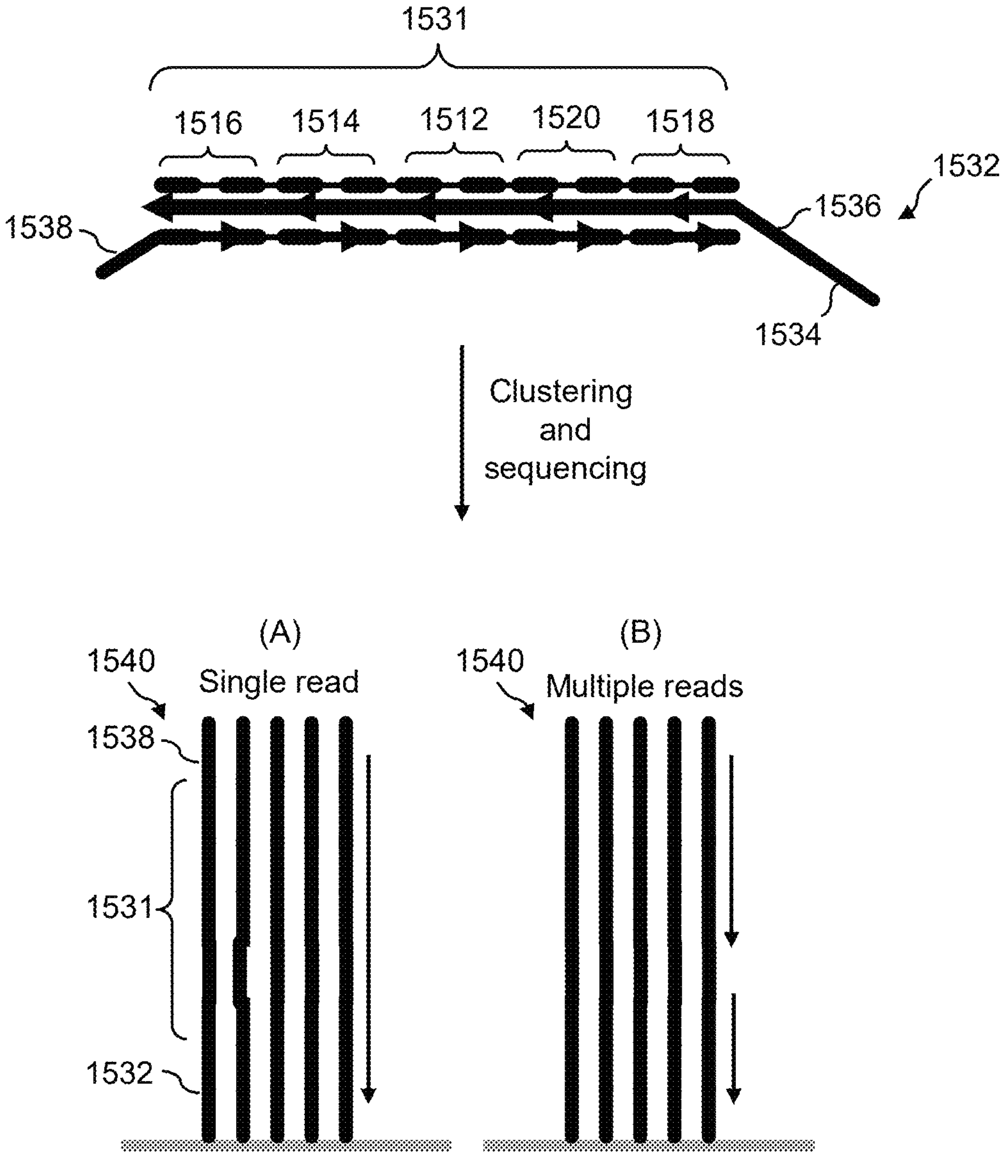
FIG. 15C is a schematic diagram showing the addition of sequencing adapters to a nanoball concatemer for subsequent clustering and sequencing.

FIG. 15C is a schematic diagram showing the addition of sequencing adapters to a nanoball concatemer for subsequent clustering and sequencing. The PCR reaction may use a pair of amplification primers 1532 and 1538. Amplification primer 1532 may include a sequencing adapter sequence 1534 (e.g., a P7 adapter sequence) and an index sequence 1536 (e.g., a sample index sequence). Amplification primer 1538 may include a second sequencing adapter sequence (e.g., a P5 adapter sequence). Amplification primers 1532 and 1538 are used in the PCR reaction to initiate amplification of nanoball 1530 to generate multiple single probe copies 1540 of modified probe 1525 that now include the adapter sequences and the index sequence. In this example, a single probe copy 1531 (indicated by the dashed lines) of the sequences in the original circular modified probe 1525 is shown. A bridge amplification reaction may then be performed to generate a clonal cluster 1540 for sequencing. Sequencing may be performed as a single read (A) or as multiple reads (B). Sequencing as a single read provides the UMI sequence, the code sequence, and the index sequence. Sequencing as multiple reads may include, for example, one read to provide the UMI and code sequences, and a second read to provide the index sequence.

In another embodiment, the probes of the invention may include restriction sites. The probes may be designed with restriction sites, or the restriction sites may be added to the probes as part of the assay process. The restriction sites will be amplified into the nanoball and will provide multiple sites at which to cut the nanoball into fragments.

Figure 16A:
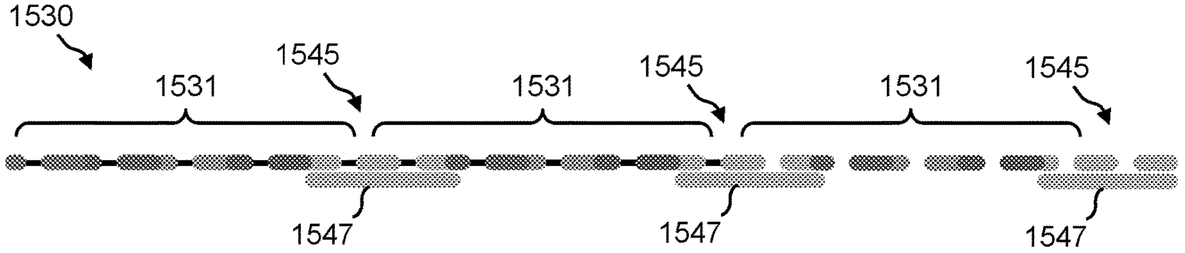
FIG. 16A is a schematic diagram of an example of a portion of the nanoball of FIG. 15 that includes restriction sites that may be used to separate repeated copies of the probe in the nanoball.
Figure 16B:
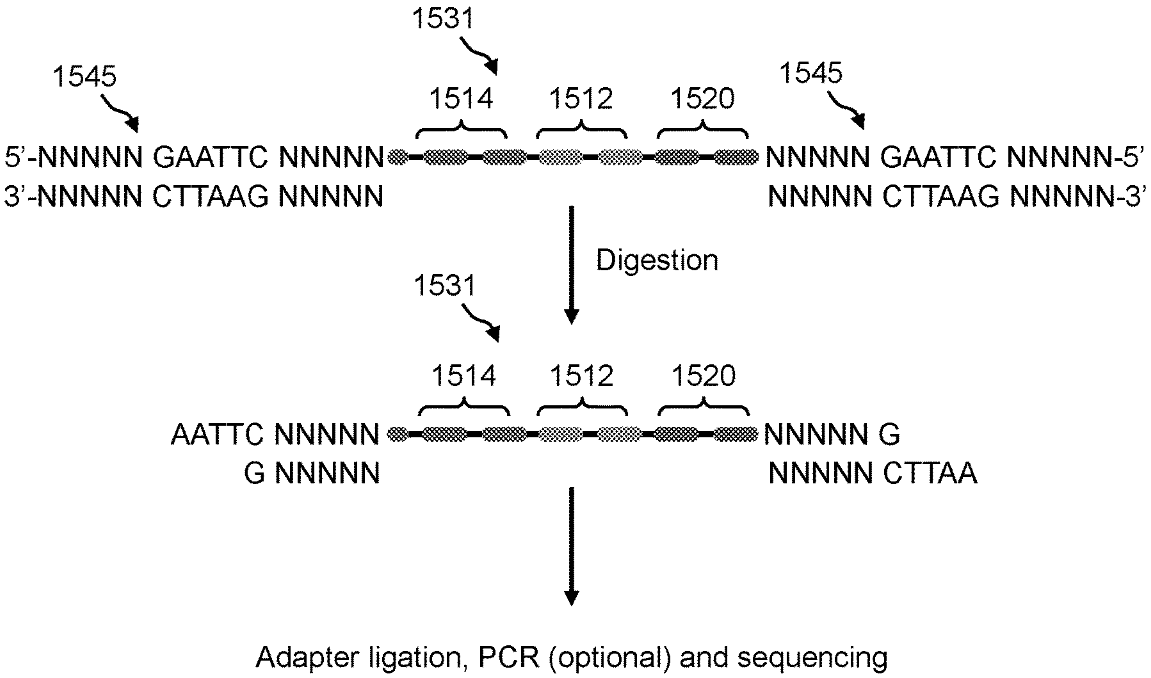
FIG. 16B is a schematic diagram of an example of a portion of the nanoball including restriction sites of FIG. 16A.

FIG. 16 is a schematic diagram of an example of a portion of nanoball 1530 of FIG. 15 that includes restriction sites that may be used to separate repeated copies of the probe in the nanoball. Referring to panel "A", in this example, nanoball 1530 includes three probe copies 1531 that may be separated by cleavage at a restriction endonuclease site 1545. A restriction site (RS) complementary sequence 1547 may be hybridized to restriction sites 1545 to provide a double-stranded region for cleavage.

Referring to panel "B", restriction sites consist of a recognition sequence and flanking bases to ensure that strands remain hybridized after cleavage. Flanking sequences (NNNNNN) may be of length ranging from about 5 to about 50 bases and can be designed to minimize interactions with other probe components and tune the melting temperature (Tm). In this example, the flanking sequences include five bases (N). The RS sequences can be used as an SBS primer such that sequencing begins with the code or may include a spacer region that is read prior to the code.

Digestion of nanoball 1530 hybridized to RS complementary sequences 1547 yields many code-containing DNA fragments with termini that contain single-stranded DNA overhangs or "sticky ends". The digestion products may be further processed for sequencing. For example, adapters may be ligated to the sticky ends resulting from the restriction digestion.

Alternatively, the ends may be blunt ended (i.e., the single-stranded overhangs removed) and prepared for ligation to adapters. Blunt ended fragments may then be processed via typical sequencing sample preparation protocols such as A-tailing and adapter ligation.

An additional embodiment includes using a primer and polymerase to create RCA products where the entire concatemer is double stranded. This structure can then be processed via the restriction endonuclease procedure described above.

Another embodiment includes employing hyperbranched RCA to create many double stranded, code-containing sequences that can be processed via the restriction endonuclease procedure described above.

In certain embodiments, the restriction endonuclease may be a member of the cas family of proteins or a derivative thereof. These proteins recognize longer sequences of DNA, making them more specific.

In an additional embodiment, circularized probes may be prepared for sequencing without RCA.

In certain embodiments, the nanoballs of the invention may be compacted prior to sequencing. Rolling circle amplification produces linear concatemers of single-stranded DNA. When the substrate for RCA is a circularized probe, these concatemers may contain 100s-1000s of copies of a code. When preparing RCA products for sequencing, it is useful to compact them. The compacting may produce spherical structures. The compacted structures can increase localization of signal.

Compaction of RCA products into spherical nanoballs can be accomplished by a variety of techniques. In one embodiment, cationic additives that condense high molecular weight DNA (e.g., spermidine, Mg ions, cationic polymers) may be used. The compactness of a spherical nanoball may be tuned by controlling the concentration of the cationic reagent used. The concentration of the cationic reagent used may be selected to avoid aggregation of multiple nanoballs.

In one embodiment, multivalent oligonucleotide sequences that crosslink sites on RCA products may be used to compact RCA products into spherical nanoballs. The RCA binding sites may be separated by a nucleic acid or polymeric linker to control the degree of compaction. The compactness of the spherical nanoball may, for example, be tuned by controlling the degree of crosslinking in the RCA product.

In one embodiment, incorporation of modified nucleotides followed by crosslinking may be used to compact RCA products into spherical nanoballs. Examples of modified nucleotides that may be used include biotinylated nucleotides that bind to streptavidin proteins and nucleotides that covalently react with multifunctional linkers (e.g., amino nucleotides and NHS-terminated linkers). The compactness of the spherical nanoball may, for example, be tuned by controlling the degree of crosslinking in the RCA product.

In certain embodiments, the assays of the invention make use of nanopore sequencing. A nanoball or a circular modified probe may be sequenced using nanopore sequencing. Various nanopore sequencing sample preparation techniques are known in the art. Amplification is optional. Various components required for other sequencing techniques, such as sequencing primers, may be omitted from the probe. Purification can be accomplished using, for example, SPRI beads or BluePippen. Oxford Nanopore Technologies, Inc. (Oxford, UK) provides kits for sample preparation. Examples include Ligation Sequencing Kit, Native Barcoding Kit 96, and Rapid Barcoding Kit.

In certain embodiments, it may be useful to further amplify RCA products prior to sequencing. For example, in applications that use cell-free DNA (cfDNA) as the input where the analyte number may be low, it may be useful to amplify the RCA product prior to sequencing. In one embodiment, a circle-to-circle amplification approach may be used to produce multiple RCA products from one initial RCA product by monomerization of the concatemer (i.e., cleavage to unit length fragments), recircularization of the unit length fragments (i.e., monomers) and amplification of the newly generated circles in a second RCA reaction to produce multiple RCA product copies for further processing or sequencing. The restriction enzyme approach described with reference to FIG. 16 may be used to digest the initial RCA product to unit length (i.e., monomers). In some cases, an end-to-end joining oligonucleotide plus an end-to-end ligation reaction may be used to circularize the unit size fragments.

Figure 17:
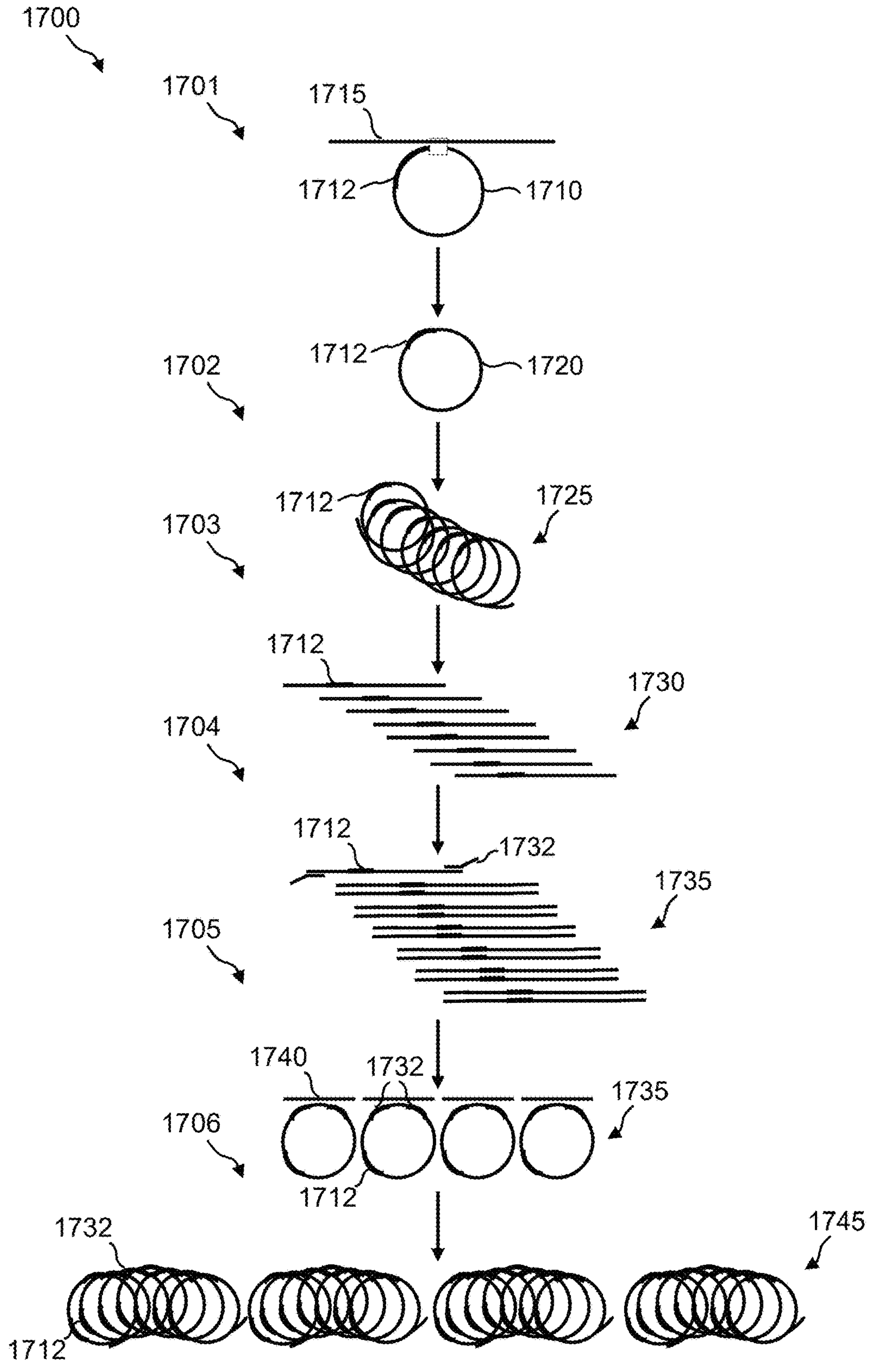
FIG. 17 is a schematic diagram of an example of a process for circularizing and amplifying unit length nanoball fragments to produce multiple RCA nanoball products.

FIG. 17 is a schematic diagram of an example of a process 1700 for circularizing and amplifying unit length nanoball fragments to produce multiple RCA nanoball products. Workflow 1700 may include, but is not limited to, the following steps.

In a step 1701, a probe is hybridized to a target and circularized to yield a circular modified probe. For example, a probe 1710 that includes a code 1712, and a restriction site (not shown) is hybridized to target 1715. A ligation reaction is then performed to circularize probe 1710 to produce a circular modified probe 1720.

In a step 1702, the circular modified probe 1720 is amplified in an RCA reaction to generate a nanoball product 1725. During amplification, the restriction site is amplified into the nanoball and provides multiple sites at which to cut nanoball 1725 into fragments.

In a step 1703, the nanoball product is cleaved to produce multiple unit sized fragments each comprising the code. For example, nanoball 1725 is cleaved at the restriction sites to produce multiple unit size fragments 1730 each comprising code 1712. The cleavage reaction may, for example, be performed as describe with reference to FIG. 16.

In a step 1704, the unit size fragments are amplified in a PCR reaction to generate multiple double-stranded fragments. For example, indexed amplification primers 1732 are hybridized to unit size fragments 1730 and a PCR reaction is performed to produce multiple unit size fragments 1735 that include code 1712 and the indexed amplification primer 1732.

In a step 1705, the amplified unit size fragments are circularized to generate circular unit size fragments. For example, an end-to-end joining oligonucleotide 1740 that is complementary to sequences in amplification primer 1732 is hybridized to unit size fragment 1730 and an end-to-end ligation reaction is performed to generate circular unit size fragments 1735 comprising the code.

In a step 1706, the circular unit size fragments are amplified in a second RCA reaction to produce multiple nanoball copies for further processing or sequencing. For example, circular unit size fragments 1735 are amplified in an RCA reaction to produce multiple nanoballs 1745 each comprising code 1712 and indexed amplification primers 1732.

In an embodiment of process 1700 of FIG. 17, the PCR amplification step 1704 may be omitted and the unit size fragments comprising the code may be re-circularized for subsequent amplification in a second RCA reaction.

Figure 18:
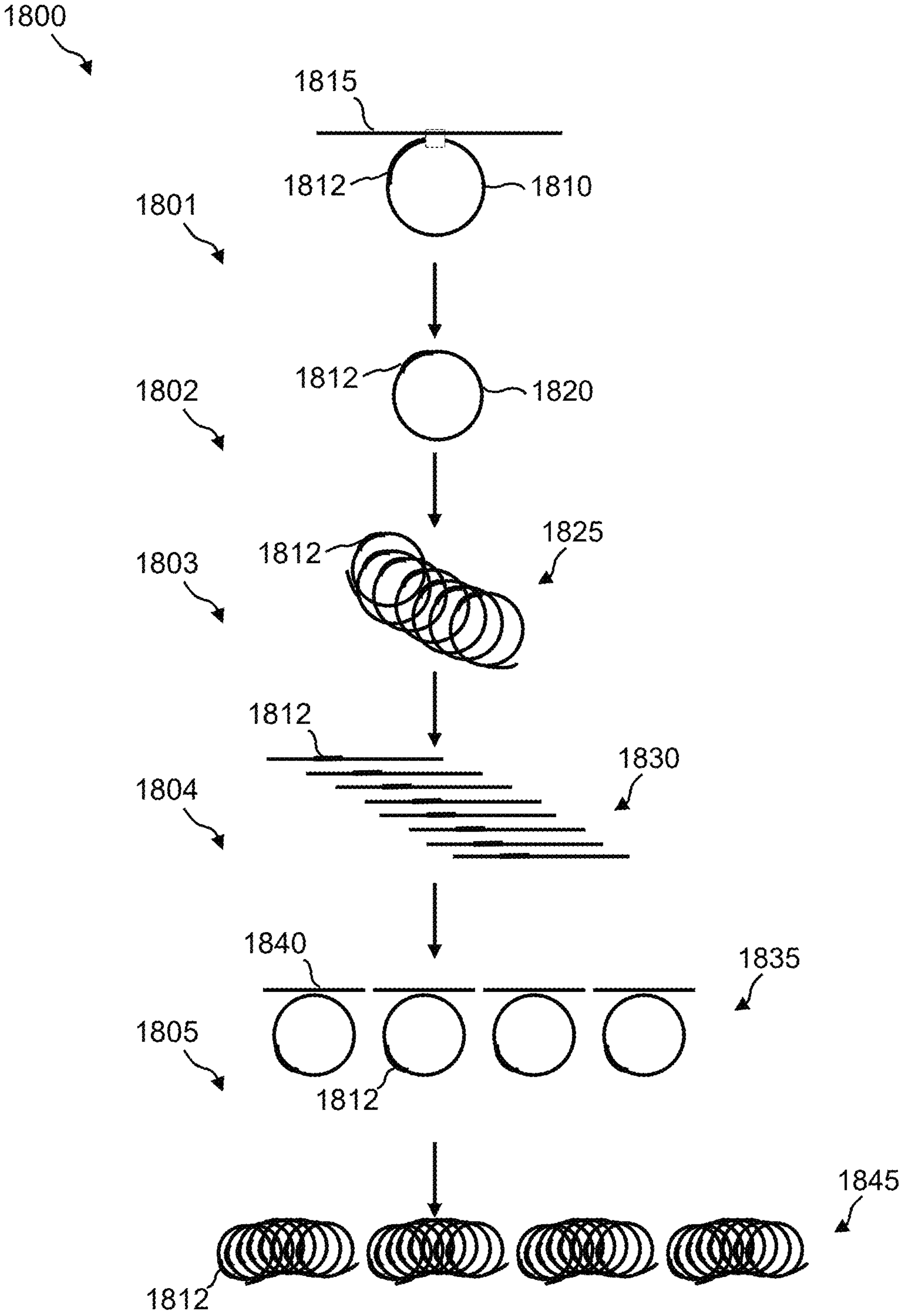
FIG. 18 is a schematic diagram of an example of an alternative process for circularizing and amplifying unit length nanoball fragments to produce multiple RCA nanoball products.

FIG. 18 is a schematic diagram of an example of an alternative process 1800 for circularizing and amplifying unit length nanoball fragments to produce multiple RCA nanoball products. Workflow 1800 may include, but is not limited to, the following steps.

In a step 1801, a probe is hybridized to a target and circularized to yield a circular modified probe. For example, a probe 1810 that includes target recognition sequences (not shown), a code 1812 and a restriction site (not shown) is hybridized to a target 1715. A ligation reaction is then performed to circularize probe 1810 to produce a circular modified probe 1820.

In a step 1802, the circular modified probe 1820 is amplified in an RCA reaction to generate a nanoball product 1825. During amplification, the restriction site is amplified into the nanoball and provides multiple sites at which to cut nanoball 1825 into fragments.

In a step 1803, the nanoball product is cleaved to produce multiple unit sized fragments each comprising the code. For example, nanoball 1825 is cleaved at the restriction sites to produce multiple unit size fragments 1830 each comprising code 1812. The cleavage reaction may, for example, be performed as describe with reference to FIG. 16.

In a step 1804, the unit size fragments are circularized to generate circular unit size fragments. For example, a splint oligonucleotide 1840 that is complementary to the target recognition sequences in unit size fragments 1830 is hybridized to the fragments and a ligation reaction is performed to generate circular unit size fragments 1835 comprising the code.

In a step 1805, the circular unit size fragments are amplified in a second RCA reaction to produce multiple nanoball copies for further processing or sequencing. For example, circular unit size fragments 1835 are amplified in an RCA reaction to produce multiple nanoballs 1845 each comprising code 1812.

Examples of sequencing techniques suitable for use with the assays disclosed herein include nanopore sequencing, next-generation sequencing, massively parallel sequencing, Sanger sequencing, sequencing by synthesis (SBS), pyrosequencing, sequencing by hybridization, single molecule real-time sequencing, SOLID, and sequencing by ligation.

In some embodiments, a process for circularizing a probe may include a gap-fill ligation reaction that may be used to circularize the probe and capture an unknown region of the target that may then be sequenced along with the code.

Figure 19:
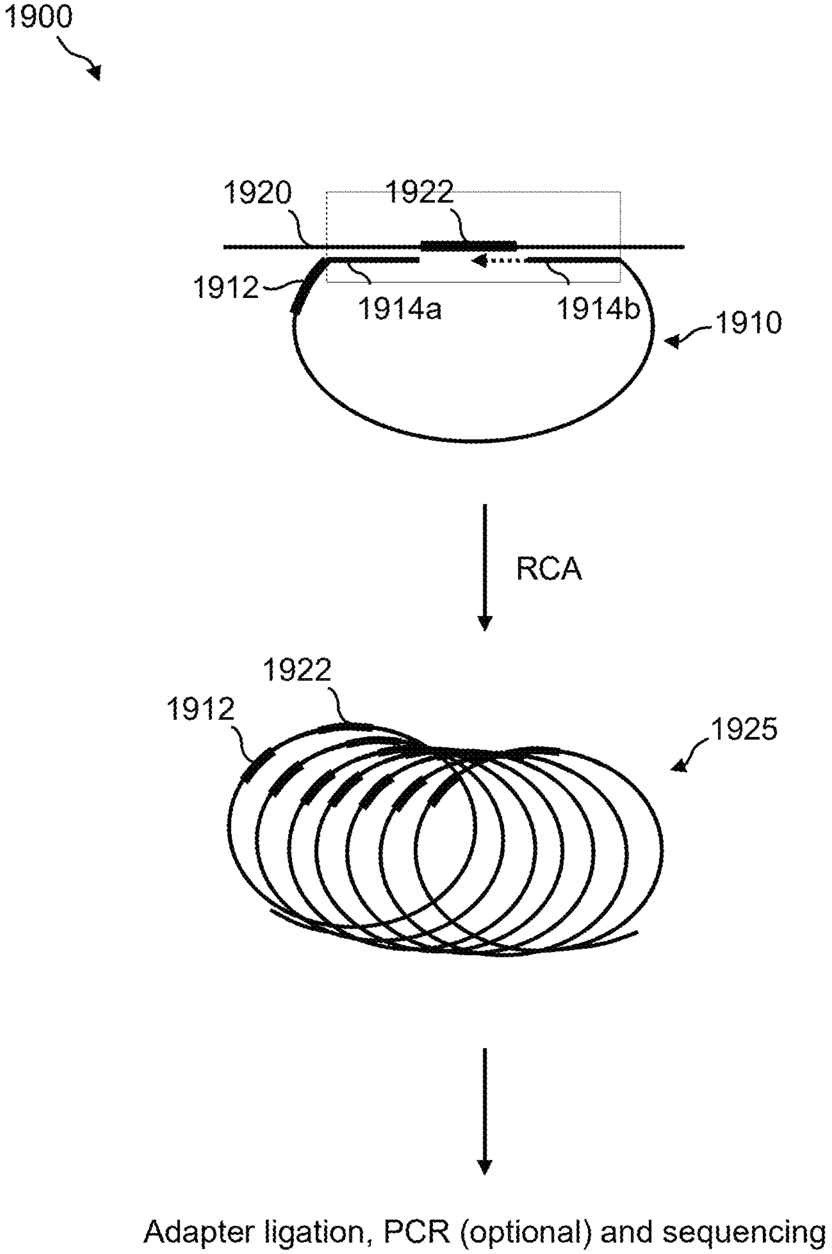
FIG. 19 is a schematic diagram of an example of a process for capturing an unknown region of a target for sequencing.

In some embodiments, an unknown region of a target sequence may be captured by a probe transformation reaction and sequenced along with the code. FIG. 19 is a schematic diagram of an example of a process 1900 for capturing an unknown region of a target for sequencing. Process 1900 may include, but is not limited to, the following steps.

In a step 1910, a probe is hybridized to a target and circularized in a gap-fill ligation reaction that captures an unknown region of the target sequence. For example, a probe 1910 that includes a code 1912 (among other elements not shown) and a pair of target recognition elements 1914 (e.g., 1914*a* and 1914*b*) is hybridized to a target analyte 1920. Target 1920 may include a region 1922 comprising an unknown sequence. Target recognition elements 1914*a* and 1914*b* recognize and bind to target 1920 at sites flanking region 1922. A gap-fill ligation reaction (indicated by dashed arrow) is performed to copy region 1922 into probe 1910 and circularize the probe to yield a circular modified probe (not shown) comprising the unknown region of target 1920. The ligation reaction may be followed by an exonuclease digestion step to remove unligated probes 1940 and target.

In a step 1915, the circular modified probe is amplified in an RCA reaction to form an RCA product 1925 comprising multiple copies of the unknown region 1922 and the code 1912 (among other sequences). The RCA product 1925 may be sequenced directly or sequencing adapter may be added by PCR amplification, followed by clustering and sequencing as described herein above.

Targeted Analyte Assay Workflow

The assays provide a readout that can be measured alongside the readout of various molecular assays that may be performed in parallel, thereby enabling a multiomic platform for the analysis of different target analytes in a sample.

Examples of target analytes include, but are not limited to, proteins, nucleic acids (e.g., DNA and RNA), metabolites, glycosylation, exosomes, viruses, bacteria, and cells (e.g., circulating tumor cells). DNA targets include single nucleotide variants (SNVs), insertion/deletions (indels), and methylated nucleotides. An RNA target may be a splice variant.

In one embodiment, an encoded assay may be performed for the analysis of a set of nucleic acid targets in a sample.

In one embodiment, the analyte is DNA. In an encoded assay, a set of DNA targets may be targeted for detection of a single nucleotide difference relative to a reference nucleotide. A single nucleotide difference may be a change in the methylation status of a nucleotide at a target site of interest. In another example, a single nucleotide difference may be a change in nucleotide usage at a target site of interest, i.e., a single nucleotide polymorphism (SNP).

In one embodiment, the analyte is RNA. In an encoded assay, an RNA sample may, for example, be processed in a reverse transcription reaction to generate cDNA molecules for detection of a set of targets of interest. An encoded RNA assay may, for example, be used to detect and count RNA targets of interest in a sample. In another example, an encoded RNA assay may be used to detect alternative splicing variants for a target of interest.

Figure 20:
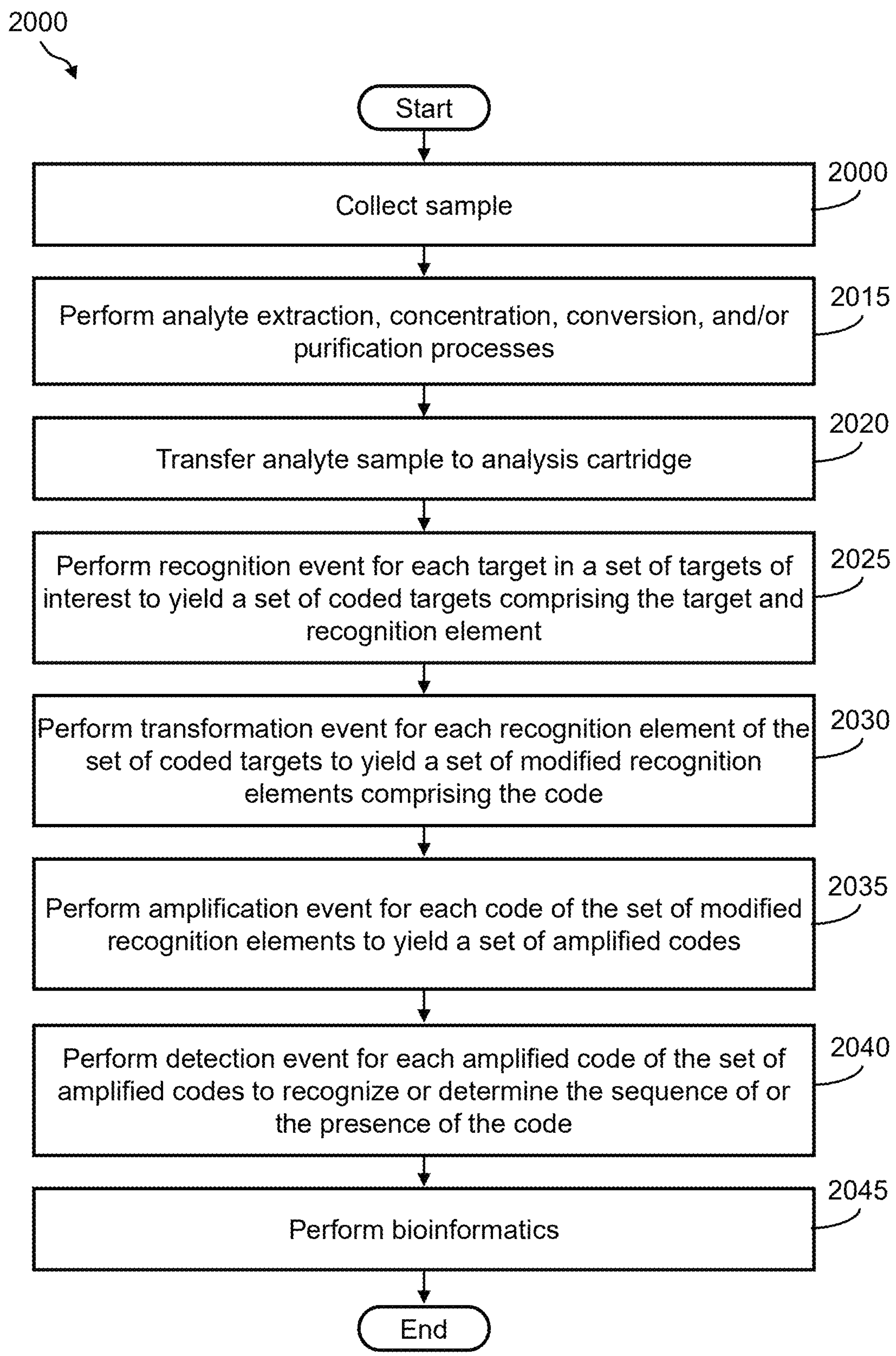
FIG. 20 is a flow diagram of an example of a targeted analyte assay workflow.

FIG. 20 is a flow diagram of an example of a target analyte assay workflow 2000. Assay workflow 2000 may include, but is not limited to, the following steps.

At a step 2010, a sample is collected. For example, a blood or saliva sample may be collected. In one example, a whole blood sample may be collected and processed to separate the plasma fraction from the cellular components of whole blood.

At a step 2015, analyte extraction, concentration, conversion, and/or purification processes are performed. In this example, the analyte is DNA. DNA (e.g., cell-free DNA) in the plasma sample may be extracted, purified, and concentrated for analysis. A proteinase K (ThermoFisher, Waltham, MA) digestion step may be used to digest proteins present in the plasma sample. In some cases, a heat denaturation step (e.g., 94-98 °C for 20-30 seconds) may be used to denature double-stranded DNA into single-stranded nucleic acid. A bead-based extraction and concentration protocol may be used to capture single-stranded DNA in the plasma sample. In some embodiments, the bead-based extraction protocol uses magnetically responsive nucleic acid capture beads. The bead-bound DNA may be released from the capture beads using an elution buffer (or other elution means suitable to the capture bead used) to produce a processed DNA sample for analysis.

In one embodiment, the DNA sample may be further processed in a bisulfite conversion reaction for analysis of the methylation status of a set of targets in the sample.

At a step 2020, the processed DNA sample is transferred into an analysis cartridge.

At a step 2025, a recognition event for each target in a set of targets is performed. For example, each target is uniquely recognized by and bound to a recognition element associated with a code (and optionally other elements). In one example, the recognition event for the set of targets uses a panel of coded padlock probes. In another example, the recognition event for the set of targets uses a panel of molecular inversion probes. The recognition event yields a set of coded targets comprising the target and the recognition element.

At a step 2030, a transformation event for each recognition element of the set of coded targets is performed. For example, in the transformation event, a ligation or a gap-fill ligation may produce the modified recognition element, i.e., a version of the recognition element that is ligated or gap-filled. In one example, transformation of a modified padlock probe in a ligation or gap-fill ligation reaction generates a circular molecule. In some cases, an exonuclease cleanup step may be used following the transformation event to digest any remaining single stranded nucleic acid, such as unreacted coded padlock probes, amplification primers, and single stranded target sequences. The transformation event yields a set of modified recognition elements comprising the code.

At a step 2035, an amplification event for each code of the set of modified recognition elements is performed. In one example, the amplification event may be a rolling circle amplification (RCA) reaction to generate a set of target-specific nanoballs. The amplification event yields a set of amplified codes (among other elements).

At a step 2040, a decoding event for each amplified code of the set of amplified codes is performed to identify the code. In one example, the code may be decoded by sequencing the code (and optionally other elements). The detection event detects the code as a surrogate for detection of the targeted analyte. Decoding by sequencing may in some cases make us of soft decoding.

At a step 2045, using the code information (and optionally other elements) from step 445, bioinformatics is performed.

In some embodiments, the amplification event (step 435) and the detection event (step 440) may be combined in a single step.

Sequencing for Target Detection

In some embodiments, of workflow 2000, a sequencing library comprising the codes (among other elements) may be generated. The library may be sequenced to identify codes associated with a target of interest. In one embodiment, a sequencing library may be generated from a circularized padlock probe (step 2030). The padlock probe library may be sequenced to identify the code associated with the target of interest.

Nanoball Sequencing Library for Target Detection

A sequencing library comprising the codes (among other elements) may be generated from a set of target-specific nanoballs (step 2035). The nanoball library may be sequenced to identify codes associated with targets of interest.

Figure 21:
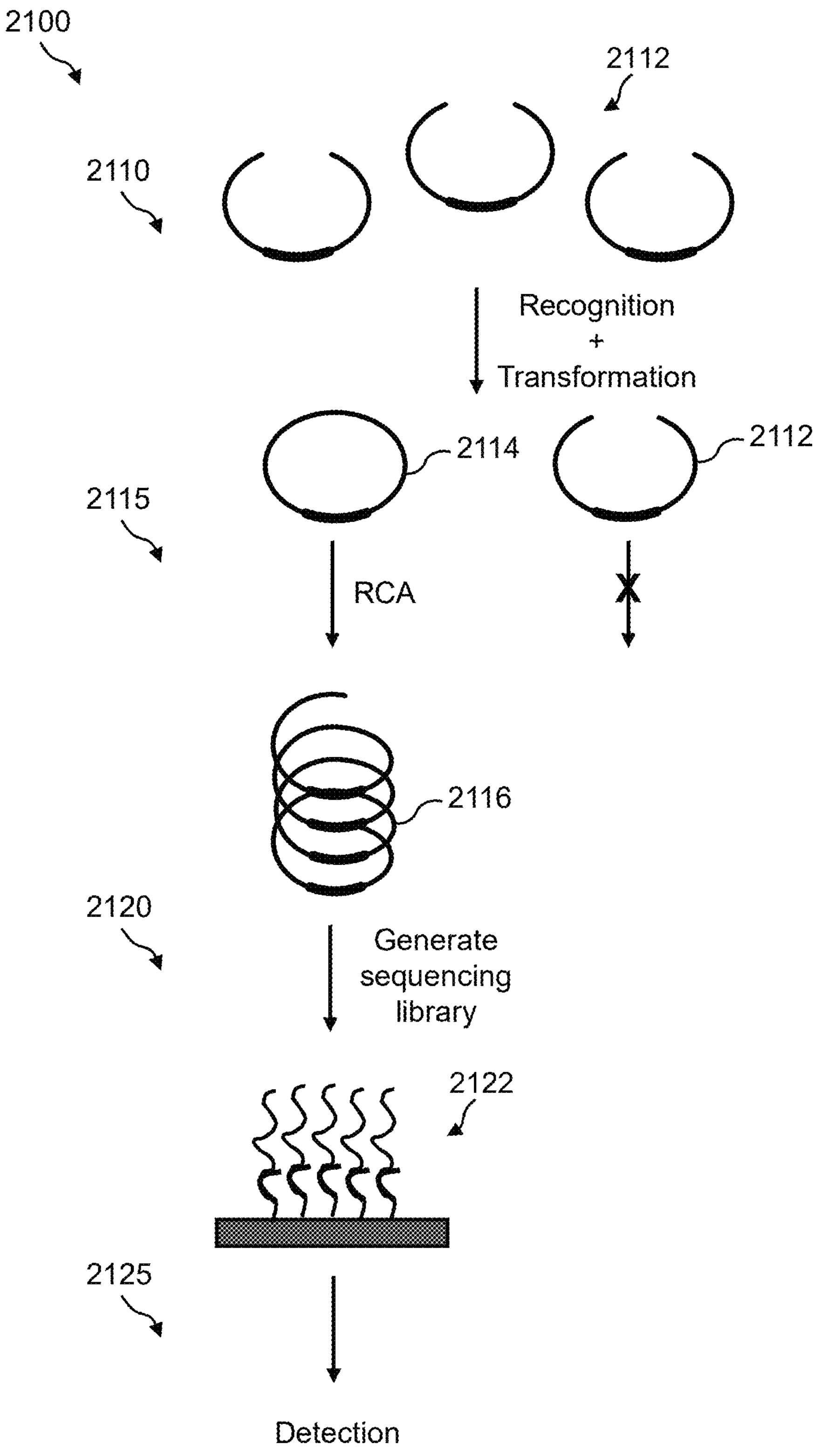
FIG. 21 is a schematic diagram illustrating an example of a process for generating a sequencing library from a nanoball set that may be used to identify the sequence of the codes associated with the target set of interest.

FIG. 21 is a schematic diagram illustrating an example of a process 2100 for generating a sequencing library from a nanoball set that may be used to identify the codes associated with the target set of interest. Sample preparation for input into process 2100 may, for example, be a performed as described for FIG. 20 starting from a whole blood sample (step 2010), performing the nucleic acid extraction, concentration, and/or purification processes (step 2015), and transferring the nucleic acid sample to the analysis cartridge (step 2020). Process 2100 may include, but is not limited to, the following steps.

In a step 2110, recognition and transformation events (steps 2025 and 2030) for each target in a set of targets of interest is performed to yield a set of modified recognition elements comprising the code. For example, a set of coded padlock probes 2112 that include target-specific recognition elements associated with a code may be used. The transformation event may include a ligation or a gap-fill ligation reaction to produce a circularized modified probe comprising the code. In the transformation event, only the coded padlock probes 2112 that hybridize to a target sequence of interest with no mismatches may be ligated to yield a circular modified probe comprising the code. In this example, a single modified probe 2114 is shown, but any number of modified probes 2114 may be generated to yield a set of modified probes 2114.

In a step 2115, an amplification event for each code of the set of modified recognition elements is performed. For example, modified probe 2114 may be amplified in a rolling circle amplification (RCA) to generate a nanoball product 2116. In this example, a single nanoball 2116 is shown, but any number of nanoballs may be generated corresponding to the number of circular modified probes present to yield a set of nanoballs comprising the codes.

In a step 2120, a sequencing library is generated from the nanoball product. For example, 25 cycles of amplification may be used to add sequencing adapters and sample index sequences (among other optional sequences) to the code sequence generating a sequencing library 2122 that includes a set of codes. Sequencing library 2122 may then loaded onto a sequencing flow cell (e.g., a MiSeq flow cell) for next generation sequencing (NGS).

In a step 2125, a detection event for each code of the set of codes is performed. For example, the library is sequenced using an NGS sequencing protocol to identify the codes (and other elements (e.g., sample index, UMIs)) associated with the set of targets of interest. The code data may then be used as a digital count of the target-specific detection events.

An example of using the NGS readout from a nanoball sequencing library for counting detection events is describe below with reference to FIG. 26 and FIG. 27.

Direct Sequencing on Nanoballs for Target Detection

A set of nanoballs (step 2035) may be directly sequenced to identify codes associated with the set of targets of interest. The code data may then be used as a digital count of the target-specific detection events.

In one embodiment, the nanoballs may be immobilized onto the surface of a sequencing flow cell for direct sequencing on the nanoballs. The nanoballs may be immobilized onto the flow cell surface using an immobilization agent. In one example, the immobilization agent is a surface bound oligonucleotide that is complementary to a sequence on the nanoball. In another example, the immobilization agent is a polypeptide.

To facilitate immobilization of a nanoball on a flow cell surface for direct sequencing, a recognition element associated with a code (i.e., an encoded probe) may include a palindrome sequence that is incorporated into the nanoball to create a secondary structure that compacts (collapses) the nanoball. The compacted nanoball provides a structure that may be more readily sequenced.

Figure 22:
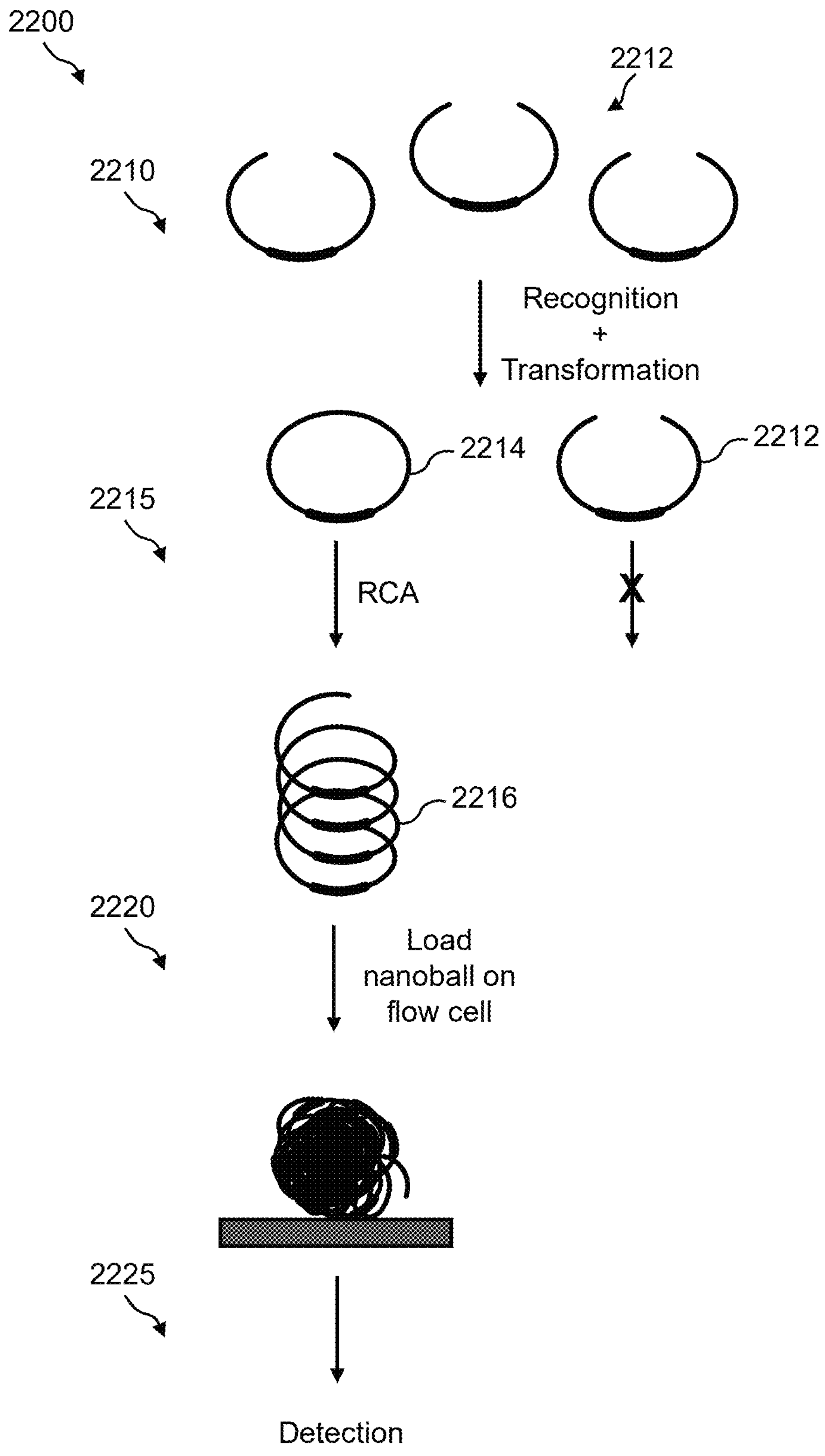
FIG. 22 is a schematic diagram illustrating an example of a process for directly sequencing a nanoball set to identify the codes associated with the target set of interest.

FIG. 22 is a schematic diagram illustrating an example of a process 2200 for directly sequencing a nanoball set to identify codes associated with the target set of interest. Sample preparation for input into process 2200 may, for example, be a performed as described for FIG. 20 starting from a whole blood sample (step 2010), performing the nucleic acid extraction, concentration, and/or purification processes (step 2015), and transferring the nucleic acid sample to the analysis cartridge (step 2020). Process 2200 may include, but is not limited to, the following steps.

In a step 2210, recognition and transformation events (steps 2025 and 2030) for each target in a set of targets of interest is performed to yield a set of modified recognition elements comprising the code. For example, a set of coded padlock probes 2212 that include target-specific recognition elements associated with a code may be used. The transformation event may include a ligation or a gap-fill ligation reaction to produce a circularized modified probe comprising the code. In the transformation event, only the coded padlock probes 2212 that hybridize to a target sequence of interest with no mismatches may be ligated to yield a circular modified probe comprising the code. In this example, a single modified probe 2214 is shown, but any number of modified probes 2214 may be generated to yield a set of modified probes 2214.

In a step 2215, an amplification event for each code of the set of modified recognition elements is performed. For example, modified probe 2214 may be amplified in a rolling circle amplification (RCA) to generate a nanoball product 2216. In this example, a single nanoball 2216 is shown, but any number of nanoballs may be generated corresponding to the number of circular modified probes present to yield a set of nanoballs comprising the codes.

In a step 2220, the nanoball product is loaded onto the surface of a sequencing flow cell. For example, nanoball product 2216 is loaded onto a MiSeq flow cell. The nanoballs may be immobilized onto the flow cell surface using an immobilization agent. In one example, the immobilization agent is a surface bound oligonucleotide that is complementary to a sequence on the nanoball. In another example, the immobilization agent is a polypeptide.

In a step 2225, a detection event for each amplified code of the set of amplified codes is performed. For example, the nanoball is directly sequenced to identify codes associated with the set of targets of interest. The code data may then be used as a digital count of the target-specific detection events.

An example of using the readout from direct nanoball sequencing for counting detection events is describe below with reference to FIG. 28 and FIG. 29.

Methylation Assays

Assays of the invention may be used to interrogate the methylation status of a target sequence of interest. In one embodiment, methylated cytosines in a target sequence of interest may be detected using assays that include a conversion reaction to detect methylated cytosines. In another embodiment, methylated cytosines in a target sequence of interest may be detected using assays that do not use a conversion reaction (i.e., conversion-free).

In one embodiment of a conversion assay for detection of methylated cytosines, a bisulfite conversion reaction that converts non-methylated cytosines to thymine (C→T) may be used.

For example, a methylated cytosine assay using encoded probes may include: (i) a bisulfite conversion reaction to convert non-methylated cytosine to thymine (C→T); (ii) a recognition event, in which a target nucleic acid is uniquely recognized and bound by a recognition element associated with a code (i.e., an encoded probe); (ii) a transformation event, in which a molecular transformation of the recognition element produces a modified recognition element comprising the code; and (iii) a detection event, that uses the code as a surrogate for detection of the target nucleic acid, e.g., by recognizing or decoding code (and optionally other elements).

In some embodiments, a methylated target site of interest may be interrogated using an encoded probe in combination with a transformation event that includes a ligation reaction to detect the methylation status of the target site.

In one embodiment, the recognition element (i.e., an encoded probe) may be a coded padlock probe that includes a 3'-terminal guanine ("G"). The transformation event (i.e., ligation) to generate the modified recognition element may only occur when the 3'-guanine is matched to a cytosine at a target site of interest.

Figure 23:
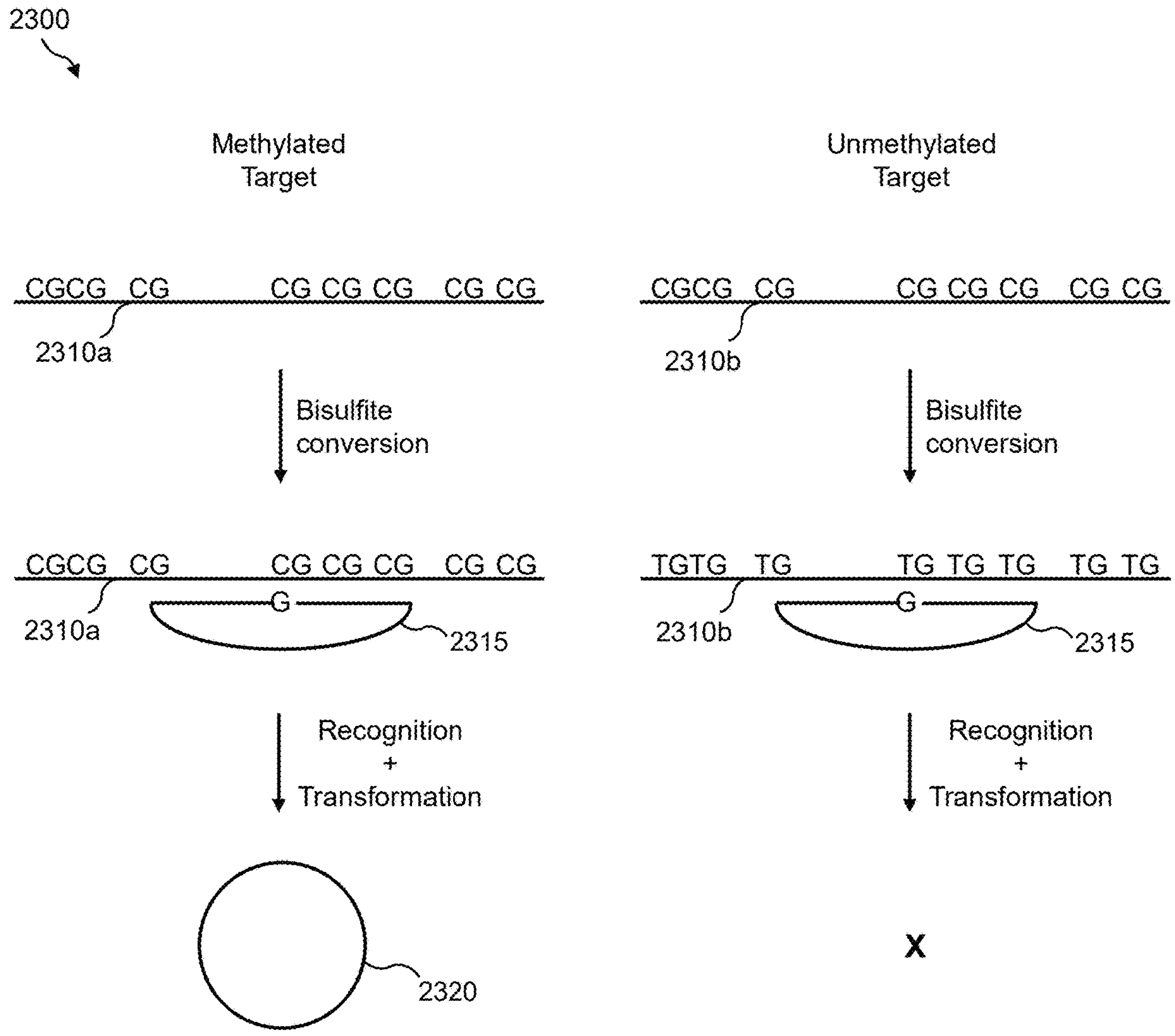
FIG. 23 is a schematic diagram illustrating an example of a process of using a bisulfite conversion reaction in combination with a coded padlock probe to detect a methylated target site of interest.

FIG. 23 is a schematic diagram illustrating an example of a process 2300 of using a bisulfite conversion reaction in combination with a coded padlock probe to detect a methylated target site of interest. In this example, a DNA sample may include a target sequence of interest 2310 that may be methylated (e.g., 2310*a* "Methylated Target") or unmethylated (e.g., 2310*b* "Unmethylated Target") at a CpG site of interest. A bisulfite conversion reaction is used to convert non-methylated cytosine to thymine (C→T) in the target sequence 2310*b*.

In the recognition event, target sequence 2310 is recognized and bound by a recognition element associated with a code, i.e., padlock probe 2315. Padlock probe 2315 includes a 3'-terminal G nucleotide that base pairs with the target C at the CpG site of interest.

In the transformation event, ligation of padlock probe 2315 only occurs when the 3'-terminus of the padlock probe (i.e., a guanine "G") is matched to the target site "C" of interest in target sequence 2310*a* to generate a circularized modified padlock probe 2320. No ligation occurs at the target site "T" in the bisulfite converted target sequence 2310*b* and consequently, transformation of padlock probe 2315 hybridized to target sequence 2310*b* to a circular modified probe does not occur. As described above with reference to FIG. 20, modified padlock probe 2320 may be amplified in an RCA reaction to generate a nanoball product (step 2035; not shown) comprising many copies of the code (among other elements) and the code may be decoded (step 2040).

In one embodiment of process 2300, the recognition element (i.e., encoded probe) may be a molecular inversion probe that includes a 3'-terminal single base gap at a target site of interest. A gap-fill ligation event using only a single added nucleotide may be used to generate the modified recognition element comprising the code only when the nucleotide corresponding to the target site of interest is incorporated. This approach provides two forms of specificity to the assay: (i) the 3'-terminus of the probe must recognize and bind the interrogated site; and (ii) a single base extension reaction that incorporates the nucleotide corresponding to the target site of interest occurs.

Figure 24:
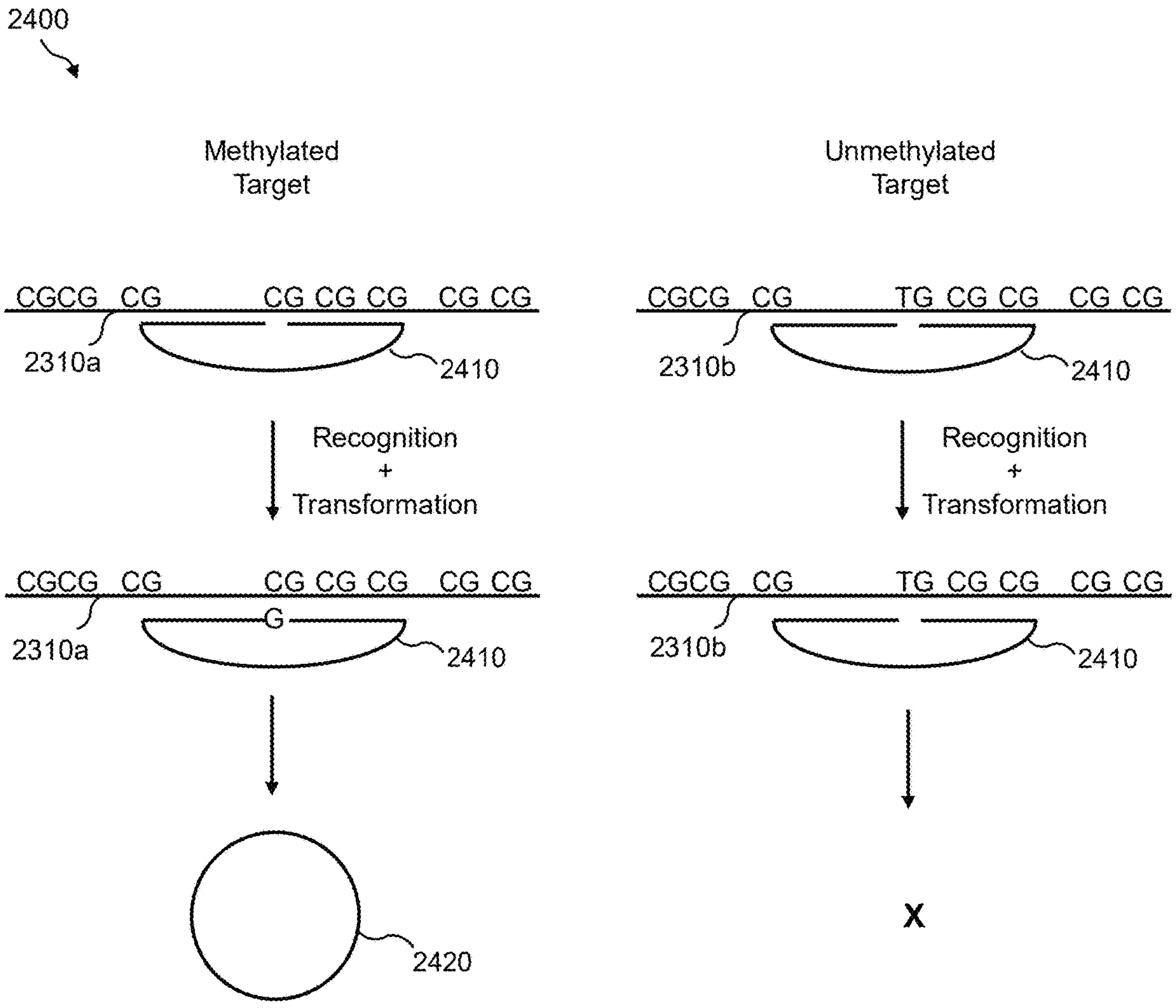
FIG. 24 is a schematic diagram illustrating an example of a process of using a bisulfite conversion reaction in combination with a coded molecular inversion probe to detect a methylated target site of interest.

FIG. 24 is a schematic diagram illustrating an example of a process 2400 of using a bisulfite conversion reaction in combination with a coded molecular inversion probe to detect a methylated target site of interest. In this example, a DNA sample may include a target sequence of interest 2310 that may be methylated (e.g., 710*a* "Methylated Target") or unmethylated (e.g., 2310*b* "Unmethylated Target") at a CpG site of interest. A bisulfite conversion reaction is used to convert non-methylated cytosine to thymine (C→T) in the target sequence 2310*b*.

In the recognition event, target sequences 2310*a* and 2310*b* are recognized and bound by a recognition element associated with a code, i.e., molecular inversion probe 2410. Molecular inversion probe 2410 includes a single 3'-terminal base gap that spans a target site of interest.

In the transformation event, a single dGTP nucleotide ("G") is incorporated in molecular inversion probe 2410, thereby allowing ligation of the probe to generate a circularized modified probe 2420. No incorporation of dGTP occurs at the target site "T" in the bisulfite converted target sequence 2310*b* and consequently, transformation of molecular inversion probe 2410 hybridized to target sequence 2310*b* to a circular modified probe does not occur. As described above with reference to FIG. 20, modified probe 2420 may be amplified in an RCA reaction to generate a nanoball product (step 2035; not shown) comprising many copies of the code (among other elements) and the code may be decoded (step 2040).

In one embodiment of process 2400, the recognition element (i.e., a molecular inversion probe) may be designed to target two methylated cytosine sites of interest in a target sequence of interest. A gap-fill ligation event using all dNTPs may be used to generate the modified recognition element comprising the code. In this approach, both methylated cytosines must be present in the target nucleic acid molecule for ligation to occur. The requirement for multiple matches has several advantages: (i) it provides enhanced specificity relative to a single match at a methylated cytosine; (ii) the ability to discriminate between a disease state (e.g., all CpG sites in a region are methylated) and a healthy state (e.g., only some CpG sites are methylated) is increased by requiring multiple methylated cytosines for detection; and (iii) multiple matches can be used to correct for incomplete bisulfite conversion of unmethylated cytosines at the target site of interest.

Figure 25:
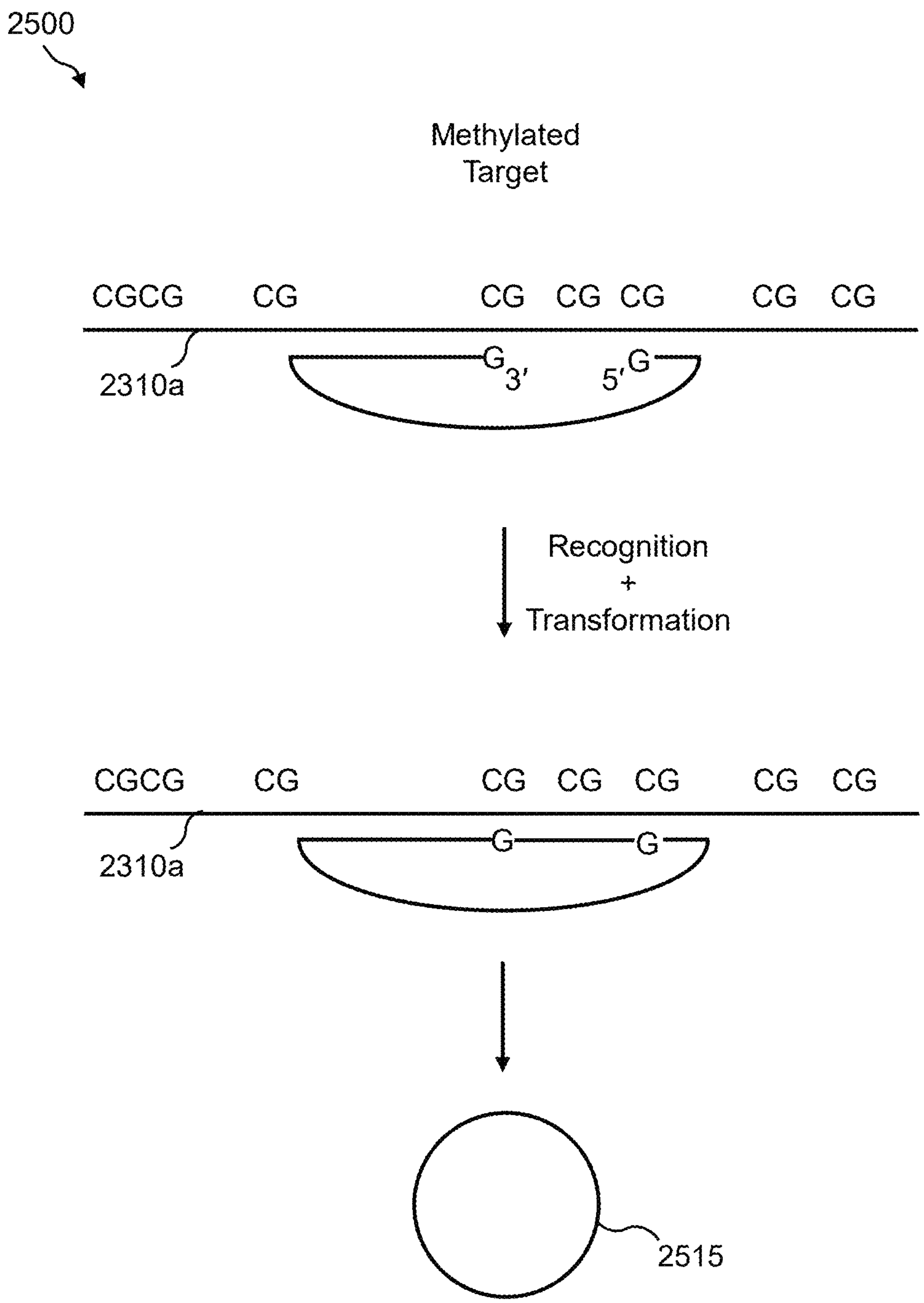
FIG. 25 is a schematic diagram illustrating an example of a process of using a recognition element that targets two methylated cytosines in a target of interest.

FIG. 25 is a schematic diagram illustrating an example of a process 2500 of using a recognition element that targets two methylated cytosines in a target of interest. A DNA sample may include a target sequence of interest 2310 that may be methylated at multiple CpG sites. In this example, only the methylated target sequence 2310 is shown. A bisulfite conversion reaction is used to convert non-methylated cytosine to thymine (C→T) in the target sequence (not shown).

In the recognition event, target sequences 2310 is recognized and bound by a recognition element associated with a code, i.e., molecular inversion probe 2515. Molecular inversion probe 2515 includes a 3'-probe arm that terminates at a first methylated cytosine site and a 5'-probe arm that terminates at a second methylated cytosine site. Both a 3'-GC match and a 5'-GC match during the recognition event (hybridization) are required for a transformation event to occur.

In the transformation event, a gap-fill ligation reaction using all dNTPs is performed. The 3'-GC match is required for polymerase extension in the gap-fill reaction. The 5'-GC match is required for ligation of the gap-filled molecule. Gap-fill ligation generates a circularized modified probe 2515. No incorporation of dGTP occurs at the target site "T" in the bisulfite converted target sequence (not shown) and consequently, transformation to a circular modified probe does not occur in non-methylated target sequences. As described above with reference to FIG. 20, modified probe 2515 may be amplified in an RCA reaction to generate a nanoball product (step 2035; not shown) comprising many copies of the code (among other elements) and the code may be decoded (step 2040).

Genotyping Assays

The assays of the invention may be used in a genotyping assay. A target site of interest may be interrogated using an encoded probe in combination with a ligation reaction to detect a single nucleotide variant (SNV) of interest. In one example, the single nucleotide change may be a single nucleotide polymorphism (SNP).

In one embodiment, a genotyping assay using encoded probes may include: (i) a recognition event, in which a target nucleic acid is uniquely recognized and bound by a recognition element associated with a code (i.e., an encoded probe); (ii) a transformation event, in which a molecular transformation of the recognition element produces a modified recognition element comprising the code; and (iii) a detection event, that uses the code as a surrogate for detection of the target nucleic acid, e.g., by recognizing or decoding code (and optionally other elements).

In one embodiment, the recognition element (i.e., an encoded probe) may be a coded padlock probe that includes a 3'-terminal nucleotide that is matched to a SNV of interest. The transformation event (i.e., ligation) to generate the modified recognition element may only occur when the 3'-nucleotide is matched to the SNV at the target site of interest.

In one embodiment, the recognition element (i.e., an encoded probe) may be a molecular inversion probe that includes a 3'-terminal single base gap at a target site of interest. A gap-fill ligation event using only a single added nucleotide may then be used to generate the modified recognition element comprising the code only when corresponding nucleotide is incorporated.

RNA Assays

The assays of the invention may be used in an RNA analysis assay.

In one embodiment, an RNA assay using encoded probes may include: (i) a reverse transcription reaction to convert RNA (e.g., polyA RNA) to cDNA; (ii) a recognition event, in which a target nucleic acid is uniquely recognized and bound by a recognition element associated with a code (i.e., an encoded probe); (ii) a transformation event, in which a molecular transformation of the recognition element produces a modified recognition element comprising the code; and (iii) a detection event, that uses the code as a surrogate for detection of the target nucleic acid, e.g., by recognizing or decoding code (and optionally other elements).

In some cases, the reverse transcription step (i) may be omitted and a ligase tolerant to DNA-RNA hybrid duplexes may be used in the transformation event. In one example, the ligase is SplintR® ligase (New England BioLabs).

In one embodiment, the encoded probe may be a padlock probe that includes a recognition element associated with a code.

In one embodiment, the encoded probe may be a molecular inversion probe that includes a recognition element associated with a code.

Assays of the invention may be used to detect and count RNA targets of interest in a sample.

Assays of the invention may be used to detect alternative splicing variants for a target of interest. In one example, splicing variants may be identified by placing one half of a recognition element (e.g., a coded padlock probe) on either side of the splice site. The transformation event (i.e., ligation) to generate the modified recognition element may only occur when the 3'-nucleotide is matched to the splice variant at the target site of interest.

In another example, splicing variants may be identified using a molecular inversion probe and an extension ligation reaction, wherein one probe arm spans the splice site.

Applications

Samples

Examples of tissues from which nucleic acid may extracted using the techniques described herein may include solid tissue, lysed solid tissue, fixed tissue samples, whole blood, plasma, serum, dried blood spots, buccal swabs, other forensic samples, fresh or frozen tissue, biopsy tissue, organ tissue, cultured or harvested cells, and bodily fluids.

In various embodiments, a sample may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes.

Samples may be provided directly from biological sources, or may be processed samples, such as samples which are enriched for targets, nucleic acids, or proteins from any of the foregoing sources.

Targets

The assays provide a readout that can be measured alongside the readout of various molecular assays that may be performed in parallel, thereby enabling a multiomic platform for the analysis of different target analytes in a sample. Examples of target analytes include, but are not limited to, proteins, nucleic acids (e.g., DNA and RNA), metabolites, glycosylation, exosomes, viruses, bacteria, and cells (e.g., circulating tumor cells). DNA targets include single nucleotide variants (SNVs), insertion/deletions (indels), and methylated nucleotides. An RNA target may be a splice variant.

Targets may include any biological markers. Examples include biological markers for screening or diagnosing cancer. In one embodiment, targets include a panel of methylation markers for diagnosing cancer. Examples of panels of probes which may be targeted are set for the in WO2019195268, entitled "Methylation markers and targeted methylation probe panels," and WO2020069350A1, entitled "Methylation markers and targeted methylation probe panel," the entire disclosures of which (including without limitation the sequence listings) are incorporated herein by reference. Targets may be obtained from biopsies, circulating nucleic acid samples, or nucleic acids from other samples.

In one embodiment, targets include a panel of single nucleotide variants (SNV) for diagnosing cancer.

Diagnostics and Screening

The methods of the invention may be used for screening or diagnosing a subject for a disease, such as cancer or for selecting a therapy for treating a disease, such as selecting a therapy for treating a cancer.

In one embodiment, the methods of the invention may be used in a liquid biopsy application. In one example, a liquid biopsy assay may include determination of the methylation status and/or the variant usage of a set of target sequences.

In one embodiment, the methods of the invention may be used in a pathogen detection application. In one example, pathogen detection may include detect both a protein and nucleic acid (e.g., an RNA) associated with the pathogen.

In one embodiment, the methods of the invention may be used to monitor and/or determine complications associated with a transplantation procedure.

Examples

A sequencing library may be generated from a set of target-specific nanoballs. The nanoball library may be sequenced to decode the code associated with the target of interest. The sequence analysis may include, for example, demultiplexing sample indexes, bin code sequences, and filter the data based on UMIs. The code data may then be used as a digital count of the target-specific detection events.

To evaluate detecting target sequences using a nanoball library and NGS sequencing, methylation assay was performed. Nanoball libraries were generated using a synthetic DNA sample comprising 8 methylated or unmethylated target sequences. The experimental conditions were as follows: (i) the input target concentrations were 1, 10, 100, or 1000 fM; (ii) the total target probe concentration was 2 nM; (iii) 8 target-specific probes were used, each at 250 pM; and (iv) for each input target concentration, the recognition event (i.e., target and probe hybridization; at 65 °C for 15 minutes), an exonuclease cleanup step, and the amplification event (i.e., an RCA reaction) were performed in a single tube by the sequential addition of reaction reagents.

Figure 26:
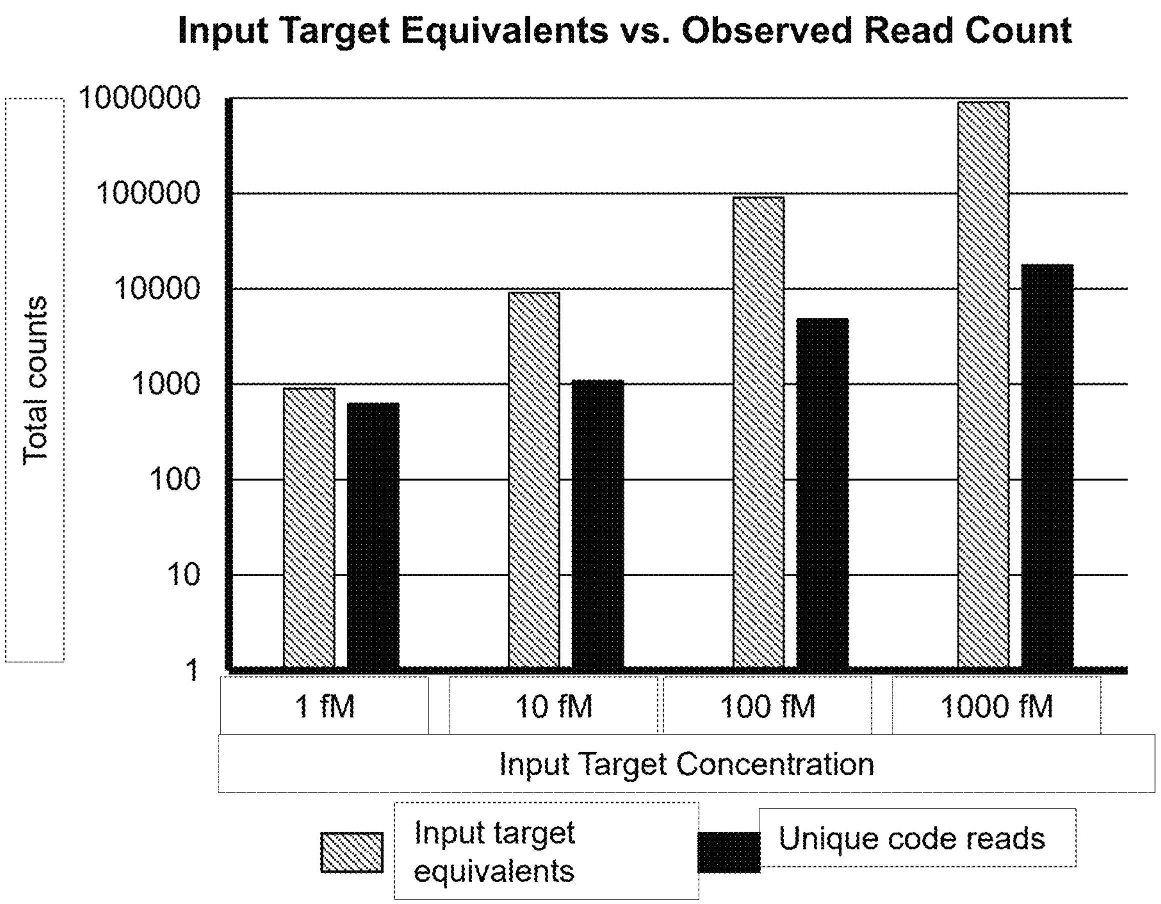
FIG. 26 is a graph showing the input target equivalents vs. observed read count for the nanoball libraries generated using a synthetic DNA sample comprising 8 target sequences.

FIG. 26 is a plot 2600 showing the input target equivalents vs. observed read count for the nanoball libraries generated using a synthetic DNA sample comprising 8 target sequences. The hatched bars show the input target equivalents, which is the number of counts expected based on the number of targets present in the sample. The black bars show the unique code reads, which is the number of counts observed. The data show that at lower input concentrations, the assay is efficient and detects about 70% of the input targets. As the input concentration of targets increases, the number of counts increases, but the detection percentage is less. This observation may be due to the excess probe concentration in the lower target input library preparation reaction. Sensitivity of the NGS assay was demonstrated down to 1,000 copies of target molecules.

To evaluate the specificity of the NGS assay (i.e., on-target vs. off-target performance), the same data set was used, but additional samples were used that add either no targets present (i.e., background sample) or an excess of non-methylated target (Me (−)).

Figure 27:
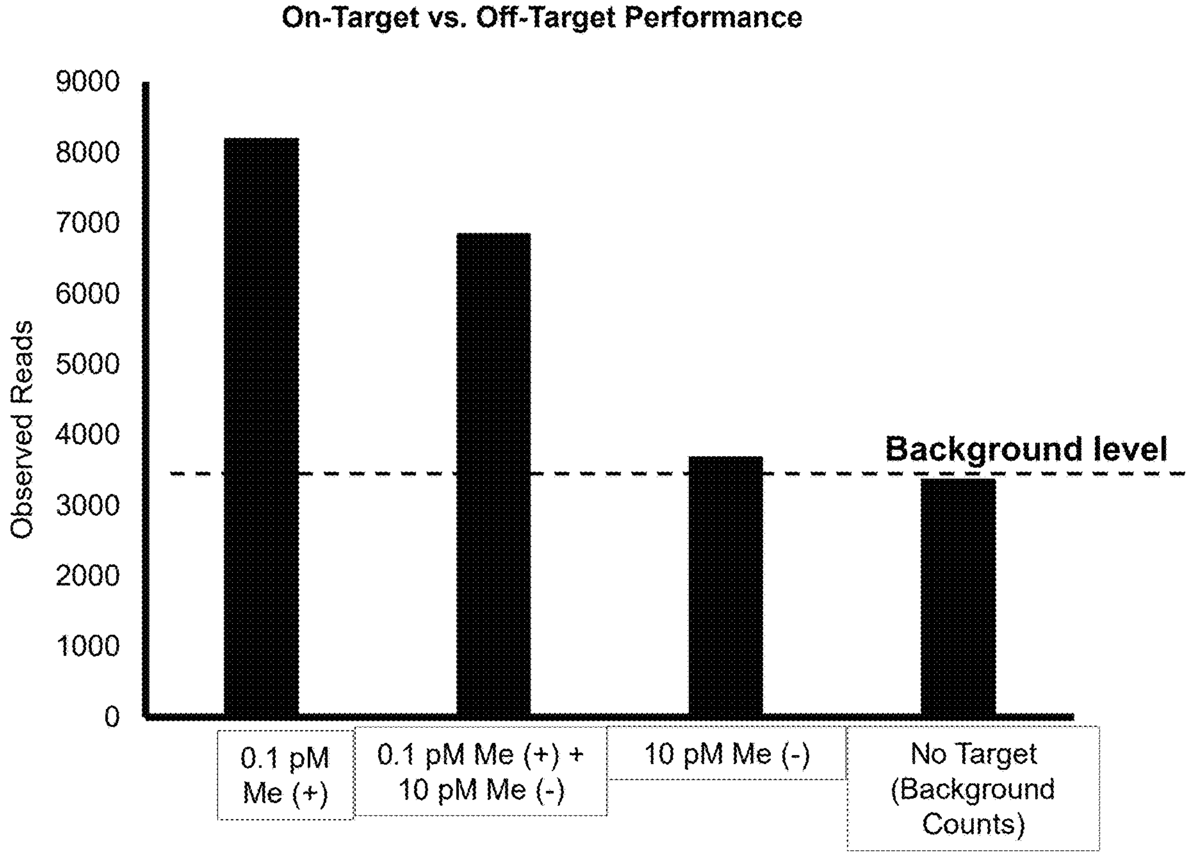
FIG. 27 is a graph showing the on-target vs. off-target performance of the NGS assay.

FIG. 27 is a plot 2700 showing the on-target vs. off-target performance of the NGS assay. The data show that in the background sample ("No Target") some counts were observed, which may be due to the amplification steps performed prior to loading the samples onto a sequencing flow cell. For the non-methylated target (10 PM Me (−)), a low level of signal was observed above the background signal. At 0.1 pM of the methylated target (Me (+)), which is a 100-fold lower concentration that the Me (−) target, the observed reads are significantly increased. This observation demonstrates that the methylated target was detected and that the assay is specific. In a mixture of 0.1 pM Me (+) and 10 pM Me (−) targets, the methylated target (Me (+)) was still detected. The data show that the NGS assay performs well when an excess of non-methylated target is present, albeit the conversion efficiency is lower probably due to probe off-target effects.

Referring now to FIG. 26 and FIG. 27, the data show that NGS readout with UMIs allows for counting of detection events.

A set of nanoballs may be directly sequenced to identify codes associated with the set of targets of interest. The nanoballs may be immobilized onto a flow cell surface using an immobilization agent and then sequenced. The code data may then be used as a digital count of the target-specific detection events.

Figure 28A:
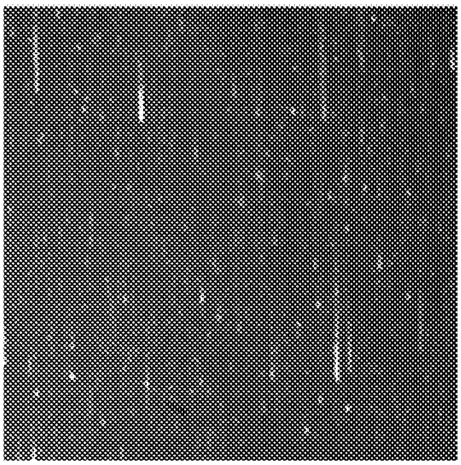
FIG. 28A is a photo showing features on a flow cell surface generated by nanoballs comprising a "standard" recognition element immobilized using an oligonucleotide.
Figure 28B:
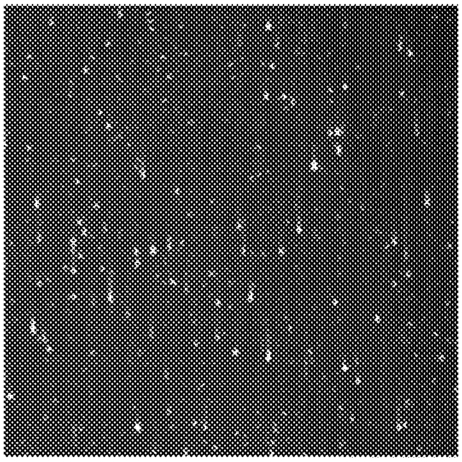
FIG. 28B is a photo showing features on a flow cell surface generated by nanoballs comprising a recognition element that includes a palindrome sequence (i.e., a "palindrome" recognition element) immobilized using an oligonucleotide.
Figure 28C:
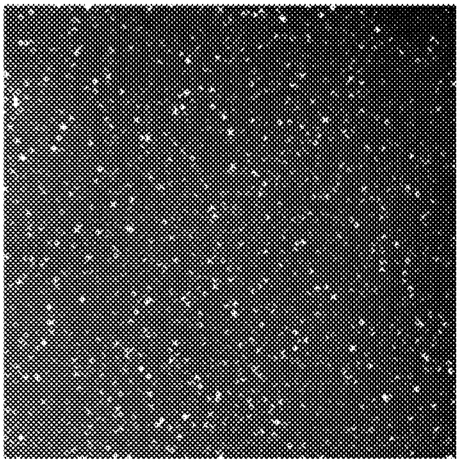
FIG. 28C is a photo showing features on a flow cell surface generated by nanoballs comprising a palindrome sequence (i.e., a "palindrome" recognition element) immobilized using a polypeptide.

FIG. 28 is a panel of photos A, B, and C showing features on a flow cell surface generated by nanoballs comprising a "standard" recognition element or a recognition element that includes a palindrome sequence (i.e., a "palindrome" recognition element) immobilized using different immobilization agents. Photo A shows the features on a flow cell surface during sequencing of nanoballs generated using a standard recognition element ("Probe") and immobilized on the flow cell surface by hybridization to a complementary oligonucleotide ("Oligo-immobilization"). Photo B shows the features on a flow cell surface during sequencing of nanoballs generated using a palindrome recognition element ("Palindrome probe") and immobilized on the flow cell surface by hybridization to a complementary oligonucleotide. Photo C shows the features on a flow cell surface during sequencing of nanoballs generated using a palindrome recognition element and immobilized on the flow cell surface with a polypeptide.

Referring now to photo A, the individual features generated from nanoballs that include the standard recognition element and are immobilized on the flow cell surface via oligonucleotide hybridization appear spread out, i.e., as streaks. This streaking of the features may be due to the unrolling of the nanoballs on the surface of the flow cell.

Referring now to photo B, the features generated from nanoballs that include the palindrome sequence and are immobilized on the flow cell surface via oligonucleotide hybridization appear more punctate, but still display some streaking. The density of features achieved using this approach was about 23k nanoballs/$mm^2$.

Referring now to photo C, the features generated from nanoballs that include the palindrome sequence and are immobilized on the flow cell surface via the polypeptide are more punctate, i.e., more compacted. The density of features achieved using this approach was about 110k nanoballs/$mm^2$. The compacted nanoballs on the flow cell surface provide a nanoball structure that may be more readily sequenced.

Sequencing on nanoballs allows counting of detection events. To demonstrate that the input target concentration directly correlates with the number of counts, a titration experiment was performed. Briefly, nanoballs were generated using one target sequence at a range of input concentrations (i.e., 100 pM, 10 pM, 1 pM, or no target (0 pM)) and 8 probes for methylation sites. Following the recognition and transformation events (i.e., hybridization and ligation), an exonuclease cleanup reaction was performed prior to performing the amplification event (i.e., an RCA reaction) to generate nanoballs. The nanoballs were then loaded onto a MiSeq flow cell and sequenced.

Figure 29A:
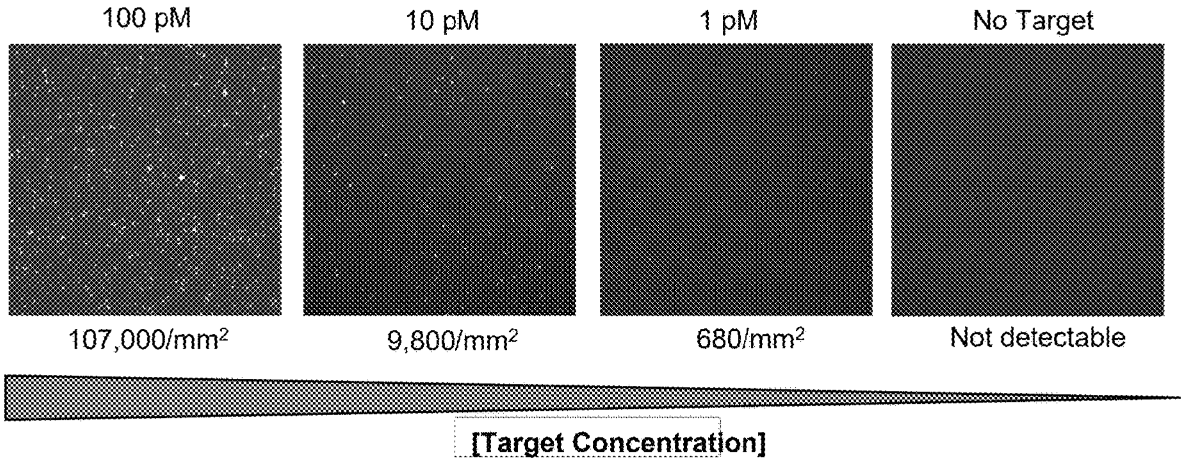
FIG. 29A is a panel of photos showing the correlation of input target concentration on the number of detection event counts from sequencing on nanoballs.
Figure 29B:
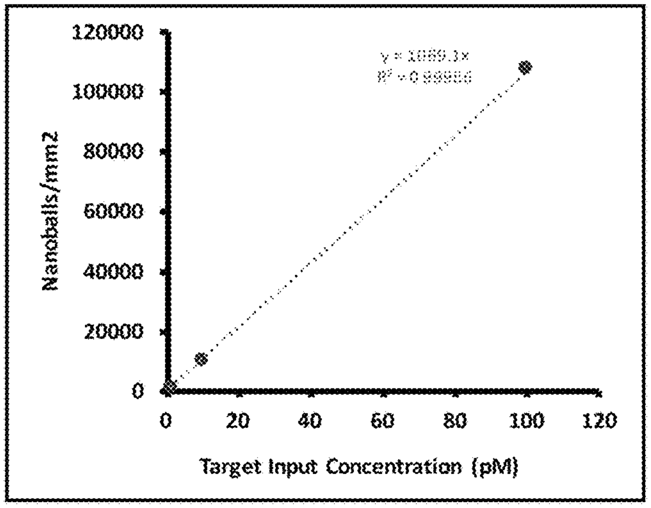
FIG. 29B is a plot showing the correlation of input target concentration on the number of detection event counts from sequencing on nanoballs.

FIG. 29A and FIG. 29B are a panel of photos 2900 and a plot 2910, respectively, showing the correlation of input target concentration to the number of detection event counts from sequencing on nanoballs. The data show that as the target concentration is titrated down from 100 to 1 pM, the number of detection event counts is linearly dependent on the target concentration.

Figure 30A:
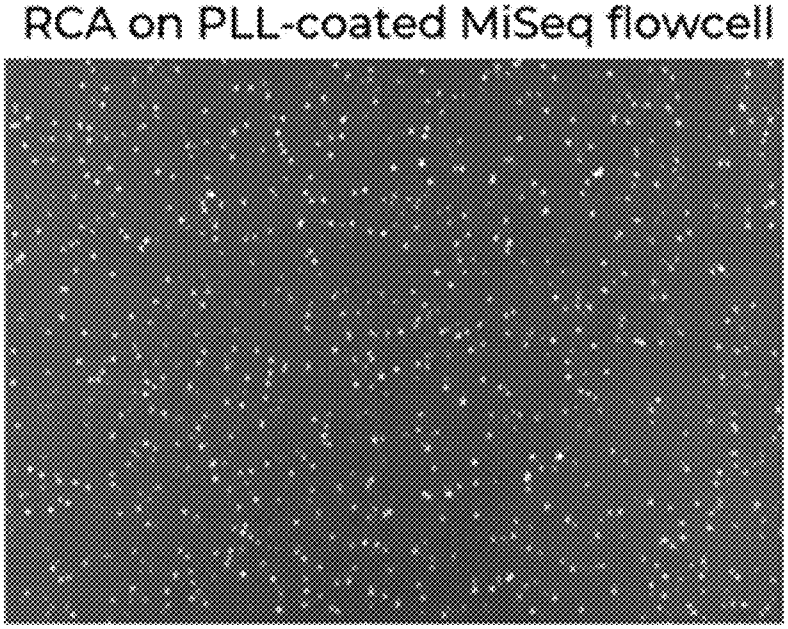
FIG. 30A is a photo showing the density, size and uniformity of nanoballs generated in an RCA reaction performed on a polylysine-coated MiSeq flow cell.
Figure 30B:
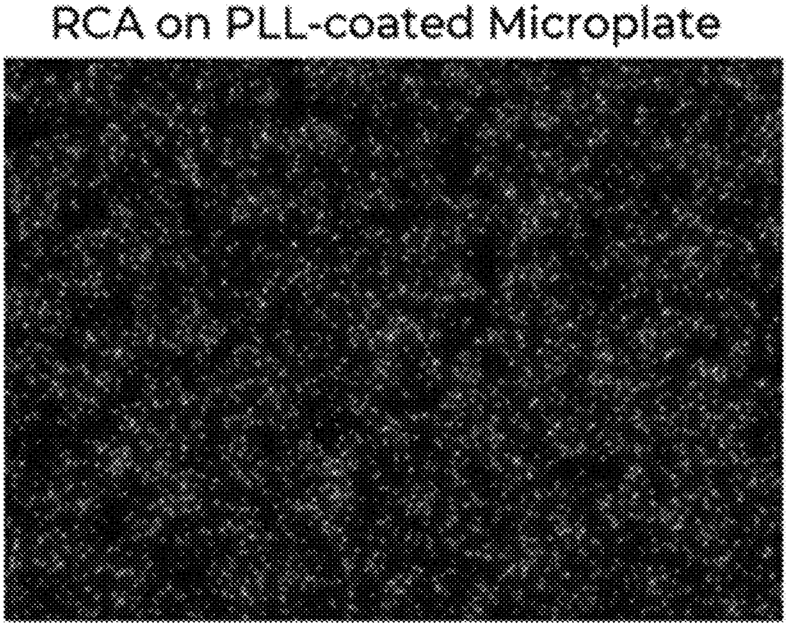
FIG. 30B is a photo showing the density, size and uniformity of nanoballs generated in an RCA reaction performed on a polylysine-coated microplate.

FIG. 30A and FIG. 30B are photos showing the density, size and uniformity of nanoballs generated in an RCA reaction performed on a polylysine-coated MiSeq flow cell or on a polylysine-coated microplate, respectively. In this example, RCA was performed as follows: RCA on Polylysine surface: MiSeq flowcells were washed to remove surface coatings before 0.01% poly-lysine (PLL) was applied, incubated for 30 minutes, washed and dried. PLL-coated microplates are assembled using purchased PLL-coated glass coverslips and plastic multi-well chambers. RCA reactions are prepared normally in tubes on ice containing phi29 polymerase, buffer, a primer and ligated purified probes, and the complete reaction is applied to the flowcell or microplate. The flowcell or microplate was incubated at 30 C for 6-8 hours, and then washed with Tris/EDTA to stop the reaction. NBs were detected with different methods. The NBs on the MiSeq flowcell were detected by SBS using a MiSeq instrument while the NBs on the microplate surface were hybridized with a fluorophore-labeled oligonucleotide probe and imaged on a Lionheart automated microscope.

Figure 31A:
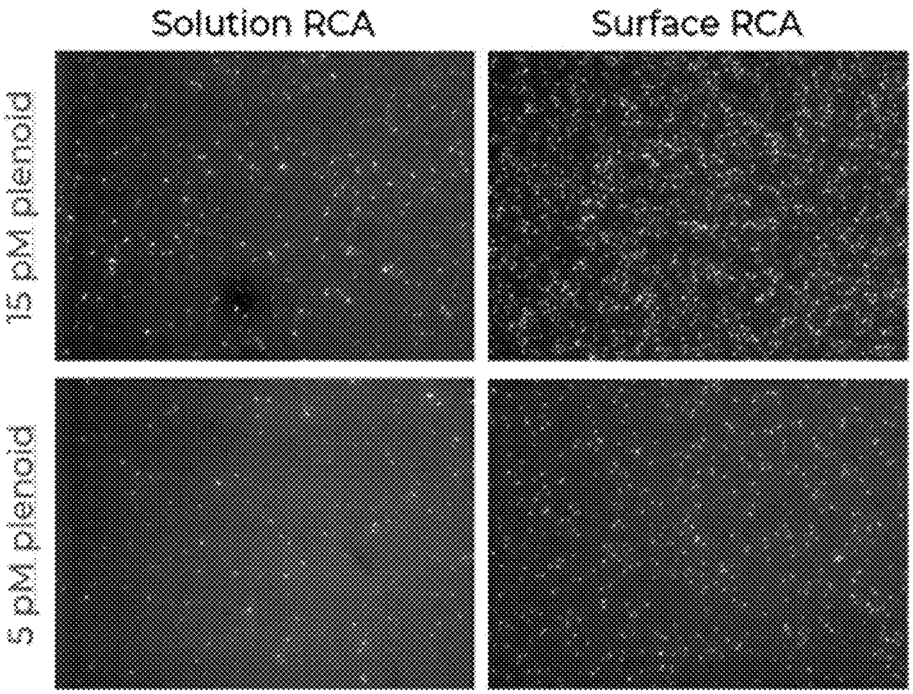
FIG. 31A is a panel of photos of a comparison of nanoballs generated on a polylysine surface to nanoballs absorbed to a surface after an RCA solution reaction.
Figure 31B:
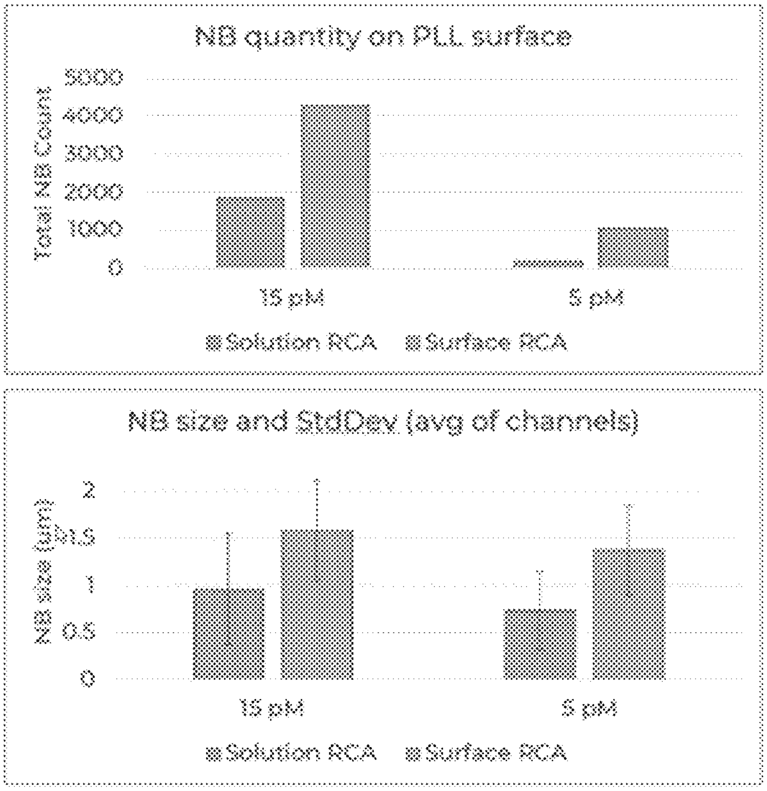
FIG. 31B is a pair of plots of a comparison of nanoballs generated on a polylysine surface to nanoballs absorbed to a surface after an RCA solution reaction.

FIGS. 31A and 31B are panel of photos and a pair of plots, respectively, of a comparison of nanoballs generated on a polylysine (PLL) surface to nanoballs absorbed to a surface after an RCA solution reaction. In this example, surface vs solution RCA reactions were performed as follows: RCA reactions were prepared normally in tubes on ice containing phi29 polymerase, buffer, a primer and either 5 pM or 15 pM ligated purified probes. A fraction of the RCA reactions was applied to different wells of a microplate with a PLL-coated bottom surface, and then the plate was incubated at 30 C for 4 hours. The remainder of the RCA reactions in tubes were placed at 30 C for 4 hours. The RCA reactions in the microplate were stopped by washing with Tris/EDTA. EDTA and TBS were added to the RCA reactions in tubes and fluorophore-labeled oligonucleotide probes were also added before the reactions were applied to the PLL-coated microplate and allowed to absorb for 1 hr. Fluorophore-labeled oligonucleotide probes in TBS were also applied to the wells in which the RCA was performed in the microplate for specific detection of NBs. After washing, all wells were imaged on a Lionheart automated microscope and analyzed with Lionheart software.

Soft Decoding

A soft decoding process may use decoding by hybridization (DBH).

Figure 32:
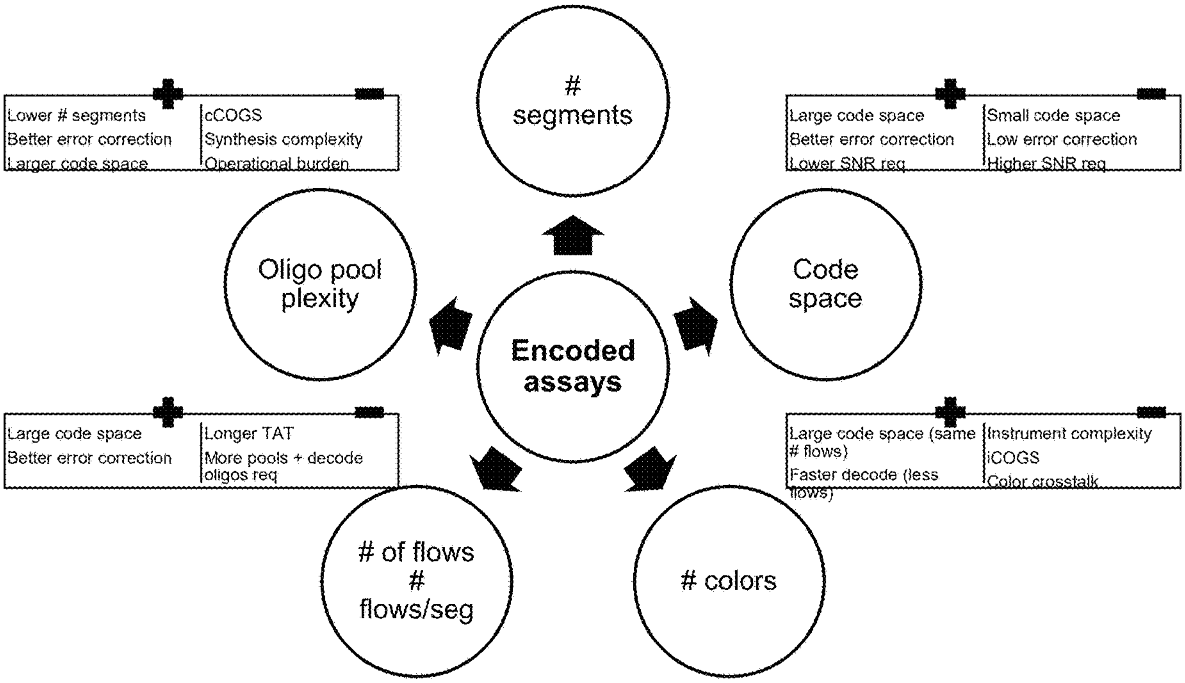
FIG. 32 is a schematic diagram illustrating some of the factors considered in the design of an encoded probe for decoding by hybridization.

FIG. 32 is a schematic diagram illustrating some of the factors considered in the design of an encoded probe for decoding by hybridization.

Figure 33A:
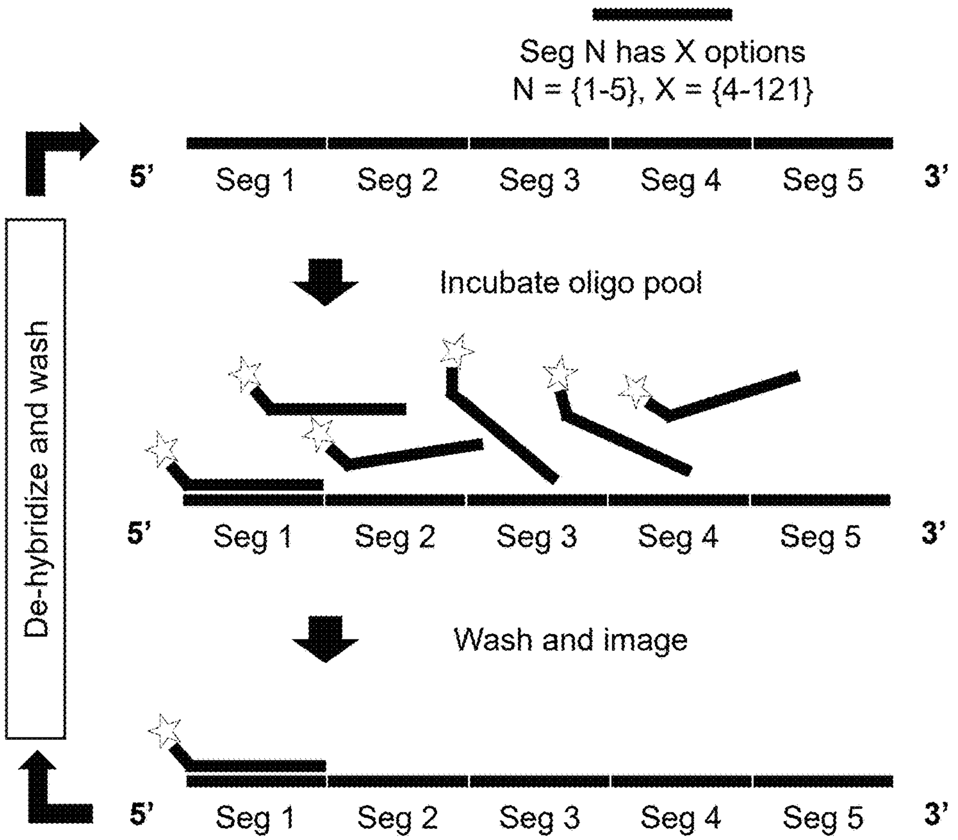
FIG. 33A is a schematic diagram illustrating an overview of process for decoding by hybridization.

FIG. 33A is a schematic diagram illustrating an overview of process for decoding by hybridization. For example, a code may include 5 segments and decoding may use 1 flow/segment, 4 colors or oligonucleotides in the oligo pool/flow. The decoding by hybridization process may include repeated cycles of hybridizing a code sequence with a decoding oligonucleotide pool (decoding oligos) comprising fluorescently labeled oligos, washing the hybridization reaction to remove unbound decoding oligos, imaging the decoding reaction to determine the identity of the hybridized decoding oligo, and de-hybridizing the code sequence to initiate a subsequent decoding cycle.

Figure 33B:
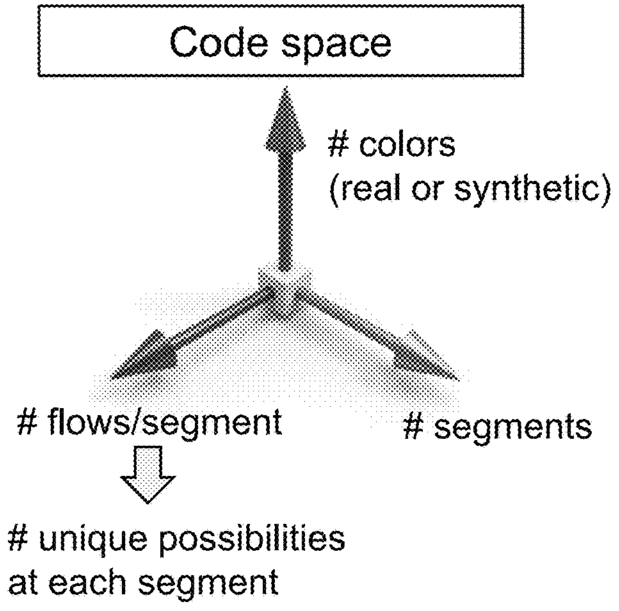
FIG. 33B is a schematic diagram illustrating the code space in decoding by hybridization.

FIG. 33B is a schematic diagram illustrating the code space in decoding by hybridization. For example, the code space may include the number of colors (real or synthetic), the number of flows per segment and the number of unique possibilities at each segment, and the number of segments in the code.

Figure 34:
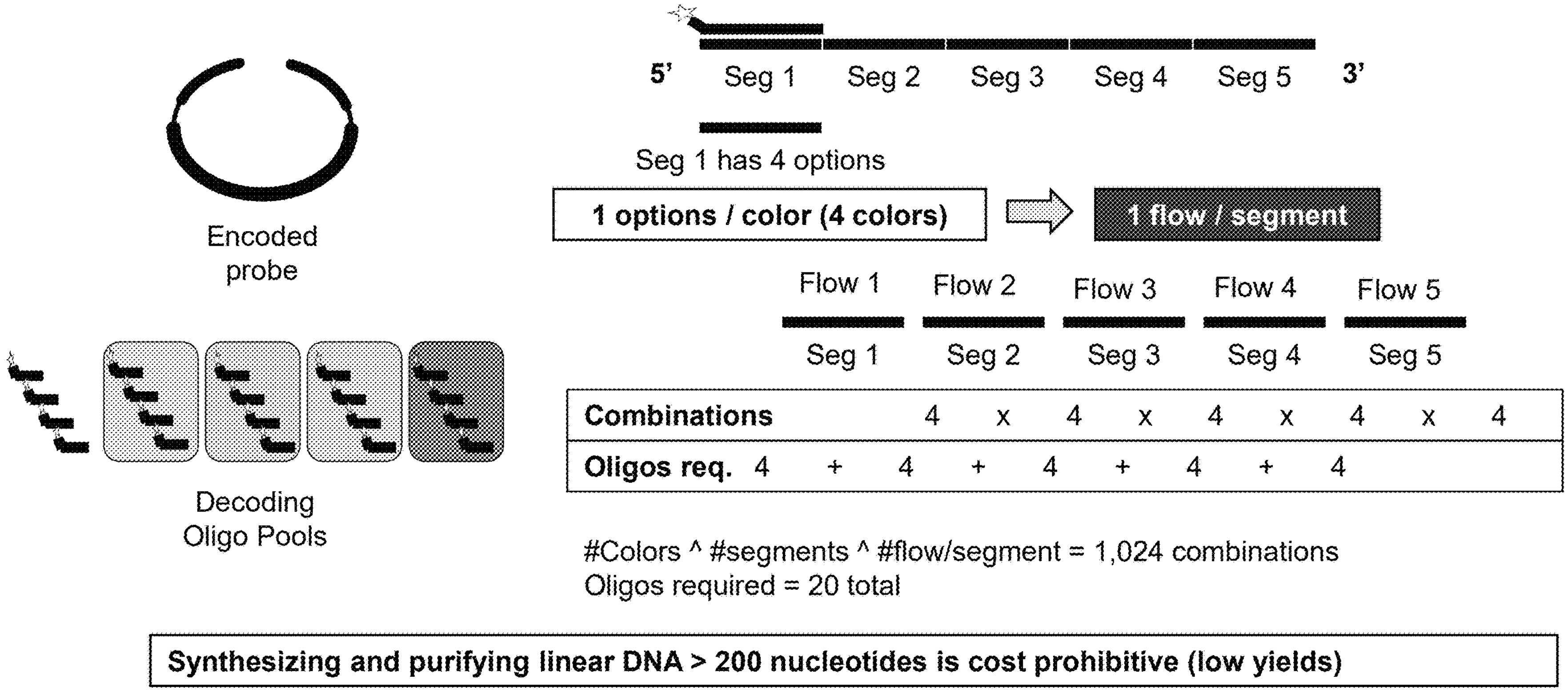
FIG. 34 is a schematic diagram of an example of a method for encoding symbols onto each segment of a code.

FIG. 34 is a schematic diagram of an example of a method for encoding symbols onto each segment of a code. In this example, the code comprises 5 segments (e.g., seg 1 through seg 5) which requires relatively few decoding oligos for decoding by hybridization. A code with 5 segments would require 5 decoding pools with 4 different labeled decoding oligos flowed for each segment decoded (i.e., 20 different decoding oligos are required).

Figure 35:
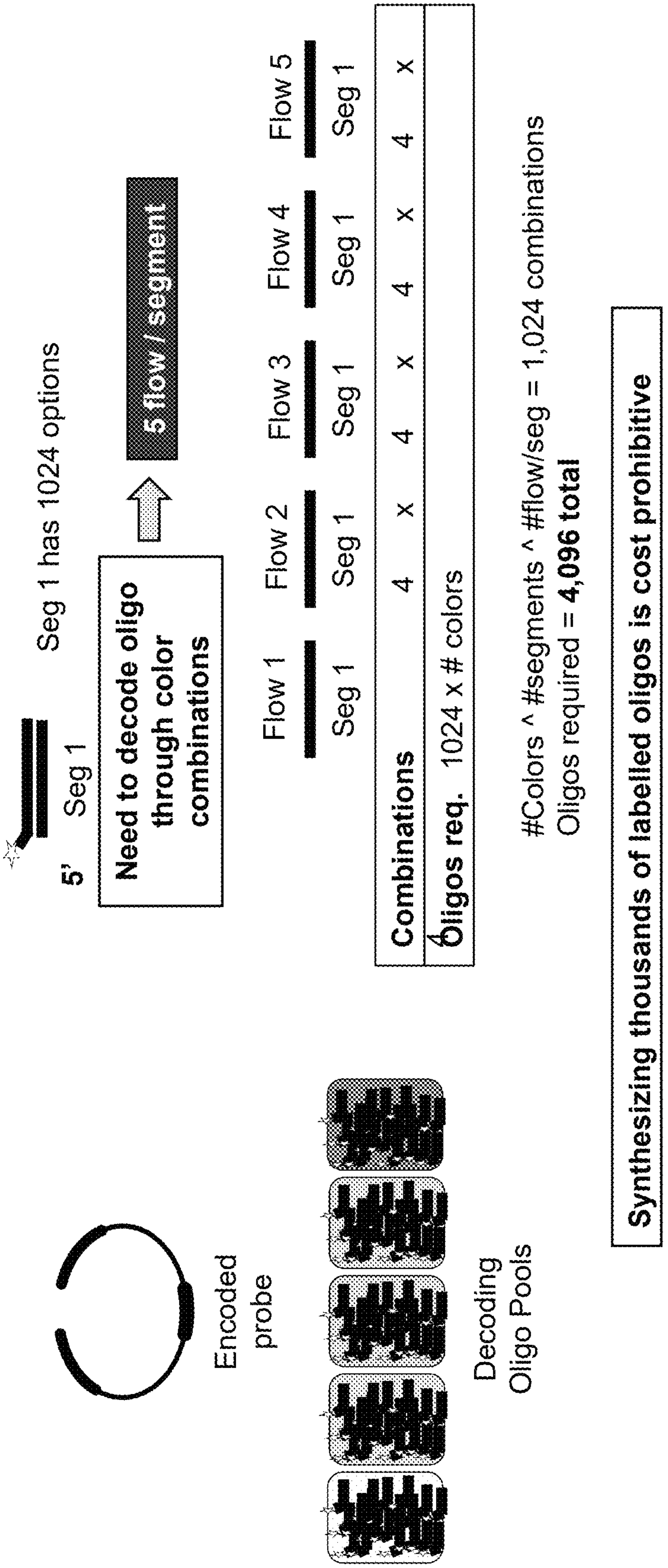
FIG. 35 is a schematic diagram of another example of a method for encoding symbols onto a code wherein the length of the code sequence comprises a single segment that requires a relatively large number of decoding oligos.

FIG. 35 is a schematic diagram of another example of a method for encoding symbols onto a code wherein the length of the code sequence comprises a single segment that requires a relatively large number of decoding oligos.

Figure 36:
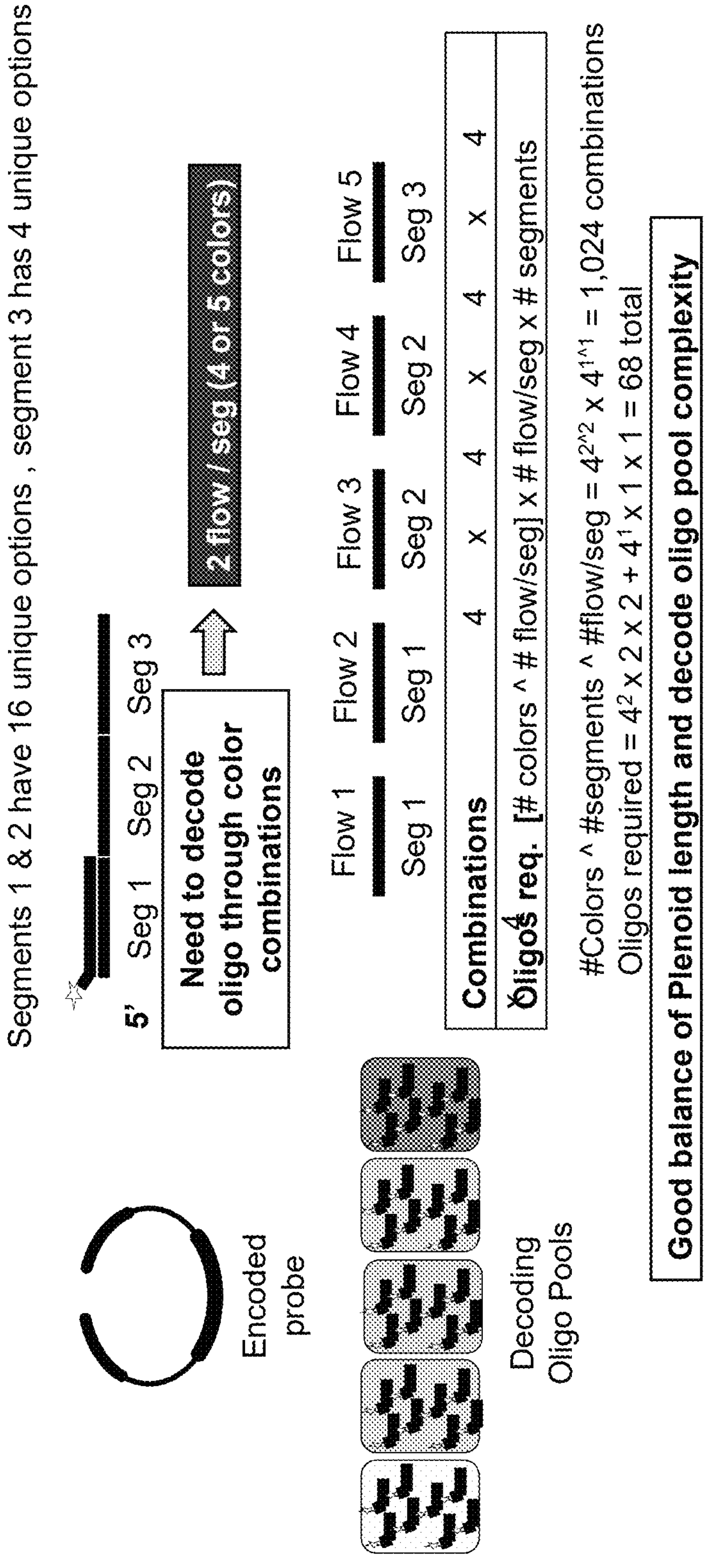
FIG. 36 is a schematic diagram of another example of a method for encoding symbols onto a code wherein a mix of segment number and flows/segment in the decoding process balances the length of a code and the complexity required in the decoding oligo pool.

FIG. 36 is a schematic diagram of another example of a method for encoding symbols onto a code wherein the mix of segment number and flows/segment in the decoding process balances the length of a code and the complexity required in the decoding oligo pool.

FIG. 37 is a screenshot of an example of the permutations (e.g., colors, flows/segment, total segments, and total flows) that may be used to achieve a relatively large combination space (codes pace) from which select a subset of codes.

Figures 38A, 38B:
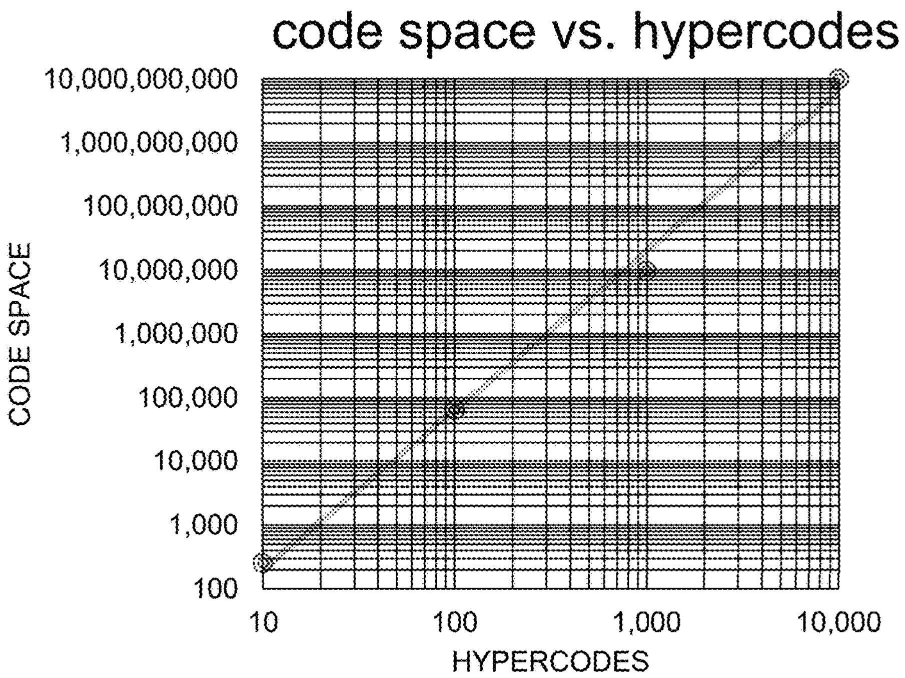
FIG. 38A is a plot showing the relationship of the number of codes in a code space.
FIG. 38B is a summary table of the number of segments, flows, and colors required for a given number of targets for detection.

FIG. 38A and FIG. 38B are a plot showing the relationship of the number of codes in a code space, and a summary table of the number of segments, flows, and colors required for a given number of targets for detection, respectively.

FIG. 39 is a schematic diagram of an example of a trellis code and a process of using the trellis code to select a set of codes with desired properties for an assay from a large code space. In this example, a 4-color system is used, which enables error correction in the system to maximize decoding sensitivity and minimize the overall error rate.

Figure 40A:
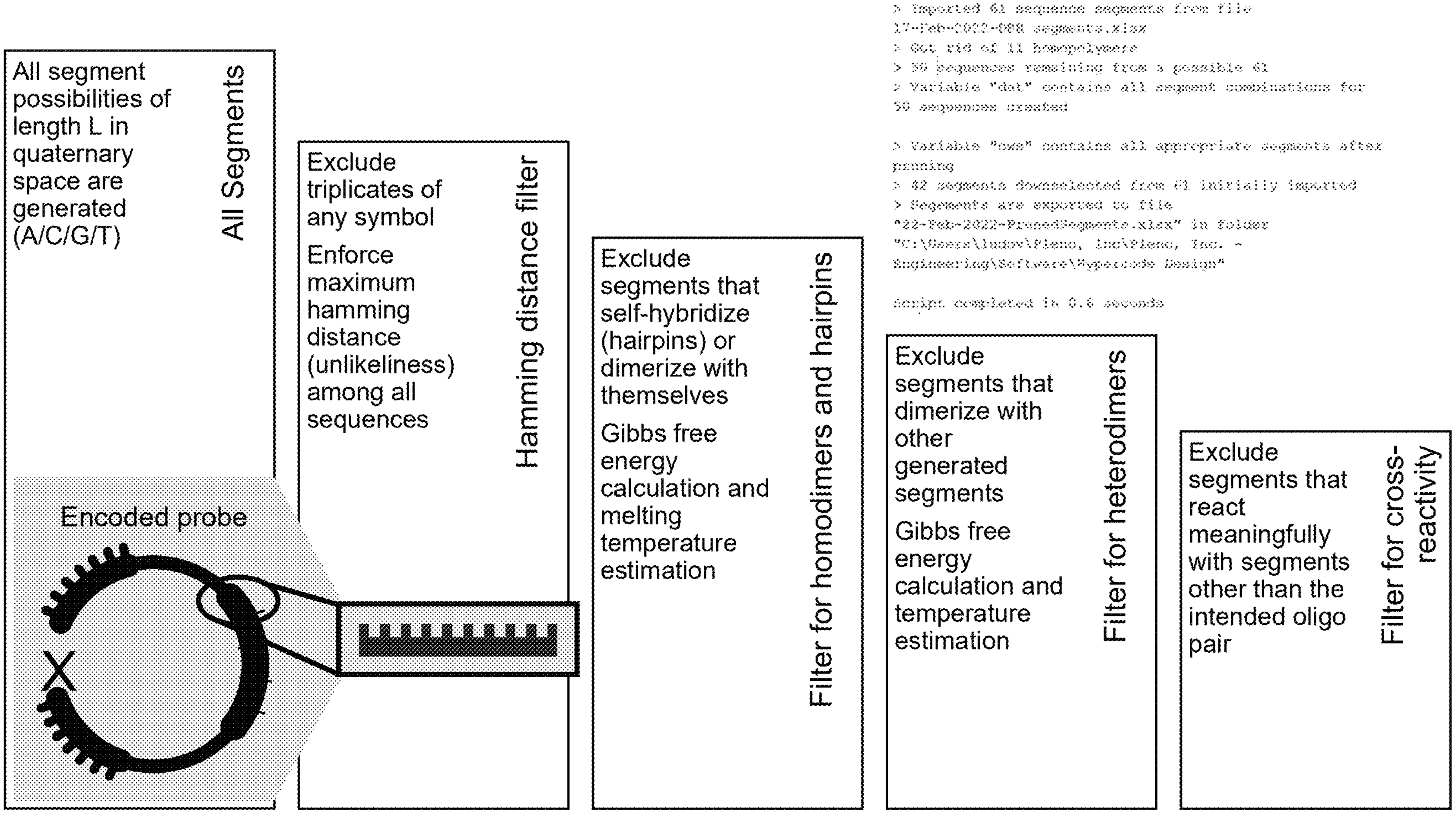
FIG. 40A is a representation of a strategy for designing oligo segments on a probe that will encode for the symbols that make up the trellis code (or other type of code).

FIG. 40A and FIG. 40B are a representation of a strategy for designing oligo segments on a probe that will encode for the symbols that make up the trellis code (or other). The strategy may include translating the symbol from the code into the DNA backbone of the probe, either through 1 DNA base if sequencing, or decoding by (may be more than 1 base), or many bases if using decoding by hybridization (e.g., between 10-20 bases, though longer and shorter are possible).

Figure 41:
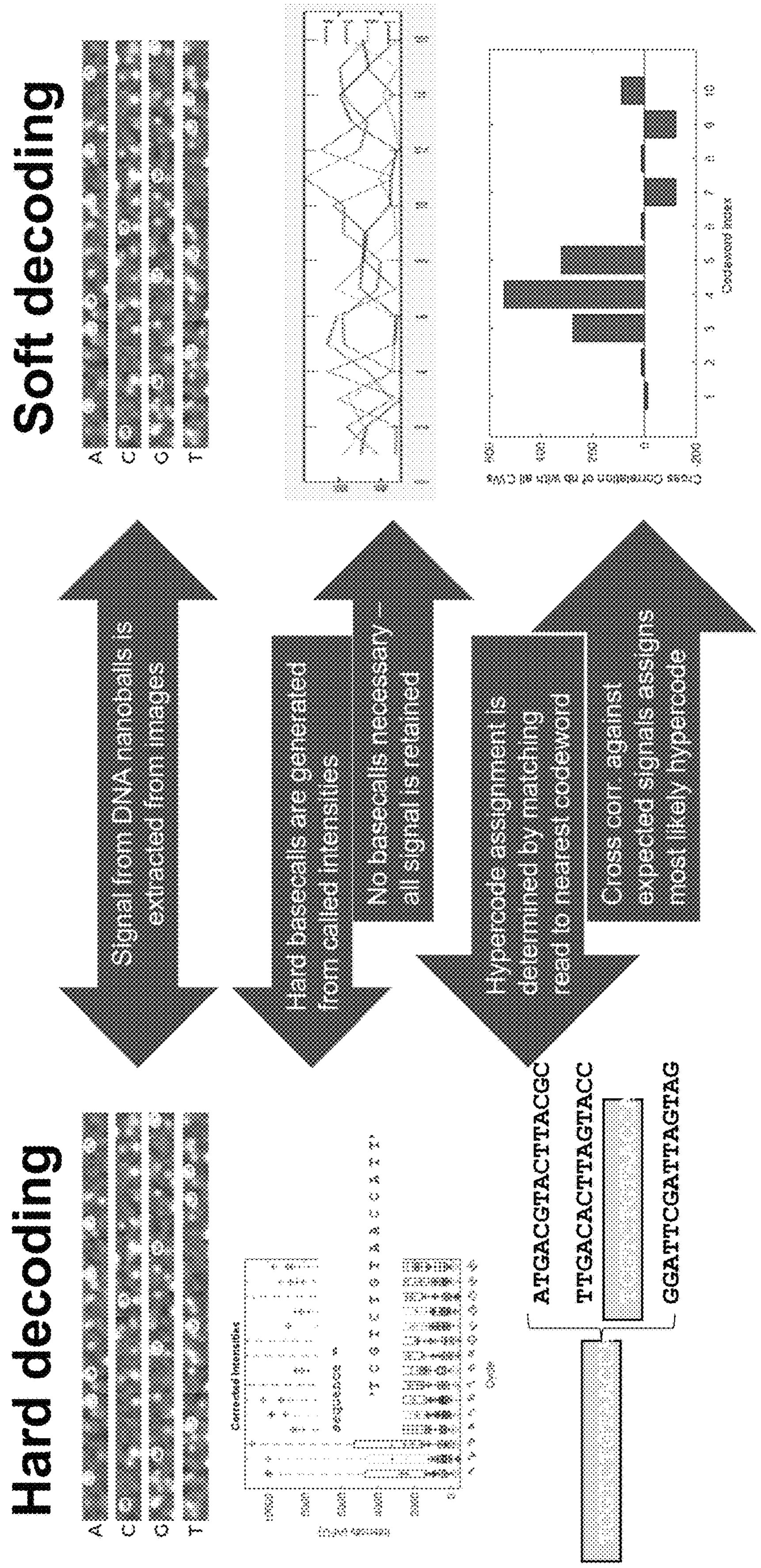
FIG. 41 is a representation of an overview of a decoding process comparing hard decoding vs. soft decoding.

FIG. 41 is a representation of an overview of a decoding process comparing hard decoding vs. soft decoding.

Figure 42:
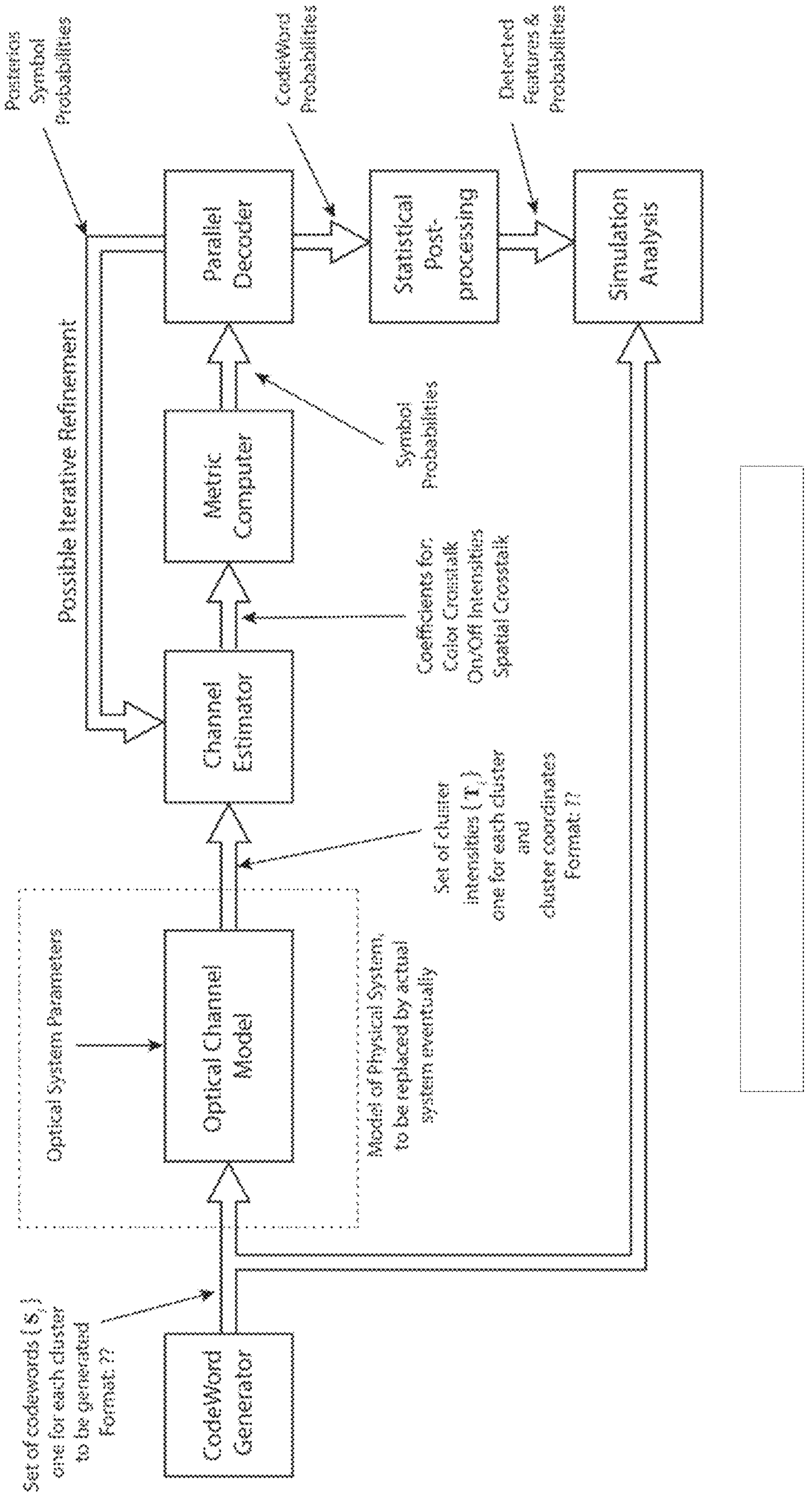
FIG. 42 is a schematic diagram of an example of a soft decoding process that may be used in the assays of the invention.

FIG. 42 is a schematic diagram of an example of a soft decoding process that may be used in the assays of the invention.

FIG. 43 is a summary of a channel model for a base calling algorithm that may be used in a soft decoding process. The model may include, for example, parameters for signal decay, amplitude noise, color crosstalk, signal leakage in time and system noise.

Figure 44:
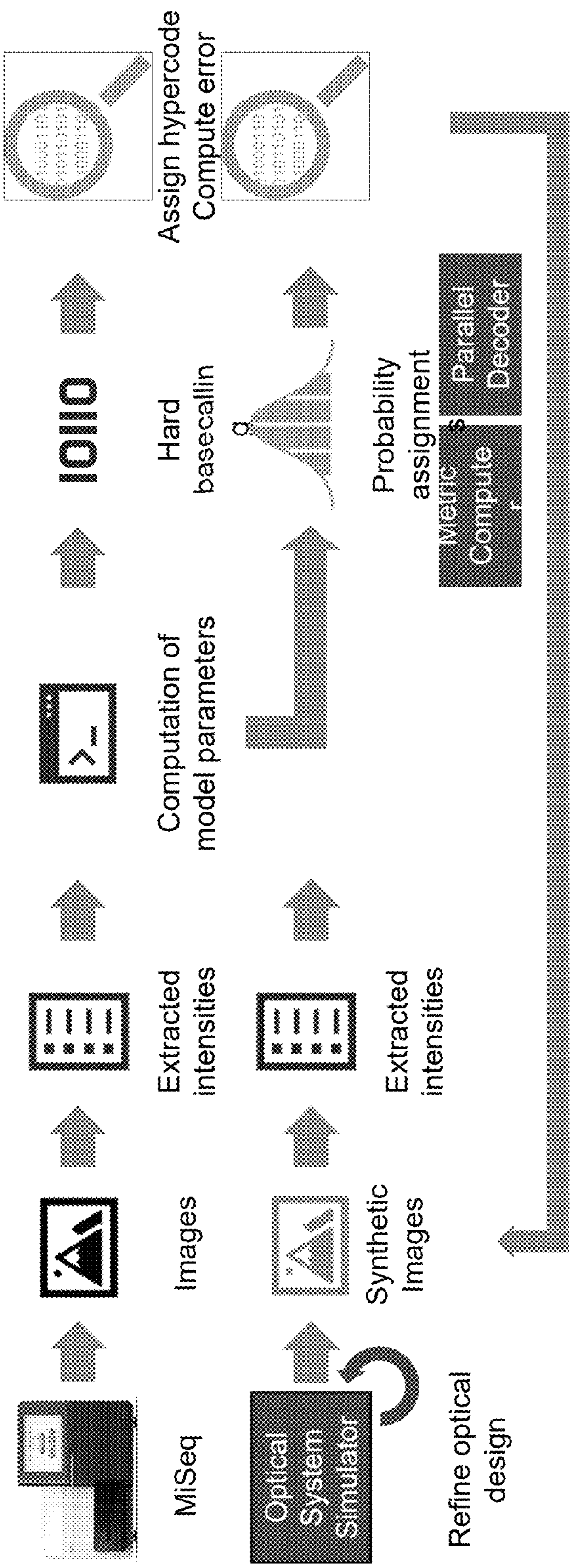
FIG. 44 is a flow chart illustrating aspects of the disclosed methods.

FIG. 44 is a schematic diagram illustrating an overview of an encoded assay analysis process.

In one embodiment of the invention, a method is provided for conducting an assay for a set of target analytes that includes: (a) performing a recognition and amplification event on a set of target analytes potentially present in a sample to generate a set of rolling circle amplification products (RCPs) from the target analytes or representative of the target analytes present in the sample, wherein each of the RCPs comprises multiple copies of a nucleic acid code from a set of codes, wherein each code comprises at least one segment encoding one or more symbols that correspond to a sequence of one or more nucleotides; (b) recording signal produced in response to interrogation of each segment of the codes; and (c) upon completion of the interrogation, determining a probably of the presence of each of the codes by applying a soft-decision probabilistic decoding algorithm to the recorded signal, wherein detecting the presence of the code is indicative of the presence of the target analyte.

CONCLUDING REMARKS

Various modifications and variations of the disclosed methods, compositions and uses of the invention will be apparent to the skilled person without departing from the scope and spirit of the invention. Although the invention has been disclosed in connection with specific preferred aspects or embodiments, it should be understood that the invention as claimed should not be unduly limited to such specific aspects or embodiments.

The present invention may be implemented using hardware, software, or a combination thereof and may be implemented in one or more computer systems or other processing systems. In one aspect, the invention is directed toward one or more computer systems capable of carrying out the functionality described herein.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

We claim:

1. A method of conducting an assay for a set of DNA targets, the method comprising:

(a) subjecting the set of DNA targets extracted from a biological sample to a recognition event, in which each DNA target of the set of DNA targets is uniquely recognized by and bound to at least one coded recognition element from a set of coded recognition elements, each coded recognition element comprising a target-specific binding site and a code from a set of codes, wherein the target-specific binding site is complementary to a known 3' region and a known 5' region of a DNA target of the set of DNA targets, wherein each code of the set of codes comprises at least one segment encoding one or more symbols, to yield a set of coded DNA targets, wherein each coded DNA target of the set of coded DNA targets comprises a DNA target of the set of DNA targets bound to a coded recognition element of the set of coded recognition elements, wherein the set of DNA targets comprises unamplified nucleic acids extracted from the biological sample;

(b) subjecting the set of coded recognition elements bound to the set of coded DNA targets to a molecular transformation event to yield a set of circularized coded recognition elements;

(c) introducing an exonuclease to the set of circularized coded recognition elements to reduce one or more recognition elements of the set of coded recognition elements that were not uniquely recognized by and bound to a DNA target of the set of DNA targets;

(d) performing rolling circle amplification of the set of circularized coded recognition elements to produce amplified circularized coded recognition elements, wherein the rolling circle amplification is performed on a surface; and (e) detecting the set of DNA targets associated with the amplified circularized coded recognition elements by decoding amplified codes of the amplified circularized coded recognition elements, wherein the decoding comprises performing soft decision decoding.

2. The method of claim 1, wherein the set of coded recognition elements comprises at least 10 coded recognition elements.

3. The method of claim 1, wherein the decoding the amplified codes comprises interrogating the at least one segment of each code of the amplified circularized coded recognition elements with a method comprising nucleic acid sequencing or nucleic acid hybridization.

4. The method of claim 3, wherein the nucleic acid sequencing comprises nanopore sequencing, Sanger sequencing, sequencing by synthesis, pyrosequencing, single molecule real-time sequencing, or sequencing by ligation.

5. The method of claim 1, wherein the decoding the amplified codes comprises interrogating the at least one segment of each code of the amplified circularized coded recognition elements by nucleic acid hybridization with one or more hybridization probes having at least one label to produce a detectable signal.

6. The method of claim 1, wherein each code of the amplified circularized coded recognition elements comprises a plurality of segments including the at least one segment, and wherein the decoding the amplified codes comprises interrogating the at least one segment of each code of the amplified circularized coded recognition elements by nucleic acid hybridization with a plurality of hybridization probes, wherein each hybridization probe of the plurality of hybridization probes comprises a label that is distinct from the other hybridization probes of the plurality of hybridization probes to produce multiple detectable signals.

7. The method of claim 1, wherein the molecular transformation event comprises a ligation reaction in which each coded recognition element of the set of coded DNA targets is ligated to form the set of circularized coded recognition elements.

8. The method of claim 7, wherein the subjecting the set of coded recognition elements of the set of coded DNA targets to the molecular transformation event comprises introducing the set of coded recognition elements to a ligase enzyme under conditions sufficient to ligate and circularize the coded recognition elements.

9. The method of claim 1, wherein the set of coded recognition elements comprises padlock probes or molecular inversion probes.

10. The method of claim 9, wherein the set of coded recognition elements further comprises:

(i) a 5' probe arm and a 3' probe arm; and (ii) a splint oligonucleotide probe comprising:

(A) a 5' region configured to bind to the 3' probe arm; and (B) a 3' region configured to bind to the 5' probe arm.

11. The method of claim 1, wherein the set of coded recognition elements further comprises:

(i) one or more sequencing primer binding sequences;

(ii) one or more amplification primer binding sequences;

(iii) a unique identifier sequence (UMI);

(iv) a sample index;

(v) a restriction enzyme site; or (vi) any combination of (i) to (v).

12. The method of claim 11, wherein the one or more amplification primer binding sequences comprises a universal primer binding sequence that is common to all coded recognition elements of the set of coded recognition elements.

13. The method of claim 1, wherein the surface comprises a cation-coating layer.

14. The method of claim 1, wherein the surface comprises a density of the amplified circularized coded recognition elements of 23,000 to 110,000 amplified circularized coded recognition elements per square millimeter ($mm^2$).

15. The method of claim 1, further comprising condensing the amplified circularized coded recognition elements by addition of one or more condensing agents, wherein the one or more condensing agents comprises:

(i) one or more cationic additives; or (ii) one or more multivalent oligonucleotide sequences configured to crosslink sites on the amplified circularized coded recognition elements.

16. The method of claim 15, wherein the amplified circularized coded recognition elements comprise one or more modified nucleotides that participate in a crosslinking reaction with the one or more multivalent oligonucleotide sequences.

17. The method of claim 1, wherein the set of codes are error corrected.

18. The method of claim 1, wherein each code of the set of codes has a length comprising 5 to 100 contiguous nucleotides.

19. The method of claim 1, wherein each code of the set of codes comprises 3 or more segments including the at least one segment.

20. The method of claim 1, wherein each code of the set of codes comprises at least 16 symbols including the one or more symbols.

21. The method of claim 1, wherein the set of DNA targets comprises 100 or more DNA targets.

22. The method of claim 1, wherein the set of DNA targets comprises:

(i) one or more substitutions, insertions and/or deletions; or (ii) a copy number variation.

23. The method of claim 1, wherein the set of DNA targets comprises one or more methylated nucleotides.

24. The method of claim 1, wherein the set of DNA targets comprises a pathogenic nucleic acid.

25. The method of claim 24, wherein each coded recognition element of the set of coded recognition elements has a concentration of about 250 pM.

26. The method of claim 1, wherein the subjecting the set of DNA targets to the recognition event comprises introducing the set of DNA targets at an input concentration of 10 picomolar (pM) to 100 pM to the set of coded recognition elements.

27. The method of claim 1, wherein each code of the set of codes comprises 4 or more segments including the at least one segment and at least 16 symbols including the one or more symbols.

* * * * *